US009746470B2

(12) United States Patent
Taipale et al.

(10) Patent No.: US 9,746,470 B2
(45) Date of Patent: Aug. 29, 2017

(54) CHAPERONE INTERACTION ASSAYS AND USES THEREOF

(75) Inventors: Mikko Taipale, Boston, MA (US); Susan Lindquist, Chestnut Hill, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 178 days.

(21) Appl. No.: 14/116,923

(22) PCT Filed: May 9, 2012

(86) PCT No.: PCT/US2012/037131
§ 371 (c)(1),
(2), (4) Date: May 23, 2014

(87) PCT Pub. No.: WO2012/154858
PCT Pub. Date: Nov. 15, 2012

(65) Prior Publication Data
US 2014/0315214 A1    Oct. 23, 2014

Related U.S. Application Data

(60) Provisional application No. 61/484,108, filed on May 9, 2011, provisional application No. 61/613,908, filed on Mar. 21, 2012.

(51) Int. Cl.
| | | |
|---|---|---|
| *C12Q 1/00* | (2006.01) | |
| *G01N 33/53* | (2006.01) | |
| *G01N 33/573* | (2006.01) | |
| *G01N 33/543* | (2006.01) | |
| *G01N 33/68* | (2006.01) | |
| *C12Q 1/48* | (2006.01) | |
| *C12Q 1/66* | (2006.01) | |
| *G01N 33/50* | (2006.01) | |
| *G01N 33/574* | (2006.01) | |

(52) U.S. Cl.
CPC ........... *G01N 33/573* (2013.01); *C12Q 1/485* (2013.01); *C12Q 1/66* (2013.01); *G01N 33/502* (2013.01); *G01N 33/54306* (2013.01); *G01N 33/57484* (2013.01); *G01N 33/6845* (2013.01); *G01N 33/6872* (2013.01); *G01N 2500/02* (2013.01); *G01N 2800/60* (2013.01)

(58) Field of Classification Search
CPC ............................. A61K 39/11; G01N 33/573
USPC .......................................................... 435/346
See application file for complete search history.

(56) References Cited

U.S. PATENT DOCUMENTS

| | | | | |
|---|---|---|---|---|
| 2002/0019006 A1* | 2/2002 | Yuan | ................... | C12N 15/1055 435/6.16 |
| 2002/0102606 A1* | 8/2002 | Heichman | ............ | C12N 9/1205 435/7.1 |
| 2002/0106676 A1* | 8/2002 | Roch | ....................... | C07K 14/47 435/6.16 |
| 2002/0151484 A1* | 10/2002 | Legrain | ................ | C07K 14/005 435/5 |
| 2002/0177212 A1* | 11/2002 | Patterson | ........... | C07K 14/4703 435/226 |
| 2003/0040089 A1* | 2/2003 | Legrain | .................. | C07K 14/47 435/183 |
| 2003/0044787 A1* | 3/2003 | Joung | ................ | C12N 15/1055 435/6.16 |

(Continued)

FOREIGN PATENT DOCUMENTS

| | | | | |
|---|---|---|---|---|
| AU | 2005221470 | * 10/2005 | ............. | C07K 14/47 |
| EP | 1178116 | * 2/2002 | ............. | C12N 15/62 |

(Continued)

OTHER PUBLICATIONS

Smith, Victoria et al.,Cancer Chemotherapy Pharmacology, 2005, vol. 56, pp. 126-137.*
Eto, Danelle S et al, Integrin-Mediated Host Cell Invasion byType-1 Piliated Uropathogenic *Escherichia coli*, PLOS Pathogens, vol. 3(7), e100, 2007, pp. 949-961.*
Usmani et al, Journal of Hematology, vol. 3(40) Oct. 26, 2010, pp. 1-8.*
DEoddareddy, M et al Structure based design of heat shock protein 90 inhibitors acting as anticancer agents, Bioorganic and Medicinal Chemistry, vol. 19, 2011, pp. 1714-1720, online Jan. 19, 2011.*

(Continued)

*Primary Examiner* — Albert Navarro
(74) *Attorney, Agent, or Firm* — Lisa M. Warren, Esq.; Morse, Barnes-Brown & Pendleton, P.C.

(57) ABSTRACT

In some aspects, the invention provides methods of identifying, detecting, and/or measuring protein-protein interactions. In some aspects, the invention provides methods of identifying and/or characterizing modulators of protein-protein interactions. In some aspects, the invention provides methods of identifying and/or characterizing modulators of protein activity, wherein the methods are based at least in part on measuring interaction between a chaperone and client protein. In some aspects, the invention provides methods for identifying and/or characterizing compounds and/or for assessing compound specificity, wherein the methods are based at least in part on measuring interaction between a chaperone and client protein. In some embodiments, a client protein is a kinase. In some embodiments, a compound is a kinase inhibitor. In some aspects, the invention provides methods of profiling kinase inhibitor specificity. In some aspects, the invention provides assay systems and/or reagents useful for performing one or more of the inventive methods. In some aspects, the invention provides newly identified targets of a variety of kinase inhibitors. In some aspect, the invention provides methods of inhibiting kinases identified herein as targets of certain kinase inhibitors. In some aspects, the invention provides methods of treating a disease, e.g., cancer, by inhibiting one or more kinase(s) newly identified as targets of certain kinase inhibitors.

14 Claims, 29 Drawing Sheets

(56) References Cited

U.S. PATENT DOCUMENTS

| | | | |
|---|---|---|---|
| 2005/0026894 A1* | 2/2005 | Tian | C07D 491/04 514/183 |
| 2005/0277116 A1* | 12/2005 | McKeon | G01N 33/5008 435/6.16 |
| 2006/0099645 A1 | 5/2006 | Wrana et al. | |
| 2006/0166266 A1* | 7/2006 | Poole | C12N 15/1055 435/7.1 |
| 2006/0205705 A1* | 9/2006 | Ross | C07D 225/02 514/183 |
| 2006/0252733 A1* | 11/2006 | Jansen | A61K 31/56 514/169 |
| 2007/0031815 A1* | 2/2007 | Jenkins | G01N 33/6872 435/4 |
| 2007/0224620 A1* | 9/2007 | Hartzell | G01N 33/54306 435/6.12 |
| 2008/0039616 A1* | 2/2008 | Zenser | C07K 1/22 536/23.1 |
| 2008/0096903 A1* | 4/2008 | Chen | C07D 209/12 514/263.1 |
| 2008/0206888 A1* | 8/2008 | Miller et al. | 436/501 |
| 2009/0035303 A1* | 2/2009 | Nakamura | C12Q 1/48 424/133.1 |
| 2009/0082265 A1* | 3/2009 | Bartel | A61K 31/7052 514/1.2 |
| 2009/0087436 A1* | 4/2009 | Roch | A61K 31/7052 424/139.1 |
| 2009/0156536 A1* | 6/2009 | Kim | C07K 16/30 514/44 R |
| 2010/0075326 A1* | 3/2010 | Jin | C12N 15/1055 435/6.11 |
| 2010/0143454 A1* | 6/2010 | McLinden | C07K 14/005 424/450 |
| 2010/0173408 A1* | 7/2010 | Eyckerman | C07K 14/71 435/325 |
| 2010/0247589 A1* | 9/2010 | Fahnestock | A61K 8/0241 424/401 |
| 2011/0206694 A1* | 8/2011 | Fleckenstein | A61K 39/0258 424/169.1 |
| 2011/0312980 A1* | 12/2011 | Chiosis | C07D 473/34 514/263.24 |
| 2012/0308568 A1* | 12/2012 | Kang | A61K 39/00 424/135.1 |
| 2014/0234858 A1* | 8/2014 | Santagata | G01N 33/57484 435/7.1 |
| 2014/0235471 A1* | 8/2014 | Bergo | G01N 33/6845 506/9 |

FOREIGN PATENT DOCUMENTS

| | | | | |
|---|---|---|---|---|
| WO | 99/42612 | * | 8/1999 | C12Q 1/68 |
| WO | WO 03/025213 | | 3/2003 | |
| WO | 03/102221 | * | 12/2003 | C12Q 1/00 |
| WO | 2004/023146 | * | 3/2004 | G01N 33/68 |
| WO | WO 2004/097428 | | 11/2004 | |

OTHER PUBLICATIONS

Millson, S et al, Biochemical Pharmacology, vol. 79, 2010, pp. 1581-1588.*

Barrios-Rodiles, et al., High-Throughput Mapping of a Dynamic Signaling Network in Mammalian Cells. *Science*, 307: 1621-1625 (2205).

Taipale, et al., HSP90 at the Hub of Protein Homeostasis: Emerging Mechanistic Insights. *Nature Reviews Molecular Cell Biology*, 11(7): 515-528 (2010).

Supplementary Partial European Search Report for EP Application No. EP 12782991, dated Feb. 9, 2015.

Hurst, et al., "Protein—protein interaction studies on protein arrays: Effect of detection strategies on signal-to-background ratios", *Analytical Biochemistry*, 392; 45-53 (2009).

Jung, et al., "Stabilization of Phosphatidylinositol 4-Kinase Type II$\beta$ by Interaction with Hsp 90-.", *J. Biol. Chem*, 286(14); 12775-12784 (2011).

International Search Report for International Application PCT/US2012/037131, dated Sep. 21, 2012.

Taipale, Mikko, et al., Quantitative High-Throughput Analysis of HSP90/Kinase Interactions, Whitehead Institute, Cambridge, MA USA, HHMI, Howard Hughes Medical Institute, Cambridge, MA USA, 1 page, Aug. 18-22, 2010.

* cited by examiner

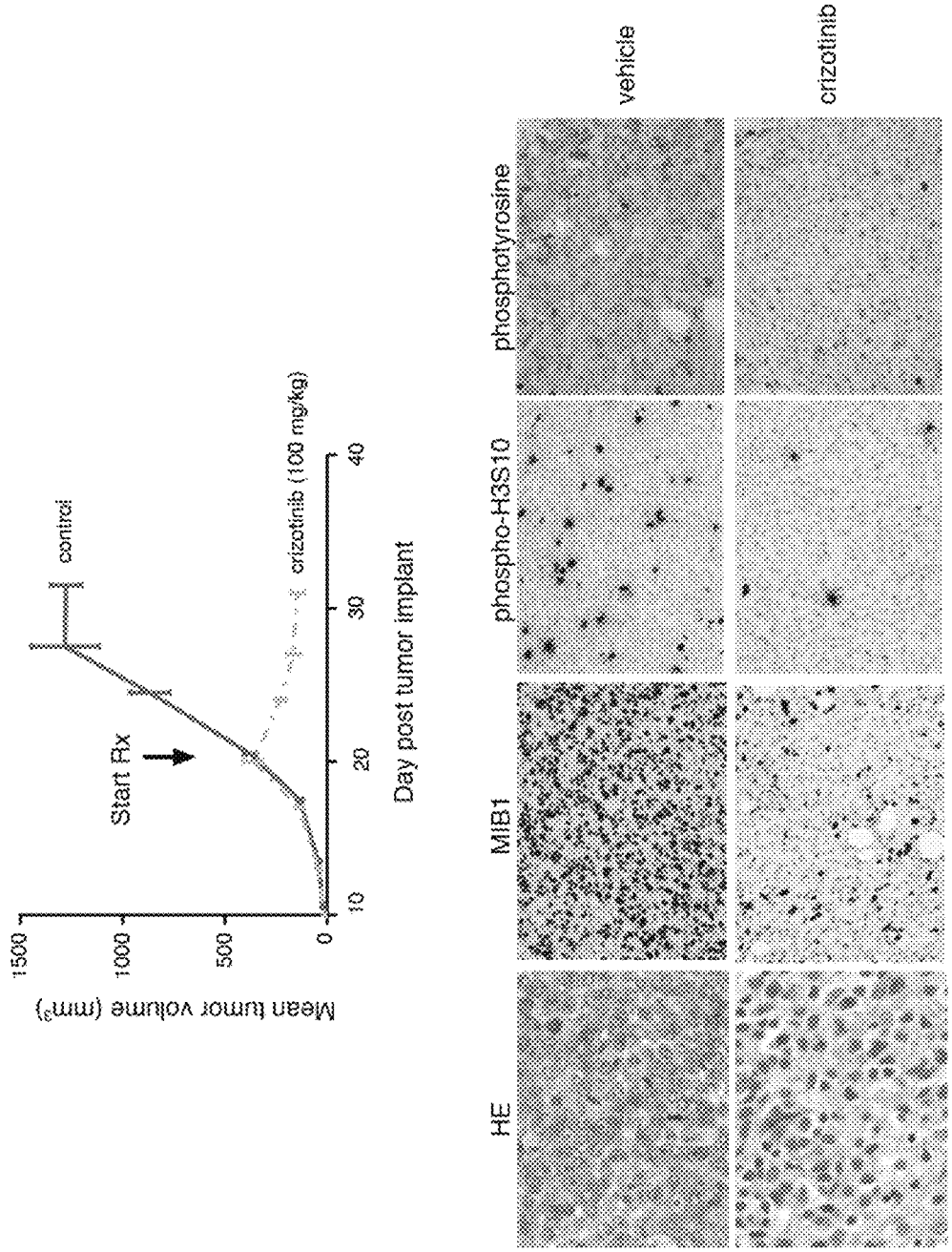

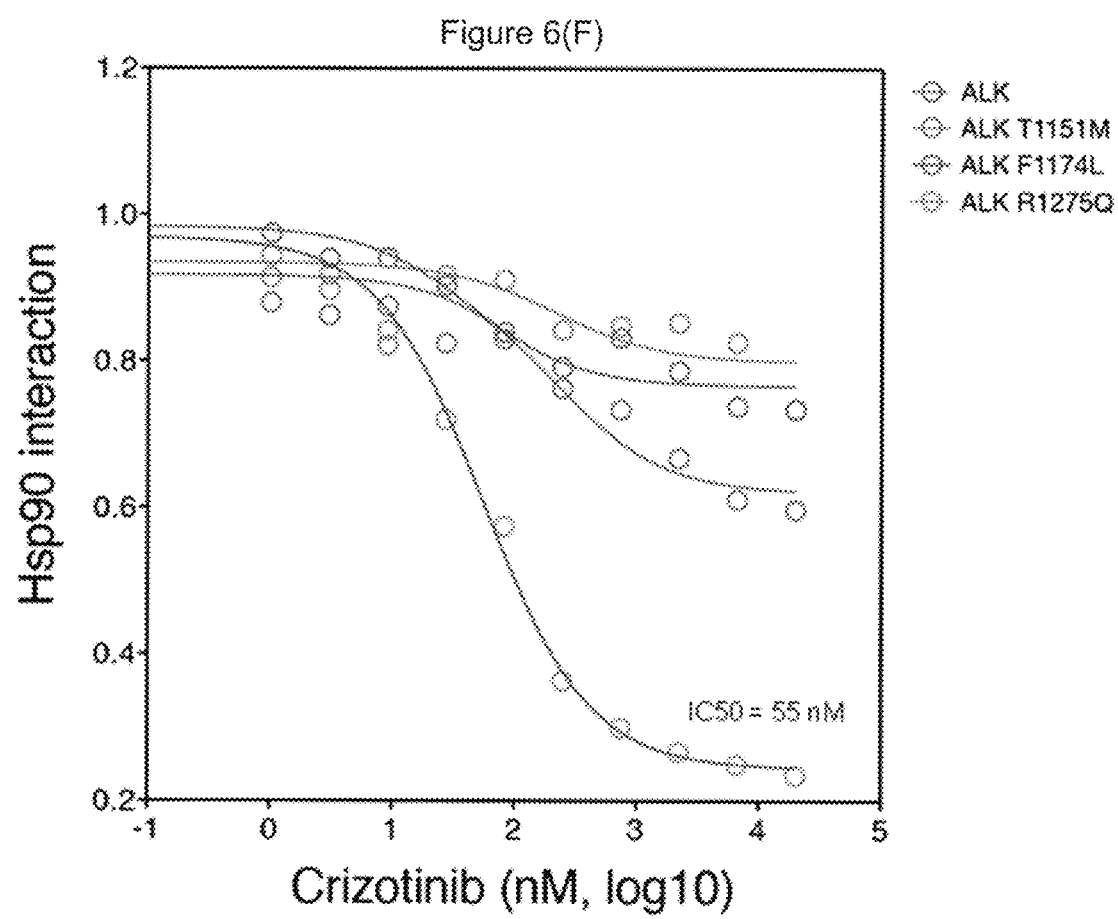

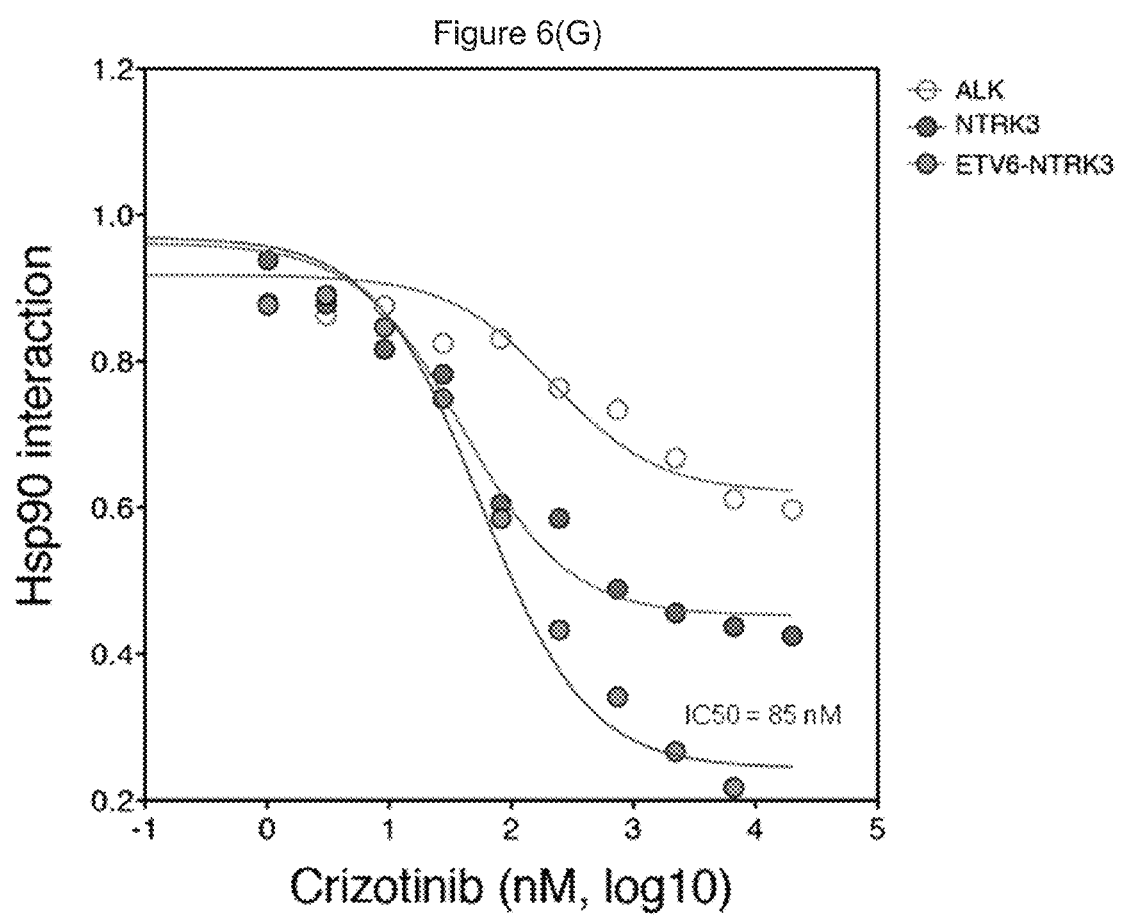

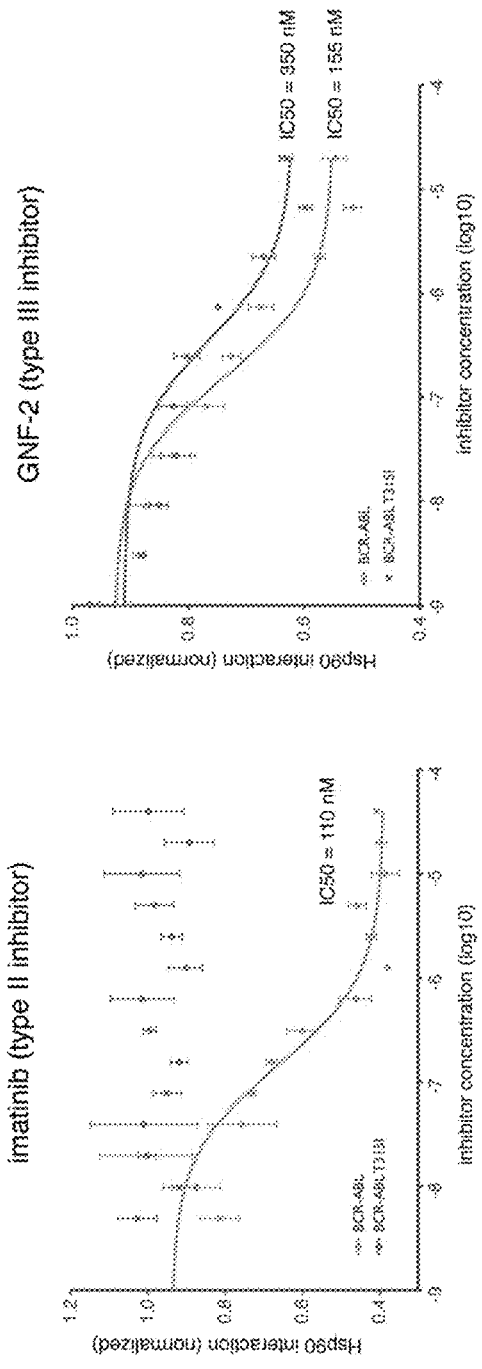
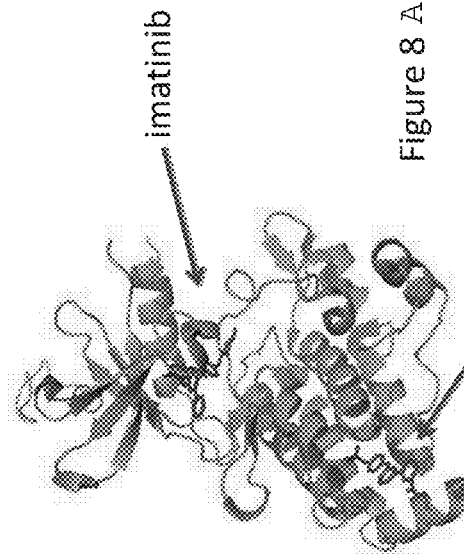
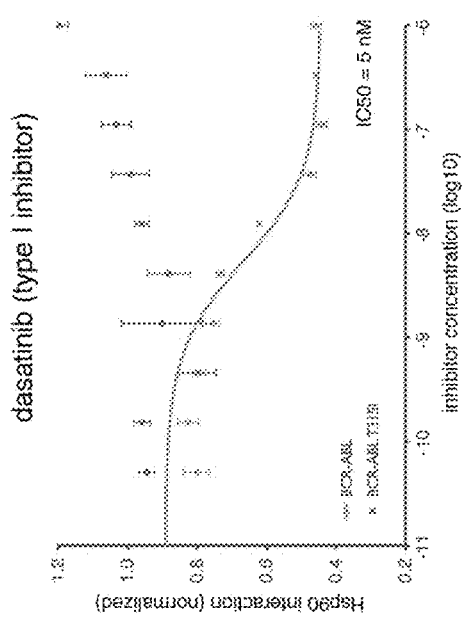
Figure 8 A (B)

Figure 11

Quantitative network of chaperone/co-chaperone interactions

| TPR domains | p23 domains | Others | Chaperones |
|---|---|---|---|
| PPID (Cyp40) | PTGES3 (p23) | AHSA1 (Aha1) | HSP90AA1 (HSP90α) |
| FKBPL (W/Sp39) | SUGT1 (Sgt1) | AHSA2 (Aha2) | HSP90AB1 (HSP90β) |
| FKBP4 (Fkbp52) | NUDC | BAG1 | HSPA8 (Hsp70) |
| FKBP5 (Fkbp51) | NUDCD1 | BAG2 | HSP90B1 (Grp94) |
| FKBP6 (Fkbp36) | NUDCD2 | BAG3 | TCP1 (TRIC/CCT) |
| FKBP8 (Fkbp38) | NUDCD3 | BAG4 | |
| UNC45A | CHORDC1 | BAG5 | |
| UNC45B | ITGB1BP2 (melusin) | CDC37 | |
| STIP1 (Hop) | CACYBP | CDC37L1 | Controls |
| DYX1C1 | LRRC6 | DNAJA4 | EGFP |
| AIP (XAP) | PTPLAD1 | DNAJC7 | DsRed |
| PPP5C (Pp5) | AARSD1 | HSF1 | Renilla luciferase |
| STUB1 (Chip) | USP19 | IRS4 | Gaussia luciferase |
| TTC1 (Tpr1) | | | CBL (ubiquitin ligase) |
| TTC4 | | | GBM1 (GTPase) |
| RPAP3 | | | |

All proteins tagged with Renilla luciferase and 3xFLAG-V5

SEQUENCE LISTING

<160> NUMBER OF SEQ ID NOS: 8

<210> SEQ ID NO 1
<211> LENGTH: 17
<212> TYPE: PRT
<213> ORGANISM: Artificial
<220> FEATURE:
<223> OTHER INFORMATION: Gaussia luciferase signal sequence

<400> SEQUENCE: 1

Met Gly Val Lys Val Leu Phe Ala Leu Ile Cys Ile Ala Val Ala Glu
1               5                   10                  15

Ala

<210> SEQ ID NO 2
<211> LENGTH: 6
<212> TYPE: PRT
<213> ORGANISM: Artificial
<220> FEATURE:
<223> OTHER INFORMATION: sequence duplicated in human HSP90 alpha
      construct

<400> SEQUENCE: 2

Asp Glu Asp Asp Pro Thr
1               5

<210> SEQ ID NO 3
<211> LENGTH: 15
<212> TYPE: PRT
<213> ORGANISM: Artificial
<220> FEATURE:
<223> OTHER INFORMATION: flexible linker

<400> SEQUENCE: 3

Ser Gly Gly Arg Ser Ser Gly Ser Gly Ser Thr Ser Gly Ser Gly
1               5                   10                  15

```
<210> SEQ ID NO 4
<211> LENGTH: 22
<212> TYPE: PRT
<213> ORGANISM: Artificial
<220> FEATURE:
<223> OTHER INFORMATION: flexible linker

<400> SEQUENCE: 4

Asp Ile Gln His Ser Gly Gly Arg Ser Ser Gly Ser Gly Ser Thr Ser
1               5                   10                  15

Gly Ser Gly Lys Thr Gly
            20

<210> SEQ ID NO 5
<211> LENGTH: 6
<212> TYPE: PRT
<213> ORGANISM: Artificial
<220> FEATURE:
<223> OTHER INFORMATION: sequence duplicated in human HSP90 beta
      construct

<400> SEQUENCE: 5

Asp Glu Asp Glu Val Ala
1               5

<210> SEQ ID NO 6
<211> LENGTH: 20
<212> TYPE: PRT
<213> ORGANISM: Artificial
<220> FEATURE:
<223> OTHER INFORMATION: fusion protein construct

<400> SEQUENCE: 6

Leu Gly Leu Gly Ile Asp Glu Asp Glu Val Ala Thr Ser Ala Ser Lys
1               5                   10                  15

Val Tyr Asp Asp
            20

<210> SEQ ID NO 7
<211> LENGTH: 5
<212> TYPE: PRT
<213> ORGANISM: Artificial
<220> FEATURE:
<223> OTHER INFORMATION: goat antibody binding epitope

<400> SEQUENCE: 7

Asp Asp Asp Asp Lys
1               5

<210> SEQ ID NO 8
<211> LENGTH: 17
<212> TYPE: PRT
<213> ORGANISM: Artificial
<220> FEATURE:
<223> OTHER INFORMATION: fusion protein construct

<400> SEQUENCE: 8

Val Leu Lys Asn Glu Gln Thr Gly Asp Glu Asp Glu Val Ala Ala Glu Glu
1               5                   10                  15
```

CHAPERONE INTERACTION ASSAYS AND USES THEREOF

RELATED APPLICATIONS

This application is a national stage filing under 35 U.S.C. 371 of International Application PCT/US2012/037131, filed May 9, 2012, which claims priority to U.S. Provisional Application Ser. No. 61/484,108, filed May 9, 2011, and U.S. Provisional Application Ser. No. 61/613,908, filed Mar. 21, 2012. The entire teachings of the afore-mentioned applications are incorporated herein by reference. International Application PCT/US2012/037131 was published under PCT Article 21(2) in English.

BACKGROUND

The human kinome comprises more than 500 kinases (Manning et al. Science, 298, 1912-1934, 2002). Kinases are involved in numerous cell signaling pathways and regulatory mechanisms and play important roles in a wide range of physiological processes and pathological conditions. Consequently, kinases are of considerable scientific and medical interest and represent an important class of drug targets. A number of kinase inhibitors have been approved for treatment of various types of cancer, and many more are currently in various stages of preclinical and clinical development. Imatinib (Gleeve®), the first small molecule kinase inhibitor to be approved for use in humans, is a mainstay of therapy for patients with chronic myeloid leukaemia. (CML). CML arises as a result of a chromosomal translocation in which part of the BCR gene from chromosome 22 is fused to the ABL gene on chromosome 9, producing a BCR-ABL fusion gene. ABL is a tyrosine kinase, and the BCR-ABL fusion results in dysregulation of the ABL tyrosine kinase domain, rendering the protein oncogenic. By inhibiting the kinase activity of the BCR-ABL protein, imatinib can induce a complete remission in most patients with CML.

Most kinase inhibitors target the kinase ATP-binding site, resulting in potential cross-reactivity. Cross-reactivity can sometimes be advantageous, as it offers the ability to multiple kinases using a single agent. However, use of inhibitors that inhibit multiple kinases can complicate the interpretation of experiments, especially if not all of the targets of the inhibitor are known. From a therapeutic standpoint, cross-reactivity may be beneficial, e.g., in situations in which multiple kinases contribute to a disease. However, cross-reactivity may result in undesirable side effects. Significant effort has been devoted to investigating kinase inhibitor specificity. For example, in vitro kinase assays involving recombinantly produced kinases or kinase domains and test substrates (often peptides containing a potential site for phosphorylation), are widely used. Similarly, screens to identify inhibitors of a particular kinase frequently entail assessing the ability of test compounds to inhibit phosphorylation of a test substrate in vitro. While these approaches are conceptually straightforward, they have a number of significant limitations. For example, it has been difficult to express and purify a number of kinases in full length form. Furthermore, in vitro assays inevitably fail to fully recapitulate the native cellular environment.

There is a need in the art for new methods of assessing kinase inhibitor specificity. There is also a need in the art for new methods of identifying kinase inhibitors.

SUMMARY

In one aspect, the invention provides quantitative protein-protein interaction assays. In some embodiments, the assays comprise isolating bait protein and bait-prey complexes and controlling for the amount of bait protein. In some embodiments, assays utilize luminescence for detection, e.g., of prey protein. A schematic diagram representing certain embodiments of a protein-protein interaction assay of the invention is presented FIG. 1. In some aspects, the invention provides a for detecting a protein-protein interaction, the method comprising steps of: (a) providing a lysate prepared from cells that express a prey protein and a bait protein, wherein the prey protein is labeled with a detectable label and the bait protein is tagged with a tag that allows separation of the bait protein and protein(s) interacting with the bait protein from other proteins in the lysate; (b) immobilizing the tag to one or more inner surface(s) of a well, thereby immobilizing the bait protein and protein(s) interacting with the bait protein; and (c) detecting immobilized prey protein by detecting the detectable label, thereby detecting a protein-protein interaction. In some embodiments, the method further comprises detecting immobilized bait protein. In some embodiments, the method comprises In some aspects, the invention provides the recognition that binding of a compound, e.g., a small molecule, to a protein that is a chaperone client can reduce the tendency of the client protein to interact with the chaperone and/or with co-chaperone(s). The invention provides methods based at least in part on detecting, e.g., measuring, an alteration in client-chaperone interaction resulting from a small molecule binding to a client protein.

As described herein, a quantitative luminescence-based protein-protein interaction assay was used to measure interaction of the chaperones HSP90β and/or CDC37 with approximately 370 kinases in the human genome. The results revealed that the majority of human kinases are HSP90β client proteins. Without wishing to be bound by any theory, it is proposed that the intrinsic stability of the kinase domain, rather than any specific sequence motifs, could largely account for HSP90β binding. It was observed that inhibiting the kinase activity of a number of different kinases, using a variety of different small molecule kinase inhibitors, decreases interaction between HSP90β and the target kinase. Furthermore, the decrease in kinase interaction with HSP90β resulting from interaction of the kinase with a small molecule can be quantitatively measured. Similar results were obtained with regard to CDC37-kinase interaction in the presence or absence of small molecule kinase inhibitors. In some aspects of the invention such measurements are used to identify and/or characterize kinase inhibitors. In some aspects of the invention such measurements are used to assess kinase inhibitor specificity.

In some aspects, the invention relates to the discovery that alteration in chaperone-client interaction resulting from binding of a small molecule to a client can be measured. Such measurement(s) can be used for a variety of purposes. In some aspects, the invention provides methods based at least in part on detecting an alteration (e.g., an increase or decrease) in a chaperone-client interaction as compared with a suitable reference value, e.g., a control value. The alteration may result from a variety of different factors such as presence of a small molecule that binds to the client protein, activation of signaling pathways that lead to post-translational modification of a client protein, alterations in amino acid sequence of a client protein, etc.

In some aspects, the invention provides a method of identifying a candidate modulator of a protein of interest, the method comprising: (a) providing a chaperone, a test agent, and a protein of interest, wherein the protein of interest is a client of the chaperone; (b) assessing a protein-protein interaction between the protein of interest and the chaperone in the presence of the test agent, wherein if the interaction between the protein of interest and the chaperone is reduced in the presence of the test agent as compared with the interaction between the chaperone and the protein of interest in the absence of the test compound, the test compound is identified as a candidate modulator of the protein of interest. In some embodiments, a chaperone is an HSP90A or CDC37. In some embodiments, a client is a kinase, e.g., a protein kinase. In some embodiments, a test agent is a kinase inhibitor or a compound being assessed for potential as a kinase inhibitor. In some embodiments, the test agent is a small molecule. In some embodiments, the chaperone and client are expressed by cells. In some embodiments, the test agent is present in cell culture medium. In some embodiments, the chaperone and client are labeled. In some embodiments, a protein-protein interaction between the client and chaperone is measured using a quantitative protein-protein interaction assay which, in some embodiments, employs luminescence to detect bait or prey protein.

In some embodiments, chaperone interaction assays of the invention can be used to (i) identify and/or characterize compounds that bind to a particular client of interest; (ii) identify and/or characterize agents, conditions, or amino acid sequence changes that alter (e.g., increase or decrease) binding of a compound to a client protein; (iii) characterize a compound with regard to its ability to bind to a client protein; (iv) characterize a client protein with regard to its sensitivity or resistance to inhibition by small molecule. In some embodiments, the invention provides methods of profiling compounds with regard to their ability to modulate, e.g., to inhibit, a plurality of client proteins. In some embodiments, a chaperone is an HSP90A protein, and a client protein is a kinase.

In some aspects, the invention provides a method for detecting a protein-protein interaction, the method comprising steps of: (a) providing a lysate prepared from cells that express a prey protein and a bait protein, wherein the prey protein is labeled with a detectable label and the bait protein is tagged with a tag that allows separation of the bait protein and protein(s) interacting with the bait protein from other proteins in the lysate; (b) immobilizing the tag to one or more inner surface(s) of a well, thereby immobilizing the bait protein and protein(s) interacting with the bait protein; (c) detecting immobilized prey protein by detecting the detectable label, thereby detecting a protein-protein interaction. In some embodiments the method further comprises detecting immobilized bait protein. In some embodiments the method further comprises measuring the amount of bait protein, prey protein, or both. In some embodiments the method further comprises measuring the protein-protein interaction. In some embodiments the method further comprises measuring the protein-protein interaction based on the ratio of prey protein to bait protein detected. In some embodiments the cells are vertebrate cells, e.g., mammalian cells, e.g., human cells. In some embodiments the cells stably express the prey protein. In some embodiments the cells are transiently transfected with an expression vector that causes them to express the bait protein. In some embodiments the method comprises removing non-immobilized proteins from the well prior to step (c). In some embodiments the immobilized prey protein and bait protein are detected without removing them from the well. In some embodiments the detectable label comprises a fluorescent, luminescent, or enzymatic label, e.g., a luciferase protein, e.g., *Renilla* or *Gaussia* luciferase. In some embodiments the tag comprises a FLAG, HA, Myc, or 6xHis peptide. In some embodiments the immobilized prey protein is detected by detecting the tag. In some embodiments the one or more inner surface(s) of the well has a binding agent attached thereto that binds to the tag to immobilize the prey protein. In some embodiments the one or more inner surface(s) of the well has a binding agent attached thereto that binds to the tag to immobilize the prey protein, wherein the binding agent comprises an antibody. In some embodiments the bait protein and the prey protein comprise mammalian proteins, e.g., human proteins. In some embodiments the bait protein comprises a receptor, transcription factor, mitochondrial protein imported from the cytoplasm, calcineurin, heat shock factor 1 (HSF1), telomerase reverse transcriptase (TERT), endothelial nitric oxide synthase (eNOS), viral protein, myosin, argonaute, leucine rich repeat (LRR) protein, or kinase. In some embodiments the bait protein comprises a WD40 domain, RCC1 repeat, Kelch domain, WDAD repeat, NHL repeat, or leucine-rich repeat. In some embodiments the bait protein comprises a protein encoded by a proto-oncogene. In some embodiments the bait protein has an alteration in its sequence relative to a wild type protein. In some embodiments the prey protein comprises a chaperone. In some embodiments the prey protein comprises an HSP, e.g., an HSP90 or HSP70. In some embodiments the prey protein comprises an HSP co-chaperone, e.g., HSP90 co-chaperone. In some embodiments the prey protein comprises an HSP90 or CDC37 protein. In some embodiments the prey protein comprises an NUDC domain. In some embodiments the prey protein comprises a chaperone and the bait protein comprises a kinase. In some embodiments of the lysate is prepared from cells that have been contacted with a test agent, e.g., a small molecule. In some embodiments the lysate is prepared from cells that express a single prey protein and a single bait protein. In some embodiments the method is performed in a high throughput format.

In some aspects, the invention provides a method of assessing the effect of a test agent on a protein-protein interaction between a bait protein and a prey protein, the method comprising steps of: (a) measuring a protein-protein interaction between a bait protein and a prey protein according to any of the methods described above (or elsewhere herein), wherein the lysate has been prepared from cells that have been exposed to a test agent; and (b) comparing the result of step (a) with a result of measuring a protein-protein interaction between the bait protein and the prey protein in the absence of the test agent, wherein if the results differ, the test agent modulates the protein-protein interaction, while if the results do not differ, the test agent does not modulate the protein-protein interaction. In some embodiments if the result of step (a) is greater than the result obtained in the absence of the test agent, the test agent increases the protein-protein interaction. In some embodiments if the result of step (a) is less than the result obtained in the absence of the test agent, the test agent inhibits the protein-protein interaction. In some embodiments the prey protein or the bait protein comprises any prey protein or bait protein described above (or elsewhere herein). In some embodiments the prey protein and the bait protein are a chaperone-client pair. In some embodiments the prey protein and the bait protein are a chaperone-client pair, and the method further comprises identifying the test agent as a candidate modulator of the client if the result of step (a) is less than the result obtained in the absence of the test agent. In some embodiments the prey protein and the bait protein are a chaperone-client pair, wherein the client comprises a kinase, and wherein the method further comprises identifying the test agent as a candidate inhibitor of the kinase if the result of step (a) is less than the result obtained in the absence of the test agent. In some embodiments the prey protein and the bait protein are an enzyme-substrate pair. In some embodiments the prey protein and the bait protein are subunits of a protein complex. In some embodiments the test agent is a small molecule. In some embodiments the test agent is an approved drug. In some embodiments a method is performed using a high throughput system capable of testing at least 10,000 test agents per day. In some embodiments a method of characterizing a test agent comprises performing a method of this aspect multiple times using the same prey protein, the same test agent, and different bait proteins, thereby obtaining a profile of the effect of the test agent on multiple bait proteins. In some embodiments the bait proteins comprise a set of proteins that are participate in protein-protein interactions with the prey protein in the absence of the test agent. In some embodiments the prey protein comprises a chaperone protein, and at least some of the bait proteins are clients of the chaperone protein. In some embodiments the prey protein comprises an HSP90 protein or an HSP90 co-chaperone, and the bait proteins comprise HSP90 clients. In some embodiments the prey protein comprises an HSP90 protein or an HSP90 co-chaperone, and the bait proteins comprise kinases. In some embodiments the prey protein comprises a mammalian HSP90 protein or CDC37 protein, and the bait proteins comprise mammalian kinases. In some embodiments the at least 50 different bait proteins are tested in parallel.

In some aspects, the invention provides method of identifying a candidate modulator of a protein of interest, the method comprising: (a) providing a composition comprising a chaperone, a test agent, and a protein of interest, wherein the protein of interest is a client of the chaperone; (b) assessing a protein-protein interaction between the protein of interest and the chaperone in the presence of the test agent, wherein if the interaction between the protein of interest and the chaperone is reduced in the presence of the test compound as compared with the interaction between the chaperone and the protein of interest in the absence of the test compound, the test compound is identified as a candidate modulator of the protein of interest. In some embodiments the protein of interest comprises a receptor, transcription factor, mitochondrial protein imported from the cytoplasm, calcineurin, heat shock factor 1 (HSF1), telomerase reverse transcriptase (TERT), endothelial nitric oxide synthase (eNOS), viral protein, myosin, argonaute, leucine rich repeat (LRR) protein, or kinase. In some embodiments the protein of interest comprises a kinase. In some embodiments the protein of interest comprises a nuclear receptor. In some embodiments the chaperone comprises an HSP (e.g., HSP90 or HSP70) or an HSP co-chaperone. In some embodiments the protein of interest comprises a kinase and the test agent is a known kinase inhibitor. In some embodiments step (a) comprises (i) providing a cell that expresses the chaperone and the protein of interest; and (ii) contacting the cell with the test agent. In some embodiments step (a) comprises (i) providing a cell that stably expresses the chaperone and transiently expresses the protein of interest; and (ii) contacting the cell with the test agent. In some embodiments the cell is a mammalian cell, e.g., a human cell. In some embodiments the method comprises assessing interaction between each of multiple proteins of interest and the chaperone in the presence of the test agent, wherein each of the proteins is contacted with the test agent and the chaperone in a different well. In some embodiments the proteins of interest are kinases. In some embodiments the proteins of interest comprise nuclear receptors. In some embodiments the method is performed a high throughput format.

In some aspects the invention provides a composition comprising a chaperone, a client of the chaperone, and a test agent, wherein the chaperone is labeled with a detectable label and the client is tagged with a tag. In some embodiments the client is a kinase, and the chaperone comprises an HSP90 or CDC37 protein. In some embodiments the client is a kinase, the chaperone comprises an HSP90 or CDC37 protein, and the test agent is a known kinase inhibitor. In some embodiments the client comprises a nuclear receptor, and the chaperone comprises an HSP protein, e.g., HSP90 or HSP70. In some embodiments the composition comprises cells that express the chaperone and the client. In some embodiments the composition comprises mammalian cells, e.g., human cells, that express the chaperone and the protein of interest. In some embodiments the composition comprises a lysate prepared from cells that express the chaperone and the client.

In some aspects the invention provides a cell that expresses a chaperone and a client of the chaperone, wherein the chaperone is labeled with a detectable label and the client is tagged with a tag. In some embodiments the chaperone comprises an HSP90A or CDC37 protein and the client is a kinase. In some embodiments the client comprises a ligand-dependent transcription factor. In some embodiments the client comprises a receptor. In some embodiments the client comprises a nuclear receptor. In some embodiments the chaperone comprises an HSP protein and the client comprises a nuclear receptor. In some embodiments the chaperone comprises an HSP protein and the client comprises a ligand-dependent transcription factor. In some embodiments the cell is a mammalian cell, e.g., a human cell. In some embodiments a panel of cells as set forth above (or elsewhere herein) is provided, wherein members of the panel comprise different clients of a chaperone. In some embodiments a panel of cell lines, cell cultures, cell samples composed of such cells is provided. In some embodiments the members of the panel comprise at least 5 different clients of a chaperone. In some embodiments the cells, cell cultures, cell samples, are in individual vessels, e.g., wells of a multiwell plate. In some embodiments compositions comprising the cells, cell cultures, cell samples, or cell lines, and a test agent are provided.

In some aspects the invention provides a method of identifying a candidate kinase inhibitor comprising: (a) providing a composition comprising a test agent, a chaperone, and a kinase client of the chaperone; (b) measuring interaction between the chaperone and the kinase, wherein if the level of interaction between the chaperone and the kinase is reduced as compared with the level of interaction that would be expected in the absence of the test agent, the test agent is identified as a candidate kinase inhibitor. In some embodiments the chaperone comprises an HSP90A or CDC37 protein. In some embodiments the kinase is associated with a disease. In some embodiments the test agent is a small molecule. In some embodiments, if the level of interaction between the chaperone and the kinase is reduced as compared with the level of interaction that would be expected in the absence of the test agent, the test agent is identified as a candidate inhibitor of the kinase. In some embodiments the method further comprises testing the ability of a candidate kinase inhibitor identified in step (b) to inhibit the kinase using a different assay type. In some embodiments the method is performed in a high throughput format.

In some aspects the invention provides a method of characterizing a compound, the method comprising: (a) providing a composition that comprises a compound, a chaperone, and a kinase client of the chaperone; (b) measuring the interaction between the chaperone and the kinase in the composition; and (c) comparing the level of interaction measured in step (b) with the level of interaction expected in the absence of the compound. In some embodiments the method comprises performing steps (a)-(c) using a plurality of compositions, each of which comprises a different kinase client of the chaperone. In some embodiments the method comprises performing steps (a)-(c) using at least 10 compositions, each of which comprises a different kinase client of the chaperone. In some embodiments the method comprises performing steps (a)-(c) using at least 100 compositions, each of which comprises a different kinase client of the chaperone. In some embodiments the compound is a known kinase inhibitor. In some embodiments the chaperone comprises a HSP90A or CDC37 protein. In some embodiments, the level of interaction is measured using a quantitative luminescence-based protein-protein interaction assay. In some embodiments the level of interaction is measured in a high throughput format.

In some aspects the invention provides a method of characterizing a kinase, the method comprising: (a) providing a composition that comprises a compound, a chaperone, and a kinase client of the chaperone; (b) measuring the interaction between the chaperone and the kinase in the composition; and (c) comparing the level of interaction measured in step (b) with the level of interaction expected in the absence of the compound. In some embodiments the method comprises performing steps (a)-(c) using a plurality of compositions, each of which comprises a different compound. In some embodiments the method comprises performing steps (a)-(c) using at least 10 compositions, each of which comprises a different compound. In some embodiments the method comprises performing steps (a)-(c) using at least 100 compositions, each of which comprises a different compound. In some embodiments the compound is a known kinase inhibitor. In some embodiments the chaperone comprises a HSP90 or CDC37 protein. In some embodiments the level of interaction is measured using a quantitative luminescence-based protein-protein interaction assay. In some embodiments the level of interaction is measured in a high throughput format.

In some aspects the invention provides a method of characterizing a compound, the method comprising (a) providing a composition that comprises a compound, a chaperone, and a kinase client of the chaperone; (b) measuring the interaction between the chaperone and the kinase in the composition; and (c) comparing the level of interaction measured in step (b) with the level of interaction expected in the absence of the compound. In some embodiments the composition comprises cells that express the chaperone and kinase clients. In some embodiments the method comprises performing steps (a)-(c) using at least 10, 20, 50, or 100 compositions, each of which comprises a different kinase. In some embodiments the method comprises performing steps (a)-(c) using at least 10, 20, 50, or 100 compositions, each of which comprises a different kinase, wherein the different kinases are mutants of a kinase of interest. In some embodiments the method comprises obtaining a profile of resistance or sensitivity of multiple kinases to the compound. In some embodiments the method comprises obtaining a profile of resistance or sensitivity of multiple kinases to the compound, wherein the multiple kinases include a plurality of mutants of a kinase of interest. In some embodiments the method comprises obtaining a profile of resistance or sensitivity of multiple kinases to the compound, wherein the multiple kinases include a plurality of mutants of a kinase of interest, wherein the kinase of interest contributes to a disease. In some embodiments the method comprises obtaining a profile of resistance or sensitivity of multiple kinases to the compound, wherein the multiple kinases include a plurality of mutants of a kinase of interest, wherein the kinase of interest contributes to a disease and wherein at least some of the mutants are resistant to a kinase inhibitor used to treat the disease. In some embodiments the method is performed in a high throughput format. In some embodiments the disease is cancer.

In some aspects, the invention provides a method of identifying a candidate modulator of a protein of interest, the method comprising: (a) providing a composition comprising a test agent, a chaperone, and a protein of interest that is a client of the chaperone; (b) measuring interaction between the chaperone and the protein of interest, wherein if the level of interaction between the chaperone and the protein of interest is reduced as compared with the level of interaction that would be expected in the absence of the test agent, the test agent is identified as a candidate modulator of the protein of interest. In some embodiments the composition comprises cells that express the chaperone and the client. In some embodiments the chaperone comprises an HSP or CDC37 protein. In some embodiments the protein of interest is associated with a disease. In some embodiments the protein of interest comprises a kinase. In some embodiments the protein of interest comprises a ligand-dependent transcription factor. In some embodiments the protein of interest comprises a nuclear receptor. In some embodiments the test agent is a small molecule. In some embodiments if the level of interaction between the chaperone and the protein of interest is reduced as compared with the level of interaction that would be expected in the absence of the test agent, the test agent is identified as a candidate modulator of the protein of interest. In some embodiments the method is performed in a high throughput format. In some embodiments the method further comprises testing the ability of a candidate modulator identified in step (b) to modulate the protein of interest using a different assay type.

In some aspects, the invention provides a method of characterizing an agent, the method comprising: (a) providing a composition comprising an agent, a chaperone, and a protein of interest that is a client of the chaperone; (b) measuring interaction between the chaperone and the protein of interest in the composition. In some embodiments the composition comprises cells that express the chaperone and the protein of interest. In some embodiments the chaperone comprises an HSP or CDC37 protein. In some embodiments the protein of interest is associated with a disease. In some embodiments the agent is a small molecule. In some embodiments the method comprises using multiple different concentrations of the agent. In some embodiments if the level of interaction between the chaperone and the protein of interest is reduced as compared with the level of interaction that would be expected in the absence of the agent, the agent is identified as a candidate modulator of the protein of interest. In some embodiments the method further comprises testing the ability of a candidate modulator identified in step (b) to modulate the protein of interest using a different assay type. In some embodiments the method comprises testing the ability of each of a plurality of agents to modulate the protein of interest. In some embodiments the method the method comprises performing steps (a)-(c) using at least 10 compositions, each of which comprises a different client of the chaperone. In some embodiments the method compound is a known modulator of the client. In some embodiments the method chaperone comprises a HSP or CDC37 protein. In some embodiments the level of interaction is measured using a quantitative luminescence-based protein-protein interaction assay. In some embodiments the level of interaction is measured in a high throughput format. In some embodiments the protein comprises a kinase. In some embodiments the protein comprises a ligand-dependent transcription factor. In some embodiments the protein comprises a nuclear receptor.

In some aspects the invention provides a method of characterizing an agent, the method comprising: (a) providing a composition that comprises an agent, a chaperone, and a protein that is a client of the chaperone; (b) measuring the interaction between the chaperone and the client in the composition; and (c) comparing the level of interaction measured in step (b) with the level of interaction expected in the absence of the agent. In some embodiments the composition comprises cells that express the chaperone and client. In some embodiments the method comprises performing steps (a)-(c) using a plurality of compositions, each of which comprises a different client of the chaperone. In some embodiments the method comprises performing steps (a)-(c) using at least 10 compositions, each of which comprises a different client of the chaperone. In some embodiments the compound is a known modulator of the client. In some embodiments the chaperone comprises a HSP or CDC37 protein. In some embodiments the level of interaction is measured using a quantitative luminescence-based protein-protein interaction assay. In some embodiments the level of interaction is measured in a high throughput format. In some embodiments the agent is a small molecule. In some embodiments the method comprises using multiple different concentrations of the agent. In some embodiments the client protein comprises a kinase. In some embodiments the client protein comprises a ligand-dependent transcription factor. In some embodiments the client protein comprises a nuclear receptor.

In some aspects methods of inhibiting a kinase are provided. In some embodiments a method of inhibiting a kinase comprises the step of: contacting the kinase with GNF-2, PLX4032, PLX4720, crizotinib, or GDC-0879, wherein the kinase is a newly identified target of GNF-2, PLX4032, PLX4720, crizotinib, or GDC-0879, respectively, listed in Table 2. In some embodiments a method of inhibiting a kinase comprises contacting the kinase with a structural analog of GNF-2, PLX4032, PLX4720, crizotinib, or GDC-0879, wherein the kinase is a newly identified target of GNF-2, PLX4032, PLX4720, crizotinib, or GDC-0879, respectively, listed in Table 2.

In some aspects methods of treating a disease (disorder) are provided. In some embodiments a method of treating a disorder associated with aberrant activity of a newly identified target of GNF-2, PLX4032, PLX4720, crizotinib, or GDC-0879 listed in Table 2 comprises administering GNF-2, PLX4032, PLX4720, crizotinib, or GDC-0879, or a structural analog thereof, to a subject in need of treatment for the disorder. In some embodiments a newly identified target comprises NTRK3 and the method comprises administering crizotinib or a structural analog thereof to the subject. In some embodiments a newly identified target comprises RIPK1 and the method comprises administering PLX4032, crizotinib, or a structural analog of PLX4032 or crizotinib to the subject. In some embodiments the subject is human.

Certain conventional techniques of cell biology, cell culture, molecular biology, microbiology, recombinant nucleic acid (e.g., DNA) technology, immunology, etc., which are within the skill of the art, may be of use in aspects of the invention. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., editions as of 2008; Sambrook, Russell, and Sambrook, *Molecular Cloning: A Laboratory Manual*, 3$^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Burns, R., *Immunochemical Protocols* (Methods in Molecular Biology) Humana Press; 3rd ed., 2005. Further information on cancer may be found in Cancer: Principles and Practice of Oncology (V. T. De Vita et al., eds., J.B. Lippincott Company, 7th ed., 2004 or 8th ed., 2008) and Weinberg, R A, The Biology of Cancer, Garland Science, 2006. All patents, patent applications, books, other publications, databases, and websites mentioned herein are incorporated herein by reference in their entirety. In the event of a conflict or inconsistency with the specification, the specification shall control. The Applicants reserve the right to amend the specification based on any of the incorporated references and/or to correct obvious errors. None of the contents of the incorporated references shall limit the invention.

BRIEF DESCRIPTION OF THE DRAWINGS

FIG. 2 illustrates that HSP90β interacts with diverse kinases among all major protein kinase families.

FIG. 11 lists chaperones and co-chaperones (columns labeled "TPR domains", "p23", and "Others") whose pairwise interaction was tested in order to develop a quantitative map reflecting a network of chaperone/co-chaperone interactions.

DETAILED DESCRIPTION OF CERTAIN EMBODIMENTS

I. Terms

Figure 1:
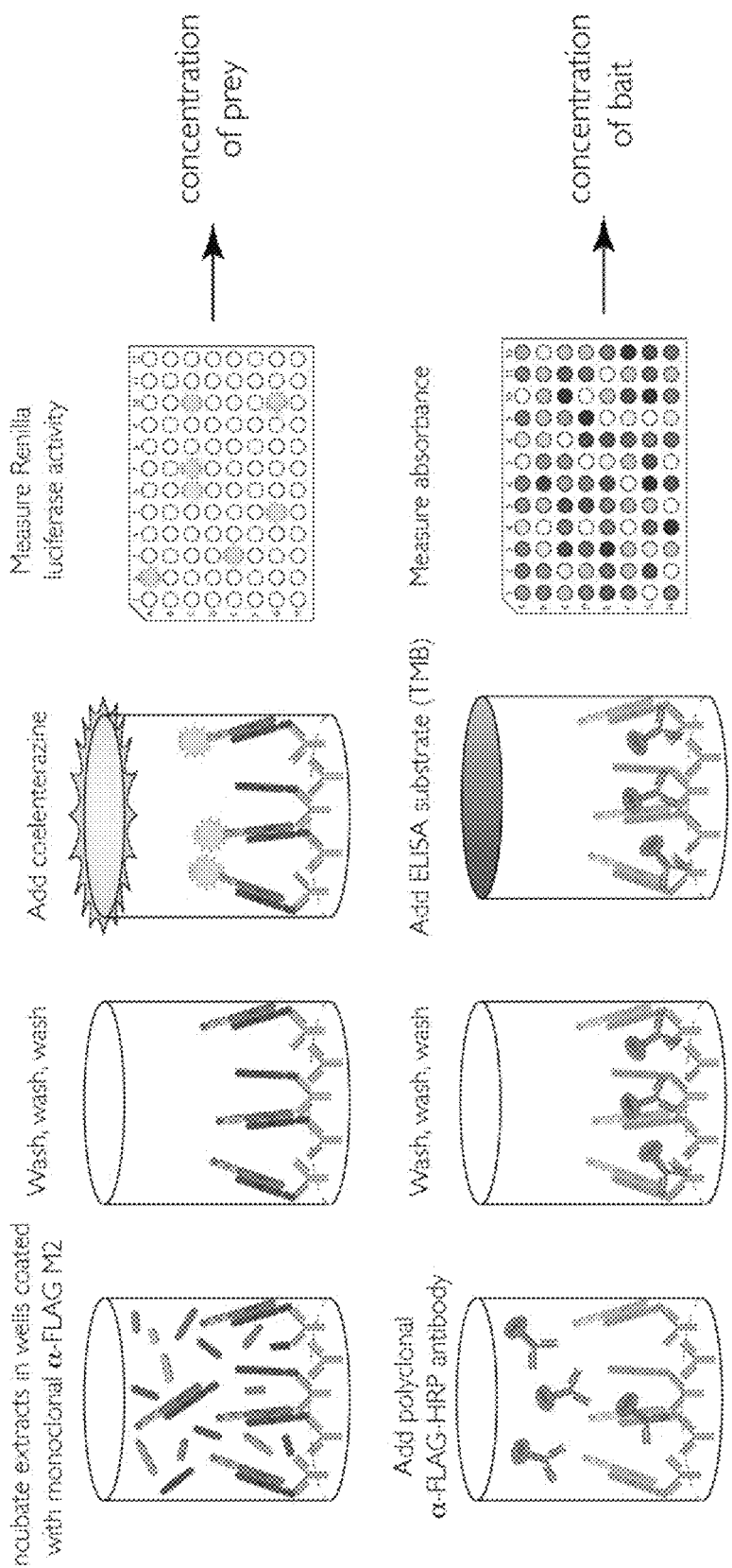
FIG. 1. (A) Schematic diagram showing an inventive assay for detecting interaction between a bait protein and a prey protein. (1) Cells are transfected with a first construct that encodes a bait protein tagged with an epitope tag (3×FLAG tag) and contain a second construct that encodes a prey protein tagged with a detectable protein (*Renilla* luciferase); (2) Extracts are prepared from the transfected cells and incubated in wells coated with antibody that binds to the tag, thus capturing bait protein and bait-prey complexes; (3) Extract is removed, and immunoprecipitates are washed; (4) Luciferase substrate is added; (5) Bait protein is detected and quantitated by measuring fluorescence; (6) Anti-FLAG antibody is added to wells, followed by washing (7) to remove unbound antibody; (8) HRP substrate is added to wells; (9) Prey is detected and quantitated by measuring absorbance. The ratio of prey protein to bait protein measured indicates the bait-prey stoichiometry (corresponding to strength of the interaction). (B) Schematic diagrams of a bait protein tagged with a 3×FLAG epitope tag and an Hsp90β prey protein tagged with *Renilla* luciferase. (C) Western blot showing expression of *Renilla*-tagged Hsp90β in stable cell line (right) but not in untransfected control cells (left). Blots were probed using antibody against Hsp903 (upper panel) or against *Renilla* luciferase (lower panel). Expression of native Hsp90β is evident in both transfected and untransfected cells.

"Antibody" refers to an immunoglobulin, whether natural or wholly or partially synthetically produced. An antibody may be a member of any immunoglobulin class, including any of the mammalian, e.g., human, classes: IgG, IgM, IgA, IgD, and IgE, or subclasses thereof, and may be an antibody fragment, in various embodiments of the invention. As used herein, the term "antibody fragment" refers to a derivative of an antibody which contains less than a complete antibody. In general, an antibody fragment retains at least a significant portion of the full-length antibody's specific binding ability. Examples of antibody fragments include, but are not limited to, Fab, Fab', F(ab')2, scFv, Fv, dsFv diabody, Fd fragments, and domain antibodies. Standard methods of antibody identification and production known in the art can be used to produce an antibody that binds to a polypeptide of interest, e.g., a label. In some embodiments, an antibody is a monoclonal antibody. Monoclonal antibodies can be identified and produced, e.g., using hybridoma technology or recombinant nucleic acid technology (e.g., phage or yeast display). An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may comprise a single chain antibody fragment. Alternatively or additionally, an antibody fragment may comprise multiple chains which are linked together, for example, by disulfide linkages. A functional antibody fragment typically comprises at least about 50 amino acids and more typically comprises at least about 100, e.g., about 200 amino acids. For example, an antibody fragment typically contains at least 1, 2, or 3 complementarity determining domains (CDRs) (VL CDR1, CDR2, CDR3; VH CDR1, CDR2, CDR3) of the antibody, optionally joined by one or more framework region(s). Certain antibodies, e.g., recombinantly produced antibodies, can comprise heterologous sequences not derived from naturally occurring antibodies. For example, single-chain variable fragments (scFv) are typically fusion protein containing the variable regions of the heavy (VH) and light chains (VL) of immunoglobulins, connected with a short linker peptide of ten to about 25 amino acids. Other heterologous sequences, such as polypeptide labels, can be present. An antibody may be labeled with a small molecule, e.g., a fluorescent dye, biotin, etc.

The terms "bait protein" and "prey protein" refer to proteins that are to be tested for interaction with each other (or are being or have been tested for interaction with each other) and/or whose interaction with each other is to be assessed (or is being or has been assessed).

The term "chaperone" refers to a protein that assists in the folding of a protein or assembly of a complex (e.g., a protein-containing complex) but typically does not otherwise contribute to the final structure or function of the product. The term "core chaperone" refers to HSP40, HSP70, HSP90 family members. Lists of human HSP40, HSP70, HSP90, and various other chaperone genes and proteins and corresponding Gene IDs for the human genes and mouse orthologs is found in Kampinga H H, et al. Guidelines for the nomenclature of the human heat shock proteins. Cell Stress Chaperones. 14:105-111, 2009, which describes a proposed nomenclature system for HSPs and provides listings of alternate names. As known in the art, the GeneID is a unique identifier in the Gene database (www.ncbi.nim.nih.gov/gene), assigned by the NCBI (National Center for Biotechnology Information) that provides, among other things, a link to sequence information for the gene, mRNA, and encoded protein, thereby allowing those of ordinary skill in the art to readily obtain such information. The term "co-chaperone" refers to a protein that associates with and promotes the function of one or more core chaperone(s) by, e.g., modulating the chaperoning activity and/or regulating the substrate specificity of the core chaperone(s). Some co-chaperones have chaperoning activity even when they are not associated with the core chaperones, and the designation of a particular protein as a co-chaperone rather than a chaperone may be based on common usage in the art. As used herein, "chaperone" encompasses core chaperones and co-chaperones.

The term "client" or "client protein" refers to a protein that physically interacts with a chaperone and whose folding or assembly into a complex is assisted by the chaperone. The protein is said to be a "client" of the chaperone. If desired, confirmation that a particular protein that interacts with a chaperone is a client of the chaperone may be obtained by showing that inhibition or loss of the function of the chaperone results in a lower level of client activity. Inhibition of the function of the chaperone may be achieved in a variety of ways. For example, expression of the chaperone can be inhibited (e.g., using RNA interference, gene knockout) or chaperone activity can be reduced using approaches such as small molecule inhibitors, aptamers, intrabodies, expression of dominant negative versions, etc.

The terms "interact", "interaction", and similar terms refer to a physical association between two or more entities such as proteins, nucleic acids, small molecules, etc. For example, a protein-protein interaction is a physical interaction involving two or more proteins. In general, an interaction can be "direct" (i.e., the entities are in physical contact with each other) or "indirect" (i.e., via one or more intervening entities). Entities that participate or are capable of participating in an interaction may be referred to as "partners" or "interaction partners" herein. Often an interaction of interest herein is a noncovalent association, which may result from factors such as electrostatic forces, hydrophobic effect, ionic and/or hydrogen bonds, and complementarity of shape between the interaction partners. Typically, an interaction of interest herein is one that occurs under at least some physiological conditions (e.g., conditions that exist within cells that contain the interaction partners). In many embodiments of interest herein, an interaction occurs intracellularly, between proteins that are synthesized by a cell. In some embodiments, a protein-protein interaction may be stimulated or inhibited as a result of post-translational modification(s) of one or more of the partners (or potential partners).

"Isolated" refers to a substance that is (i) separated from at least some other substances with which it is normally found in nature, usually by a process involving the hand of man, (ii) artificially produced (e.g., chemically synthesized), and/or (iii) present in an artificial environment or context (i.e., an environment or context in which it is not normally found in nature). In some aspects, "isolated" refers to separation of bait protein, prey protein, and/or bait-prey complexes from many or most non-bait, non-prey proteins present in a lysate.

"Modulator" refers to an agent or condition that alters, e.g., inhibits (reduces, decreases) or enhances (activates, stimulates, increases), a process, pathway, phenomenon, state, or activity. For example, a modulator of a protein-protein interaction may increase or decrease the strength of the interaction. A modulator of protein activity may increase or decrease the level of one or more activit(ies) of a protein, e.g., enzymatic activity. Enzymatic activity refers to ability to catalyze one or more chemical reactions. In accordance with common practice in the art, an enzyme is considered to carry out or perform the particular reaction(s) that it catalyzes (for example, a kinase is considered to phosphorylate a substrate whose phosphorylation it catalyzes).

"Panel" refers to a collection or set of entities, e.g., a collection or set of molecules, cells, or cell lines. For example, a "kinase panel" is a collection or set of kinase proteins. A "kinase inhibitor panel" is a collection or set of kinase inhibitors. The individual entities are said to be "members" of the panel. Often, the members of a panel are related to one another in some way, e.g., they have one or more functional and/or structural characteristics in common and/or they are to be tested or used in a particular assay.

"Polypeptide" refers to a polymer of amino acids. The terms "protein", "polypeptide", and "peptide" are used interchangeably herein although it will be understood that certain proteins may comprise two or more polypeptide chains and "peptide" often refers to a relatively short polypeptide, typically between about 2 and 60 amino acids in length. Polypeptides used herein typically contain the standard amino acids (i.e., the 20 L-amino acids that are most commonly found in proteins). However, a polypeptide can contain one or more non-standard amino acids (which may be naturally occurring or non-naturally occurring) and/or amino acid analogs known in the art in certain embodiments. One or more of the amino acids in a polypeptide may be modified, for example, by the addition of a chemical entity such as a carbohydrate group, a phosphate group, a fatty acid group, a linker for conjugation, functionalization, etc. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated. The invention encompasses embodiments that relate to isoforms of polypeptides of interest herein (e.g., polypeptides arising from the same gene that differ in sequence as a result of alternative splicing or editing of mRNA or as a result of different alleles of a gene, e.g., alleles differing by one or more single nucleotide polymorphisms (typically such alleles will be at least 95%, 96%, 97%, 98%, 99%, or more identical to a reference or consensus sequence).

"Profile" refers to a collection of information regarding an entity or entit(ies). For example, a profile may represent the extent to which an entity or entit(ies) exhibit(s) various characteristics or activities of interest. A profile of a compound ("compound profile") may include information regarding the extent to which the compound binds to or affects the activity of each of a plurality of proteins (e.g., as determined using a particular assay). A profile of a protein may include information regarding the extent to which it is bound by each of a plurality of compounds and/or the extent to which an activity of the protein is modulated (e.g., inhibited or activated) by each of a plurality of compounds. In some embodiments, a profile includes quantitative information (e.g., measurements of a characteristic or activity of interest). Profiles may be presented or displayed in any of variety of formats, e.g., lists, tables, graphs, charts, plots, heatmaps, dendrograms, etc. "Profiling" refers to the process of acquiring the information (e.g., by performing one or more assays) and, optionally, processing and/or analyzing the information acquired.

"Purified" refers to agents or entities (e.g., compounds) that have been separated from most of the components with which they are associated in nature or when originally generated. In general, such purification involves action of the hand of man. Purified agents or entities may be partially purified, substantially purified, or pure. Such agents or entities may be, for example, at least 50%, 60%, 70%, 75%, 80%, 85%, 90%, 95%, 96%, 97%, 98%, 99%, or more than 99% pure. In some embodiments, a nucleic acid or polypeptide is purified such that it constitutes at least 75%, 80%, 85%, 90%, 95%, 96%, 97%, 98%, 99%, or more, of the total nucleic acid or polypeptide material, respectively, present in a preparation. Purity can be based on, e.g., dry weight, size of peaks on a chromatography tracing, molecular abundance, intensity of bands on a gel, or intensity of any signal that correlates with molecular abundance, or any art-accepted quantification method. In some embodiments, water, buffers, ions, and/or small molecules (e.g., precursors such as nucleotides or amino acids), can optionally be present in a purified preparation. A purified molecule may be prepared by separating it from other substances (e.g., other cellular materials), or by producing it in such a manner to achieve a desired degree of purity. In some embodiments, a purified molecule or composition refers to a molecule or composition that is prepared using any art-accepted method of purification. In some embodiments "partially purified" means that a molecule produced by a cell is no longer present within the cell, e.g., the cell has been lysed and the molecule has been separated or segregated from at least some molecules of the same type (protein, RNA, DNA, etc.) that were present in the lysate.

A "small molecule" as used herein, is an organic molecule that is less than about 2 kilodaltons (KDa) in mass. In some embodiments, a small molecule is less than about 1.5 KDa, or less than about 1 KDa. In some embodiments, a small molecule is less than about 800 daltons (Da), 600 Da, 500 Da, 400 Da, 300 Da, 200 Da, or 100 Da. Often, a small molecule has a mass of at least 50 Da. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

"Selectivity" is used interchangeably with "specificity" herein to describe the tendency of an agent (e.g., a small molecule) to affect certain member(s) of a particular population of interest in preference to others. A population of interest could be e.g., genes, gene products (RNA or proteins), signaling pathways, cells, tissues, diseases, etc. For example a selective kinase inhibitor would have the ability to discriminate between kinases present in a particular environment or under particular conditions (e.g., inside a cell or under conditions of an in vitro assay), and so inhibit the activity of certain kinase(s) to a greater extent than others.

A "subject" can be any multicellular organism, e.g., an animal. Often a subject is a vertebrate, e.g., a mammal or avian. Exemplary mammals include, e.g., humans, non-human primates, rodents (e.g., mouse, rat, rabbit), ungulates (e.g., ovine, bovine, equine, caprine species), canines, and felines. Often, a subject is an individual to whom a compound is to be delivered, e.g., for experimental, diagnostic, and/or therapeutic purposes or from whom a sample is obtained or on whom a diagnostic procedure is performed (e.g., a sample or procedure that will be used to assess whether a subject suffers from a disease and/or to assess the effect of a compound).

"Structural analog" is used consistently with use in the art to refer to a compound having a structure that is similar to that of a first compound, but in which in one or more atoms, functional group(s), and/or substructures present in the first compound is/are replaced with other atoms, groups, or substructures. In some embodiments, two or more compounds are structural analogs of the same initial "hit" identified in a screen and/or the same lead compound. For example, they may be compounds designed by making one or more modifications to the structure of the same hit and/or lead compound. In some embodiments, a structural analog of a compound is based on the same pharmacophore as the compound. In some embodiments, a structural analog of a compound is substantially identical to the compound except that at least one atom or functional group present in the compound is replaced by a different atom or functional group, wherein said different atom or functional group is recognized in the art as being a bioisostere of said atom or functional group.

"Kinase inhibitor" as used herein, refers to an agent, e.g., a small molecule, that binds to a kinase protein and inhibits its kinase activity, i.e., inhibits its ability to catalyze transfer of a phosphate group to substrates. Kinase inhibitors have been classified into four main types. Type I inhibitors are ATP-competitive compounds that recognize and bind to the "active" conformation of the kinase, i.e., the conformation otherwise conducive to phosphotransfer. Type II inhibitors recognize and bind to the inactive conformation of the kinase. Type III inhibitors (also termed "allosteric" inhibitors) bind outside the ATP binding site at an allosteric site. Covalent inhibitors are capable of forming a stable covalent bond to the kinase, e.g., to the kinase active site, often by reacting with a nucleophilic cysteine residue.

The terms "tag" and "label" are used interchangeably herein to refer to an entity that is attached or can be attached to a second entity and when so attached can be used to detect the second entity and/or to separate the second entity from one or more other entit(ies) with which the second entity is associated. The second entity to which the tag or label is attached is said to be "tagged" or "labeled". In the context of the present invention, the second entity is typically a polypeptide (e.g., a bait or prey protein), the tag or label often comprises a peptide or polypeptide, and the tag or label and the second entity are often portions of a recombinant protein, e.g., a fusion protein, encoded by a recombinant nucleic acid. A protein can comprise multiple tags or labels which may be separated from each other and/or from other portion(s) of the protein by linker(s). In many embodiments, a prey protein is fused to a detectable label and a prey protein is fused to an epitope tag.

"Fusion protein" encompasses proteins that contain two or more different polypeptide sequences that are not found joined to one another in nature. Such proteins may be generated through translation of a nucleic acid sequence arising through the joining of two or more nucleic acid sequences that originally coded for separate proteins or portions thereof. Optionally a fusion protein comprises a linker sequence (also sometimes referred to as a spacer sequence) between the two polypeptide sequences. Non-limiting examples of linker sequences include sequences containing multiple Gly and/or Ser residues. For example, a linker sequence could be up to about 50 amino acids long, e.g., between 5 and 30 amino acids long, e.g., between 10 and 20 amino acids long, wherein at least 50% of the amino acids are either Gly or Ser residues. A fusion protein can comprise multiple distinct portions that may be separated from each other and/or from other portion(s) of the protein by linker(s).

"Detectable label" is used herein consistent with use in the art to refer to an entity that can be detected, e.g., using optical, electrical, chemical, spectroscopic, biochemical, immunochemical, photochemical, and/or magnetic means. Suitable detectable labels of use in various embodiments of the invention include, but are not limited to, luminescent agents (e.g., bioluminescent or chemiluminescent proteins), fluorescent agents (e.g., fluorescent proteins), enzymes, and affinity tags (e.g., epitope tags). Often, a detectable label is an entity that generates a signal that can be measured and whose intensity is related to the amount of label (e.g., number of molecules) present (e.g., in a sample). A detectable label may be directly detectable (i.e., it can be detected without requiring binding to or reaction with other molecule(s) and/or it may be indirectly detectable (i.e., it is made detectable through interaction with (e.g., reaction or binding to) another entity that is detectable (either directly or indirectly). For example, a fluorescent or radioactive substance is generally directly detectable. Many labels are detectable following interaction with a substrate, e.g., luciferases are detectable based on their catalysis of a reaction that produces light. An epitope tag is often detected following binding of an antibody comprising a directly detectable moiety such as a fluorophore or following binding of an antibody conjugated to an enzyme, wherein the enzyme reacts with a substrate to generate a signal. Epitope tags are often short peptide sequences to which high-affinity antibodies exist (or can be readily produced). In some embodiments, an epitope tag consisting of a sequence that is not present in endogenous proteins expressed by a particular cell type or species (e.g., human cells) is used (for example the genome of the cell may lack sequences encoding the tag or, if present, such sequences are not expressed). Examples of epitope tags include the FLAG, HA, TAP, Myc, V5, and 6×His tags. Sequences of these tags, and suitable antibodies for detecting them and/or isolating proteins labeled with a particular tag, are well known in the art. See, e.g., Einhauer, A., and Jungbauer, A., Journal of Biochemical and Biophysical Methods, 49 (1-3): 455-465, 2001, with regard to the FLAG tag.

Any of a wide variety of fluorescent or luminescent proteins may be used as detectable labels. Such proteins are well known in the art. Fluorescent proteins include, e.g., green fluorescent protein (GFP) from the jellyfish *Aequorea victoria*, related naturally occurring green fluorescent proteins, and related proteins comprising chromophores that emit light of different colors such as red, yellow, and cyan. Many of these proteins are found in diverse marine animals such as *Hydrozoa* and *Anthozoa* species, crustaceans, comb jellies, and lancelets. See, e.g., See, e.g., Chalfie, M. and Kain, S R (eds.) Green fluorescent protein: properties, applications, and protocols (Methods of biochemical analysis, v. 47). Wiley-Interscience, Hoboken, N.J., 2006, which discusses GFP and numerous other fluorescent or luminescent proteins. See also Chudakov, D M, et al., Physiol Rev. 90(3):1103-63, 2010, for further information and references.

In some embodiments, the detectable label comprises a monomeric fluorescent protein. Non-limiting examples of monomeric fluorescent proteins include Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See Chudakov D M (cited above).

In some embodiments, the detectable tag comprises a luciferase. As known in the art, "luciferase" refers to members of a class of enzymes that catalyze reactions that result in production of light. Luciferases are found in a variety of organisms including a variety of marine copepods, beetles, and others, and a number of these proteins have been cloned. Examples of luciferases include, e.g., luciferase from species of the genus *Renilla* (e.g., *Renilla reniformis* (Rluc), or *Renilla mulleri* luciferase), luciferase from species of the genus *Gaussia* (e.g., *Gaussia princeps* luciferase, *Metridia* luciferase from species of the marine copepod *Metridia*, e.g., *Metridia longa*, luciferase from species of the genus *Pleuromamma*, beetle luciferases (e.g. luciferase of the firefly *Photinus pyralis* or of the Brazilian click beetle *Pyrearinus termitilluminans*), etc. As known in the art, a number of luciferases contain signal sequences (sequences that direct secretion of the protein by cells that express it). For example, naturally occurring *Gaussia princeps* luciferase contains a signal sequence and is ordinarily secreted when expressed by mammalian cells. In certain embodiments of the invention in which a luciferase is used as a label for a bait or prey protein and the naturally occurring form of the luciferase contains a signal sequence effective to direct secretion of the luciferase when expressed in cells to be used in an inventive assay (e.g., mammalian cells), the signal sequence may be at least in part removed or modified so that is no longer functional in the cells to be used in the assay. "Luciferin" is used herein to refer to any substrate utilized by a luciferase or photoprotein in a light-emitting reaction. Examples include, e.g., firefly luciferin and coelenterazine. Coelenterazine is the substrate in many luciferases and photoproteins including *Renilla, Gaussia*, and *Metridia* luciferases, and aequorin.

In some embodiments, a fluorescent or luminescent protein or luciferase is an engineered variant of a naturally occurring protein. Such variants may, for example, have increased stability (e.g., increased photostability, increased pH stability), increased fluorescence or light output, reduced tendency to dimerize, oligomerize, or aggregate, an altered absorption/emission spectrum (in the case of a fluorescent protein) and/or an altered substrate utilization. See, e.g., Chalfie, M. and Kain, S R (cited above) for examples. For example, the *A. Victoria* GFP variant known as enhanced GFP (eGFP) may be used. A variant of a naturally occurring luciferase that provides higher light output than the naturally occurring form and/or utilizes a coelentarazine analog as a substrate can be used. See, e.g., Loening, A M, et al., Protein Engineering, Design and Selection (2006) 19 (9): 391-400, for examples with respect to *Renilla* luciferase.

In some embodiments, a nucleic acid sequence encoding a detectable protein (e.g., GFP, luciferase, etc.) is codon-optimized for expression in cells that are to be used in an assay. For example, the sequence may be codon-optimized for expression in mammalian cells, e.g., human cells. See, e.g., Tannous, B A, et al., Mol Ther. 11(3):435-43, 2005 for an example of *Gaussia* luciferase cDNA codon-optimized for expression in mammalian cells.

"Treat", "treating" and similar terms in regard to a treating a subject refer to providing medical and/or surgical management of the subject. Treatment may be undertaken, e.g., to alleviate symptoms, inhibit progression (stabilize) or cause regression of a disease state or condition, cure a disease, etc. Treatment can include, but is not limited to, administering or recommending administration of (e.g., prescribing) a compound or composition (e.g., a pharmaceutical composition) to a subject. Treatment can be undertaken after development of one or more symptoms or signs of a disorder, e.g., after diagnosis of a disorder or diagnosis of a condition in a subject for which there is a need for medical and/or surgical intervention. Treatment can be undertaken prophylactically, e.g., in a subject who is at increased risk of a disorder (or recurrence of a disorder). Increased risk may be based on existence of one or more recognized environmental and/or genetic risk factors. "Disorder" is used interchangeably with "disease" herein and can refer to any condition of impaired health and/or abnormal functioning, e.g., a condition for which treatment is or may be warranted.

A "variant" of a particular polypeptide refers to a polypeptide that differs from such polypeptide (sometimes referred to as the "original polypeptide") by one or more amino acid alterations, e.g., addition(s), deletion(s), and/or substitution(s). Sometimes an original polypeptide is a naturally occurring polypeptide (e.g., from human or non-human animal) or a polypeptide identical thereto. Variants may be naturally occurring or created using, e g., recombinant DNA techniques or chemical synthesis. An addition can be an insertion within the polypeptide or an addition at the N- or C-terminus. In some embodiments, the number of amino acids substituted, deleted, or added can be for example, about 1 to 30, e.g., about 1 to 20, e.g., about 1 to 10, e.g., about 1 to 5, e.g., 1, 2, 3, 4, or 5. In some embodiments, a variant comprises a polypeptide whose sequence is homologous to the sequence of the original polypeptide over at least 50 amino acids, at least 100 amino acids, at least 150 amino acids, or more, up to the full length of the original polypeptide (but is not identical in sequence to the original polypeptide), e.g., the sequence of the variant polypeptide is at least 50%, 60%, 70%, 75%, 80%, 85%, 90%, 95%, 96%, 97%, 98%, 99%, or more identical to the sequence of the original polypeptide over at least 50 amino acids, at least 100 amino acids, at least 150 amino acids, or more, up to the full length of the original polypeptide. In some embodiments, a variant comprises a polypeptide at least 50%, 60%, 70%, 75%, 80%, 85%, 90%, 91%, 92%, 93%, 94%, 95%, 96%, 97%, 98%, 99%, 99.5% or more identical to an original polypeptide over at least 50%, 60%, 70%, 80%, 85%, 90%, 91%, 92%, 93%, 94%, 95%, 96%, 97%, 98%, 99%, or 100% of the length of the original polypeptide.

In some embodiments one, more than one, or all biological functions or activities of a variant or fragment is substantially similar to that of the corresponding biological function or activity of the original molecule. In some embodiments, a functional variant retains at least 10%, 20%, 30%, 40%, 50%, 60%, 70%, 80%, 90%, 95%, 96%, 97%, 98%, 99%, or more of the activity of the original polypeptide, e.g., about equal activity. In some embodiments, the activity of a variant is up to approximately 100%, approximately 125%, or approximately 150% of the activity of the original molecule. In other nonlimiting embodiments an activity of a variant or fragment is considered substantially similar to the activity of the original molecule if the amount or concentration of the variant needed to produce a particular effect is within 0.5 to 5-fold of the amount or concentration of the original molecule needed to produce that effect.

In some embodiments amino acid substitutions in a variant are the result of replacing one amino acid with another amino acid having similar structural and/or chemical properties, i.e., conservative amino acid replacements. "Conservative" amino acid substitutions may be made on the basis of similarity in any of a variety or properties such as side chain size, polarity, charge, solubility, hydrophobicity, hydrophilicity, and/or amphipathicity of the residues involved. For example, the non-polar (hydrophobic) amino acids include alanine, leucine, isoleucine, valine, glycine, proline, phenylalanine, tryptophan and methionine. The polar (hydrophilic), neutral amino acids include serine, threonine, cysteine, tyrosine, asparagine, and glutamine. The positively charged (basic) amino acids include arginine, lysine and histidine. The negatively charged (acidic) amino acids include aspartic acid and glutamic acid. Within a particular group, certain substitutions may be of particular interest, e.g., replacements of leucine by isoleucine (or vice versa), serine by threonine (or vice versa), or alanine by glycine (or vice versa). Non-conservative substitutions are often compatible with retaining function as well. In some embodiments, a substitution or deletion does not alter or delete an amino acid important for activity. Insertions or deletions may range in size from about 1 to 20 amino acids, e.g., 1 to 10 amino acids. In some instances larger domains may be removed without substantially affecting function. In certain embodiments of the invention the sequence of a variant can be obtained by making no more than a total of 5, 10, 15, or 20 amino acid additions, deletions, or substitutions to the sequence of a naturally occurring enzyme. In some embodiments no more than 1%, 5%, 10%, or 20% of the amino acids in a polypeptide are insertions, deletions, or substitutions relative to the original polypeptide. Guidance in determining which amino acid residues may be replaced, added, or deleted without eliminating or substantially reducing activities of interest, may be obtained by comparing the sequence of the particular polypeptide with that of homologous polypeptides (e.g., from other organisms) and minimizing the number of amino acid sequence changes made in regions of high homology (conserved regions) or by replacing amino acids with those found in homologous sequences since amino acid residues that are conserved among various species are more likely to be important for activity than amino acids that are not conserved.

In some embodiments, a variant of a polypeptide comprises a heterologous polypeptide portion. The heterologous portion typically comprises a sequence that is not present in or homologous to the original polypeptide. A heterologous portion may be, e.g., between 5 and about 2,000 amino acids long, or longer. Often it is between 5 and about 1,000 amino acids long, e.g., between 5 and about 200, 300, or 400 amino acids long. In some embodiments, a heterologous portion comprises a sequence that is found in a different polypeptide. In some embodiments, a heterologous portion comprises a sequence useful for purifying, expressing, solubilizing, and/or detecting the polypeptide. In some embodiments, a heterologous portion is appended to the N- or C-terminus or a polypeptide. In some embodiments, a heterologous portion is inserted into a region of the polypeptide that does not contain amino acids critical for function of the polypeptide, such that the insertion does not substantially diminish function of the polypeptide. In some embodiments, a heterologous portion comprises a polypeptide label or tag. In some embodiments, a heterologous portion comprises a peptide linker, wherein the peptide linker serves to separate a functional domain of the heterologous portion from the polypeptide to which it is appended or into which it is inserted. In some embodiments, the appending or insertion of the heterologous portion is the only change in the variant relative to the original sequence. In some embodiments, one or more alterations (e.g., substitution(s), deletion(s) is made in the original sequence.

"Vector" is used herein to refer to a nucleic acid or a virus or portion thereof (e.g., a viral capsid or genome) capable of mediating entry of, e.g., transferring, transporting, etc., a nucleic acid molecule into a cell. Where the vector is a nucleic acid, the nucleic acid molecule to be transferred is generally linked to, e.g., inserted into, the vector nucleic acid molecule. A nucleic acid vector may include sequences that direct autonomous replication (e.g., an origin of replication), or may include sequences sufficient to allow integration of part or all of the nucleic acid into host cell DNA. Useful nucleic acid vectors include, for example, DNA or RNA plasmids, cosmids, and naturally occurring or modified viral genomes or portions thereof or nucleic acids (DNA or RNA) that can be packaged into viral capsids. Plasmid vectors typically include an origin of replication and one or more selectable markers. Plasmids may include part or all of a viral genome (e.g., a viral promoter, enhancer, processing or packaging signals, etc.). Viruses or portions thereof that can be used to introduce nucleic acid molecules into cells are referred to as viral vectors. Useful viral vectors include adenoviruses, adeno-associated viruses, retroviruses, lentiviruses, vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-defective, and such replication-defective viral vectors may be preferable for therapeutic use. Where sufficient information is lacking it may, but need not be, supplied by a host cell or by another vector introduced into the cell. The nucleic acid to be transferred may be incorporated into a naturally occurring or modified viral genome or a portion thereof or may be present within the virus or viral capsid as a separate nucleic acid molecule. It will be appreciated that certain plasmid vectors that include part or all of a viral genome, typically including viral genetic information sufficient to direct transcription of a nucleic acid that can be packaged into a viral capsid and/or sufficient to give rise to a nucleic acid that can be integrated into the host cell genome and/or to give rise to infectious virus, are also sometimes referred to in the art as viral vectors. Vectors may contain one or more nucleic acids encoding a marker suitable for use in the identifying and/or selecting cells that have or have not been transformed or transfected with the vector. Markers include, for example, proteins that increase or decrease either resistance or sensitivity to antibiotics (e.g., an antibiotic-resistance gene encoding a protein that confers resistance to an antibiotic such as puromycin, G418, hygromycin or blasticidin) or other compounds, enzymes whose activities are detectable by assays known in the art (e.g., β-galactosidase or alkaline phosphatase), and proteins or RNAs that detectably affect the phenotype of transformed or transfected cells (e.g., fluorescent proteins). Expression vectors are vectors that include regulatory sequence(s), e.g., expression control sequences such as a promoter, sufficient to direct transcription of an operably linked nucleic acid. Regulatory sequences may also include enhancer sequences or upstream activator sequences. Vectors may optionally include 5' leader or signal sequences. Vectors may optionally include cleavage and/or polyadenylations signals and/or a 3' untranslated regions. Vectors often include one or more appropriately positioned sites for restriction enzymes, to facilitate introduction into the vector of the nucleic acid to be expressed. An expression vector typically comprises sufficient cis-acting elements for expression; other elements required or helpful for expression can be supplied by the cell or in vitro expression system into which the vector is introduced.

Various techniques known in the art may be employed for introducing nucleic acid molecules into cells. Such techniques include chemical-facilitated transfection using compounds such as calcium phosphate, cationic lipids, cationic polymers, liposome-mediated transfection, non-chemical methods such as electroporation, particle bombardment, or microinjection, and infection with a virus that contains the nucleic acid molecule of interest (sometimes termed "transduction"). Markers can be used for the identification and/or selection of cells that have taken up the vector and, typically, express the nucleic acid. Cells can be cultured in appropriate media to select such cells and, optionally, establish a stable cell line, e.g., polyclonal or monoclonal cell line. As used herein, a stable cell line is a cell line composed of cells that have an exogenous nucleic acid encoding a gene product to be expressed integrated into the genome of the cells or, in some embodiments, present on an episome that is maintained and transmitted with high fidelity to daughter cells during cell division. Methods of generating stable cell lines are well known in the art and include, e.g., transfection, viral infection (e.g., using retroviruses (e.g., lentiviruses), adenoviruses, adeno-associated viruses, herpesviruses, etc.), typically followed by selection of cells that have taken up and stably maintain an introduced nucleic acid or portion thereof. A stable cell line may be polyclonal (descended from a pool of cells that have taken up a vector) or may be monoclonal (descended from a single cell that has taken up a vector).

Selection of appropriate expression control elements may be based, e.g., on the cell type and species in which the nucleic acid is to be expressed. One of ordinary skill in the art can readily select appropriate expression control elements and/or expression vectors. In some embodiments, expression control element(s) are regulatable, e.g., inducible or repressible. Exemplary promoters suitable for use in bacterial cells include, e.g., Lac, Trp, Tac, araBAD (e.g., in a pBAD vectors), phage promoters such as T7 or T3. Exemplary expression control sequences useful for directing expression in mammalian cells include, e.g., the early and late promoters of SV40, adenovirus or cytomegalovirus immediate early promoter, or viral promoter/enhancer sequences, retroviral LTRs, promoters or promoter/enhancers from mammalian genes, e.g., actin, EF-1 alpha, phosphoglycerate kinase, etc. Regulatable (e.g., inducible or repressible) expression systems such as the Tet-On and Tet-Off systems (regulatable by tetracycline and analogs such as doxycycline) and others that can be regulated by small molecules such as hormone receptor ligands (e.g., steroid receptor ligands, which may or may not be steroids), metal-regulated systems (e.g., metallothionein promoter), etc.

II. Quantitative Protein-Protein Interaction Assays

Protein-protein interactions are of central importance in most biological functions. For example, multi-protein complexes carry out fundamental biological processes such as DNA replication and transcription. Signal transduction, the process by which signals from the exterior of a cell are mediated to the inside of the cell, often involves a series of protein-protein interactions of the signaling molecules involved. Protein-protein interactions are involved in transport of proteins between intracellular compartments. Proteins may form relatively long-lived complexes or interact for brief periods of time. For example, proteins responsible for post-translational modifications such as phosphorylation, dephosphorylation, acylation, etc., frequently interact transiently with the protein to be modified. A variety of methods have been developed to detect protein-protein interactions. For example, the yeast two-hybrid screen and variations thereof are widely used, and screens have yielded thousands of protein-protein interactions. However, there remains a need for methods of identifying or assessing protein-protein interactions, e.g., that methods that can be used to identify and/or assess protein-protein interactions in a more quantitative manner.

In some aspects, the invention provides methods (also referred to as "assays") useful for identifying, detecting, and/or quantifying (measuring), protein-protein interactions, e.g., protein-protein interactions that take place intracellularly. In some aspects, the invention provides reagents (e.g., recombinant nucleic acid constructs, vectors, cell lines containing one or more recombinant nucleic acids) suitable for use in the methods. For example, the invention provides recombinant nucleic acid constructs and vectors, e.g., expression vectors, encoding labeled prey proteins and/or labeled bait proteins. In some aspects, the invention provides stable cell lines capable of expressing a labeled prey protein. In some aspects, the invention provides kits comprising one or more of the reagent(s). For example, a kit could comprise a stable cell line capable of expressing a labeled prey protein of interest and/or a set of nucleic acid constructs, e.g., expression vectors, suitable for transient transfection to express labeled bait protein(s) of interest. Kits can comprise compound(s) for use as a positive or negative control. Kits can comprise instructions for performing an assay of the invention.

As described further below, in some aspects, an inventive protein-protein interaction assay comprises isolating bait protein (including bait protein present in bait-prey complexes), measuring prey protein isolated with the bait protein in bait-prey complexes, and measuring total bait protein isolated, thereby controlling the measurement of the protein-protein interaction for the amount of bait protein present. In some embodiments, isolating bait protein comprises immobilizing ("capturing") bait protein to a solid support. A solid support can be, e.g., an inner surface of a well, particles (often referred to as "beads", e.g., agarose beads, magnetic beads), filter, membrane, etc. In some embodiments, an inventive protein-protein interaction assay comprises isolating bait protein in a well and measuring prey and/or bait levels in the same well, without the need to remove bait-prey complexes from the well. In some embodiments, isolating bait protein in a well comprises immobilizing bait protein to one or more inner surface(s) of the well.

In many embodiments, the bait protein and prey protein are labeled. For example, the bait protein and/or prey protein may be produced as a fusion protein comprising a detectable tag. In some embodiments, the prey protein is labeled with a luminescent or fluorescent label and is measured based on luminescence or fluorescence. In some embodiments, the bait protein is labeled with an epitope tag (which can be used to isolate the bait protein, e.g., to immobilize the bait protein to an inner surface of a well) and is measured by detecting the tag, e.g., using an ELISA assay. In some embodiments, the prey protein is labeled with a luminescent or fluorescent label and is measured based on luminescence or fluorescence, and the bait protein is labeled with an epitope tag and is measured using an ELISA assay. In some aspects, a protein-protein interaction assay that involves a bait protein and a prey protein, in which both the bait protein and the prey protein that participate in the protein-protein interaction are measured (e.g., wherein the assay comprises controlling for the amount of bait protein), is referred to as a quantitative protein-protein interaction (QPPI) assay. In embodiments wherein at least one of the bait protein or prey protein is labeled (tagged) with a luminescent label and the amount of said protein is measured based on detecting luminescence, the assay may be termed a quantitative luminescence-based protein-protein interaction (QLPPI) assay. In some aspects, a QPPI assay comprises (i) isolating bait protein (thereby also isolating prey present in bait-prey complexes); (ii) measuring prey protein in bait-prey complexes; and (iii) measuring total bait protein isolated. In some aspects, a QLPPI assay employs luminescence (e.g., for purposes of measuring prey protein) and comprises (i) isolating bait protein (thereby also isolating prey present in bait-prey complexes); (ii) measuring prey protein in the bait-prey complexes; and (iii) measuring total bait protein isolated, wherein said measuring is based on luminescence.

In some embodiments, a QPPI assay, e.g., a QLPPI assay, comprises isolating bait protein in a well (thereby also isolating prey present in bait-prey complexes) and measuring prey and/or bait in the same well. In some embodiments, isolating bait protein in a well comprises immobilizing bait protein to one or more inner surface(s) of the well (thereby also immobilizing prey present in bait-prey complexes).

In some aspects, either of two proteins whose interaction is to be assessed may be considered to be a prey protein, with the other protein being considered to be a bait protein. In some aspects, an inventive assay comprises (i) isolating bait-prey complexes using a binding agent that has affinity to the bait; and (ii) measuring both the amount of prey isolated together with the bait in bait-prey complexes and the total amount of bait isolated, thereby controlling for the amount of bait. (It will be understood that both bait-prey complexes and bait that is not present in bait-prey complexes would be isolated in step (i) of the preceding method.) In some aspects, an inventive assay comprises (i) isolating bait-prey complexes using a binding agent that has affinity to the prey; and (ii) measuring both the amount of bait isolated together with the prey in bait-prey complexes and the total amount of prey isolated, thereby controlling for the amount of prey. (It will be understood that both bait-prey complexes and prey that is not present in bait-prey complexes would be isolated in step (i) of the preceding method.) Thus in some aspects, the inventive assay comprises isolating bait-prey complexes using a binding agent with affinity to an interaction partner (bait or prey) and controlling for the total amount of whichever interaction partner the binding agent has affinity to.

In some embodiments, cells express two or more bait proteins, wherein the bait proteins comprise different labels. In some embodiments, cells express two or more prey proteins, wherein the prey proteins comprise different labels. In some embodiments, cells express at least two bait proteins and at least two prey proteins.

In some aspects, an inventive QPPI assay (e.g., QLPPI assay) makes use of a stable cell line expressing a prey protein, e.g., a prey protein labeled with a label permitting luminescence-based detection. Cells may be transiently transfected with a nucleic acid construct encoding a bait protein, e.g., a bait protein labeled with a tag that allows isolation of the bait protein. In some embodiments, the tag both allows isolation of the bait protein and measurement of isolated bait protein. In some embodiments, the bait protein may comprise a second tag that is used for measurement. In some aspects, wherein cells are transiently transfected with a nucleic acid construct encoding a prey protein, isolation of bait-prey complexes is performed based on affinity to the prey protein, the amount of bait protein isolated with the prey protein is measured, and the total amount of prey protein isolated (i.e., prey protein present in bait-prey complexes and prey protein not present in bait-prey complexes) is measured. In some aspects, wherein cells are transiently transfected with a nucleic acid construct encoding a bait protein, isolation of bait-prey complexes is performed based on affinity to the bait protein, the amount of prey protein isolated with the bait protein is measured, and the total amount of bait protein isolated (i.e., bait protein present in bait-prey complexes and bait protein not present in bait-prey complexes) is measured.

In some aspects, the use of cell line(s) that stably express a labeled prey protein, controlling for the amount of bait protein, and/or performing measurements without need to remove bait-prey complexes from the well in which the prey is measured substantially increases reproducibility and/or quantitativeness of the assay as compared, for example, with methods of assessing protein-protein interactions described in Barrios-Rodiles et al., Science, 307: 1621-5, 2005 and/or U.S. Ser. No. 10/526,733. In some aspects, inventive protein-protein interaction assays are capable of detecting small differences or changes in the strength of protein-protein interactions, thereby facilitating identification of conditions and/or compounds that modulate proteins and/or modulate protein-protein interactions.

The invention provides a method for detecting a protein-protein interaction, the method comprising steps of: (a) providing a lysate prepared from cells that express a prey protein and a bait protein, wherein the prey protein is labeled with a detectable label and the bait protein is tagged with a tag that allows separation of the bait protein and protein(s) interacting with the bait protein from other proteins in the lysate; (b) immobilizing the tag to one or more inner surface(s) of a well, thereby immobilizing the bait protein and protein(s) interacting with the bait protein; (c) detecting immobilized prey protein by detecting the detectable label, thereby detecting a protein-protein interaction. In some embodiments, detecting immobilized prey protein comprises measuring immobilized prey protein by, e.g., determining the magnitude (intensity, strength, etc.) of a signal produced directly or indirectly by the detectable label. In some embodiments, lysate components that are not immobilized to the inner surface of the wells is removed (e.g., by washing) prior to detecting the immobilized prey protein. In some embodiments, the method further comprises detecting and measuring the immobilized bait protein by, e.g., determining the magnitude (intensity, strength, etc.) of a signal produced directly or indirectly by the tag. In some embodiments, a reaction is performed in the same well for purposes of detecting the bait protein. In some embodiments, at least a portion of the contents of the well is then transferred to a different vessel, and a measurement is performed on the transferred contents. For example, if the prey is measured by detecting luminescence, it may be convenient to use a black plate, while if the bait is measured using a colorimetric method, it may be convenient to use a transparent (clear) plate.

In some embodiments, a ratio of prey protein to bait protein [prey/bait] provides a measurement of the protein-protein interaction, with a higher [prey/bait] ratio indicating a stronger interaction. In some embodiments, a logarithm of [prey/bait], e.g., $\log_2$ [prey/bait] is used as a measurement of the protein-protein interaction. In some aspects, an inventive assay provides highly reproducible results between replicates. In some embodiments, "replicates" refers to performing the assay multiple times, e.g., using samples of a lysate comprising the same prey and bait proteins in different wells (e.g., of a multi-well plate). For example, in some embodiments the correlation when multiple assay are performed in replicate is such that $R^2$ is at least 0.95, e.g., between 0.95 and 0.99 (rounded to the nearest hundredth), e.g., 0.96, 0.97, 0.98, or 0.99 (as rounded to the nearest hundredth).

In many embodiments, the bait protein and prey protein are provided as recombinant proteins, e.g., fusion proteins, wherein the recombinant protein comprises a polypeptide label, e.g., at the N- or C-terminus, synthesized by a cell as part of protein. The invention contemplates embodiments in which a label becomes covalently or noncovalently attached to a bait or prey protein after synthesis of the protein by a cell. The label can be attached intracellularly or, in the case of bait or prey proteins that comprise an extracellular domain, after the protein is exposed at the cell surface. In this regard, a bait or prey protein can comprise any of a variety of polypeptides that are capable of undergoing reactions with a substrate, resulting in covalent attachment of at least a portion of the substrate to the polypeptide. Such polypeptides are often enzymatically active, typically with specificity for a limited range of substrates. In some embodiments, the substrate(s) are molecules that are not normally found in the environment in which the polypeptide is typically present. For example, the substrate(s) are not normally found in cells that produce the polypeptide (or in media in which such cells are cultured). The substrate comprises a detectable moiety, which is transferred to the polypeptide as a result of the reaction. In some embodiments, HaloTag® technology, or a similar system, is used to attach a label to the polypeptide. HaloTag is a modified haloalkane dehalogenase designed to covalently bind to synthetic ligands (HaloTag ligands). The synthetic ligands comprise a chloroalkane linker attached to a molecule such as a fluorescent dye, affinity handle, or solid surface. Covalent bond formation between the protein tag (HaloTag) and the chloroalkane linker is reported to be highly specific, occur rapidly under physiological conditions, and be essentially irreversible. See, e.g., Los G V, HaloTag: a novel protein labeling technology for cell imaging and protein analysis. ACS Chem Biol. 3(6):373-82 (2008). In some embodiments, a protein comprises a SNAP-tag or CLIP-tag (both available from New England Biolabs, Ipswich, Mass.). SNAP-tag is a 20 kDa mutant of the DNA repair protein that reacts specifically and rapidly with benzylguanine (BG) derivatives, leading to irreversible covalent labeling of the SNAP-tag with the BG derivative, which can comprise any of a wide variety of different detectable moieties (Keppler, A. et al., Nat. Biotechnol. 21, 86 (2003)). CLIP-tag is a variant of SNAP-tag that reacts specifically with O2-benzylcytosine (BC) derivatives (Gautier, A., et al., Chem. Biol. 15, 128 (2008)). In some embodiments, an extracellular portion of a protein can be labeled with a cell-impermeable dye, e.g., an Alexa dye (e.g., AlexaFluo 350, AlexaFluor 488 or AlexaFluor 546), EAM-1, or Calcium green dextran. In some embodiments, a protein is labeled using a cell-permeable label, such as carboxyfluorescein or BODIPY FL. In some embodiments, a radioactive moiety is used to label a bait or prey protein. For example, a protein can be metabolically labelled with $[^{32P}]$Pi, $[^{33P}]$Pi, etc. In some embodiments, a protein comprises a tetracysteine tag, which specifically chelates biarsenical compounds such as FlAsH and ReAsH that fluoresce upon binding to the tag (Martin, B R, et al., Nat Biotechnol. 23(10):1308-14 (2005)).

In some embodiments, providing a lysate prepared from cells that express a prey protein and a bait protein comprises preparing a lysate from the cells or obtaining a lysate that has been prepared from the cells, e.g., a lysate prepared by a third party. In general, the lysate is prepared from cells that have been maintained for a period of time, e.g., in cell culture in a cell culture vessel, so that the bait and prey proteins have the opportunity to interact. The cells can be maintained using standard cell culture methods and culture medium suitable for cells of that type. One of ordinary skill would select an appropriate cell culture medium for cells to be used in an inventive assay. In some embodiments, a medium contains serum and/or albumin. In some embodiments, a serum-free medium is used. In some embodiments, a chemically defined medium is used. In some embodiments, a chemically defined medium is free or essentially free of components such as serum or animal extracts whose composition is at least partly unknown and/or may vary significantly from batch to batch. In some embodiments, cells are exposed to one or more physical or chemical conditions for a period of time prior to preparing the lysate, e.g., as discussed further below. The inventive assay may be used to assess the effect of the condition(s) on a protein and/or on a protein-protein interaction.

In general, a lysate for use in the invention can be prepared using standard methods known in the art. Typically, lysing the cells comprises contacting them with a suitable lysis solution (also called "lysis buffer"), e.g., a buffered solution that promotes lysis of the cells. One of ordinary skill in the art would know how to select an appropriate lysis buffer. A lysis buffer may comprise one or more detergents, protease inhibitors, phosphatase inhibitors, stabilizers, etc., as known in the art. For example, a non-denaturing detergent, e.g., a non-ionic detergent of the Triton-X series (e.g., Triton X-100) or a zwitterionic detergent such as CHAPS could be used. Sodium fluoride may be used to inhibit protein phosphoseryl and phosphothreonyl phosphatases (PSPs). Sodium orthovanadate may be used as an inhibitor for protein phosphotyrosyl phosphatases (PTPs). Phosphatase inhibitors may be useful to preserve the protein phosphorylation state in cells, cell lysates, and protein kinase assays. For example, many proteins, e.g., the activity and/or protein-protein interactions of many kinases can be regulated at least in part by phosphorylation. If a bait or prey protein is a kinase, it may be desirable to inhibit phosphatase activity in the lysate. In some embodiments, a lysis solution contains a molybate oxoanion, e.g., as sodium molybdate. For example, sodium molybdate may be used if a prey or bait protein is an HSP90, e.g, HSP90A, to help stabilize complexes comprising HSP90. In some embodiments, cells are contacted with a crosslinking agent prior to preparing the lysate. In some embodiments a crosslinking agent is not used. In some embodiments, a mechanical method is used to effect or promote lysis. In some embodiments, a lysate is subjected to centrifugation, fractionation, or one or more other processing steps prior In some embodiments, a method of the invention comprises providing cells from which a lysate is prepared. In many embodiments of the invention, cells are eukaryotic cells, e.g., fungal cells, plant cells, or animal cells (e.g., insect cells, vertebrate cells). In some embodiments, cells are mammalian cells, e.g., human cells, non-human primate cells, or rodent (e.g., mouse, rat) cells. Often a cell is a member of a cell line, e.g., an established or immortalised cell line that has acquired the ability to proliferate indefinitely in culture (e.g., as a result of selection, mutation, or genetic manipulation). Numerous cell lines are known in the art and can be used in the instant invention. Mammalian cell lines include, e.g., HEK-293 (e.g., HEK-293T, also called 293T), CHO, NIH-3T3, COS, Jurkat, Vero, and HeLa cell lines. Numerous additional cell lines are described e.g., in the paper and/or online catalogs of various depositories and cell banks such as the American Type Culture Collection (ATCC), Coriell Cell Repositories, Deutsche Sammlung von Mikroorganismen and Zellkulturen (German Collection of Microorganisms and Cell Cultures; DSMZ), European Collection of Cell Cultures (ECACC), Japanese Collection of Research Bioresources (JCRB), RIKEN, Cell Bank Australia, etc., from which these cell lines may be obtained. The paper and online catalogs of the afore-mentioned depositories and cell banks are incorporated herein by reference. Cells may be adherent or non-adherent in various embodiments. Cells may be non-tumorigenic or tumorigenic in various embodiments. In some embodiments, a cell of the same species as the species of origin of the bait and prey proteins is used. For example, human cells may be used to assess interactions between proteins of human origin. In some embodiments, cells are obtained from a subject suffering from a disease (or are descended from cells obtained from such a subject). The cells may exhibit one or more characteristics or mutations associated with or characteristic of the disease. In some embodiments, cells are genetically modified to stably express a labeled prey and/or bait protein. In some embodiments, cells have one or more genetic modifications in addition to any genetic modification associated with rendering them capable of expressing a labeled prey and/or bait protein. For example, cells may be genetically modified to express a short hairpin RNA or a gene whose mutation or overexpression is associated with or contributes to development or progression of a disease. In some embodiments cells are of a cell type or tissue of origin of interest. For example, in some embodiments cells are fibroblasts, endothelial cells, epithelial cells, neurons, glial cells, epidermal cells, endocrine gland cells, exocrine gland cells, hepatocytes, keratinocytes, melanocytes, chondrocytes, lymphoid cells, e.g., lymphocytes (e.g., B or T lymphocytes), macrophages, monocytes, mononuclear cells, muscle cells, osteoblasts, osteoclasts, etc.

In some embodiments, cells are from a cell line that stably expresses a labeled prey protein, labeled bait protein, or both. In some embodiments, a constitutive promoter is used. In some embodiments, expression of a bait and/or prey protein is regulatable, e.g., inducible or repressible. In some embodiments, providing the cells comprises generating the cells, e.g., generating a stable cell line that expresses a labeled bait protein, labeled prey protein, or both. In some embodiments, a cell line stably expresses a prey protein and is transiently transfected with a bait protein. In some embodiments, a cell line stably expresses a bait protein and is transiently transfected with a prey protein. For example, cells can be transfected with an expression vector encoding a bait protein about 12-96 hours prior to preparation of a lysate, e.g., about 24-48 hour prior to preparation of the lysate. In some embodiments, a cell line stably expresses a prey protein, and populations of cells from the cell line are transiently transfected (e.g., in different wells of a multiwell plate or plates) with members of a panel of bait proteins. The bait proteins may share one or more characteristics. For example, they may belong to a particular functional and/or functional class or exhibit a particular type of enzymatic activity.

In general, the number of cells and amount of nucleic acid used for transient transfection can depend on factors such as the size of the well, cell type, etc., and can be determined by one of ordinary skill in the art. In some embodiments, cells are at a confluence of about 25%-75%, e.g., about 50%, at the time of addition of compounds. In some embodiments, between 1,000 and 10,000 cells/well (e.g., about 5,000 cells/well) are plated in about 100 µl medium per well in 96-well plates. In other exemplary embodiments, cells are seeded in about 30 µl-50 µl of medium at between 500 and 2,000 (e.g., about 1000) cells per well into 384-well plates. Multiple replicates can be performed.

In general, any type of vessel or article capable of containing cells and/or cell lysate can be used in various embodiments of the invention. The term "well" is used herein to refer to any type of vessel or article that can contain a lysate and/or cells. In many embodiments, vessels are wells of a multiwell plate (also called a "microwell plate", "microtiter plate", etc.). For example, commercially available 96-well, 384-well, or 1536-well plates are used in various embodiments. Such plates are widely available in, e.g., clear, white, or black. Often they are made of various plastics, e.g., polystyrene, and the wells may be treated to facilitate their use in applications such as cell culture, ELISA assays, etc. One of ordinary skill would be aware of how to select an appropriate plate for use in cell culture and/or for use with particular detectable label(s). While multiwell plates provide a convenient and very useful format suitable for performing assays of the invention, the invention is not limited to use of wells or to use of multiwell plates. In some embodiments, any article of manufacture in which multiple physically separated cavities (or other confining features) are present in or on a substrate can be used, wherein assays can be performed without intermingling contents of different cavities.

After preparation of the lysate, bait and bait-prey complexes are isolated using any suitable method. In many embodiments, bait and bait-prey complexes are isolated based on affinity of a binding agent to the bait (typically the affinity is to a tag with which the bait has been tagged). In some embodiments, multiwell plates with high protein binding capacity are used for immobilization (capture) of bait and bait-prey complexes. In some embodiments, plates suitable for performing ELISA assays are used. In some embodiments, flat bottomed plates are used. In some embodiments, wells are prepared for use in an inventive assay by contacting inner surface(s) of the well with a binding agent capable of specifically binding to a tag with which a bait protein has been tagged. "Inner surfaces" refer to the bottom and/or sides of the well, i.e., those portions that would typically come in contact with a lysate placed in the well. Following addition of lysate to the well, the binding agent binds to the tag, thereby immobilizing bait and bait-prey complexes to inner surfaces of the well. Various binding agents can be used. One of ordinary skill in the art would be able to select an appropriate binding agent for a particular tag. Often, a binding agent is an antibody, e.g., a monoclonal antibody, although other binding agents such as aptamers, peptides, small molecules, metals, or any other entity capable of binding to a tag with reasonable specificity and sufficient affinity to maintain a stable association with the tag during performance of subsequent steps of the assay (e.g., removal of unbound lysate components) can be used. For example, if a tag is a His tag, a plate coated with a metal such as nickel can be used. It will be understood that the binding agent need not be completely specific for the tag, so long as the specificity is sufficient to permit capture of the target protein (i.e., protein comprising the tag) without undue interference by non-target proteins. For example, a binding agent to be used to isolate bait and bait-prey complexes should not significantly bind to prey protein or proteins that would interfere with measurement of the bait and/or prey protein. In embodiments in which multiple different bait proteins comprising different tags are used, the binding agents should be sufficiently specific for the particular tag to which they are intended to bind so as to not substantially bind to other tags that may be present. In some embodiments, the affinity (as measured by the equilibrium dissociation constant, Kd) of a binding agent for a tag is $10^{-3}$ M or less, e.g., $10^{-4}$ M or less, e.g., $10^{-5}$ M or less, e.g., $10^{-6}$ M or less, $10^{-7}$ M or less, $10^{-8}$ M or less, or $10^{-9}$ M or less under the conditions tested, e.g., assay conditions.

Inner surface(s) of a well can be sides and/or bottom of a well. The binding agent, e.g., antibody, may adsorb to the inner surface(s). The binding agent may be non-covalently or covalently attached to the inner surface(s) in various embodiments. The binding agent may be directly attached or indirectly attached. For example, the binding agent may be attached to another entity that is directly attached to the well. In some embodiments, inner surface(s) are substantially coated with the binding agent. In some embodiments, only part of an inner surface or surfaces is coated. Wells may be treated with a blocking agent to inhibit non-specific binding of proteins in the lysate prior to placing the lysate in the wells. Methods suitable for preparing wells for use in ELISA assays are known in the art and can be used to prepare wells for use in an inventive assay. Coated microplates are commercially available.

In some aspects, cells that express a prey protein are cultured in a first set of wells, transfected with a nucleic acid construct encoding the bait protein, and lysed in said first set of wells, and lysates are transferred to a second set of wells (on a different plate), wherein the second set of wells comprises a binding agent that binds to the bait protein. In some embodiments, lysates obtained from cells cultured and transfected in 96 well plate(s) are consolidated into a plate with more wells, e.g., a 384 or 1536 well plate.

Isolation of bait and bait-prey complexes (or prey and prey-bait complexes) typically entails incubating the lysate in the presence of the binding agent, e.g., in wells comprising the binding agent, for a suitable period of time, whereby the bait or prey (and bait-prey complexes) bind to the binding agent. After isolation, the amount of bait and prey is measured. Prior to measurement, unbound material from the lysate may be removed from the well, e.g., by washing. In general, the method of performing the measurements will be based on the identity of the label/tag with which the bait and prey protein are labeled. For example, if a label comprises a luciferase, a luciferase substrate will be added to the well (typically together with other components useful for performing the reaction). If a label comprises a fluorescent protein, fluorescence is measured, e.g., using a suitable fluorescence detector. If a label comprises an epitope tag, a binding agent, e.g., an antibody, which is itself labeled with an enzyme, fluorophore, or other detectable label can be used to measure the amount of epitope tag. In some embodiments, detection is performed using a laser scanner or plate reader, e.g., a fluorescence plate reader, or luminescence plate reader or absorbance plate reader. As discussed above, a measurement of the protein-protein interaction may be obtained by computing a ratio of prey to bait protein measured (if the assay comprises isolating bait-prey complexes based on affinity to the bait protein), wherein the higher the ratio of prey to bait, the greater the magnitude of the interaction. In some embodiments, a logarithm of [prey/bait], e.g., $\log_2$ [prey/bait] is used as a measure of the interaction. In some aspects, a method of the invention comprises computing an interaction score(s) for one or more prey and bait protein pairs. In some embodiments, interaction scores are determined for a prey protein of interest with regard to a plurality of different bait proteins. In some embodiments, interaction scores are determined for a bait protein of interest with regard to a plurality of different prey proteins.

In general, an inventive quantitative protein-protein interaction assay (e.g., QPPI assay, e.g., QLPPI assay) can be used for a wide variety of purposes. For example, a protein-protein interaction assay of the invention can be used to identify as yet undiscovered protein-protein interactions, measure known or newly identified protein-protein interactions, perform interactome mapping, etc. In some embodiments, an inventive QPPI assay is used to compare one or more interactions of a mutant protein with those of its wild type counterpart. In some embodiments, a QPPI assay is used to assess protein-protein interactions of proteins involved in a signaling pathway. Exemplary signaling pathways include, e.g., the MAPK signaling pathway, ErbB signaling pathway, Wnt signaling pathway, Notch signaling pathway, Hedgehog signaling pathway, TGF-beta signaling pathway, mTOR signaling pathway, VEGF signaling pathway, Jak-STAT signaling pathway, NOD-like receptor signaling pathway, toll-like receptor signaling pathway, chemokine signaling pathways, T cell receptor signaling pathway, B cell receptor signaling pathway, calcium signaling pathway, phosphatidylinositol signaling pathway, and sub-pathways of any of the foregoing pathways. In some embodiments, a QPPI assay is used to assess protein-protein interactions of proteins involved in a biological process, e.g., cell division, transcription, neurotransmission, etc. In some embodiments, an inventive assay is used to generate an interaction map. In some embodiments, an interaction map is a chaperone-co-chaperone interaction map. In some embodiments an interaction map is a chaperone-client interaction map. In some embodiments, a map is a heatmap, wherein potential interactants are listed on the edges of the map forming a grid, and wherein different colors correspond to interaction strength. In some embodiments, a map represents interactions by lines or arrows between interacting components. In some embodiments, a line width or color corresponds to interaction strength.

In some embodiments, a QPPI assay is used to identify compounds that disrupt one or more protein-protein interactions. In some embodiments, a QPPI assay is used to identify and/or characterize compound(s) that disrupt one or more protein-protein interactions. Many proteins form homodimers or heterodimers or other complexes containing two or more proteins (collectively "multimers"). For example, many transcription factors, receptors, and other proteins function as dimers and/or are transported or maintained in an inactive state as a result of interaction with other protein(s). In some embodiments, a QPPI assay of the invention is used to identify and/or characterize compound(s) capable of altering, e.g., inhibiting, interaction between proteins that exist or function as multimers.

In general, any proteins of interest can be used as bait and prey proteins in a protein-protein interaction assay of the invention, e.g., a QLPPI assay. The protein(s) may or may not have a known function or activity. Exemplary proteins of interest include, e.g., transcription factors, signal transduction proteins, receptors, enzymes, channels, transporters, etc. In some embodiments, a bait or prey protein is associated with a disease. For example, aberrant expression (e.g., overexpression, underexpression), mislocalization, aberrant post-translational modification, and/or aberrant activity of the protein is known or suspected to contribute to development and/or progression of a disease. In some embodiments, a bait or prey protein contains a mutation. In some embodiments, the mutation is a naturally arising mutation, e.g., a mutation arising without deliberate intervention by the hand of man intended to produce a mutation. In some embodiments, the mutation is genetically engineered. In some embodiments, the mutation is associated with a disease, e.g., the mutation is known or suspected to contribute to development and/or progression of a disease.

In some embodiments, a disease is a proliferative disease. Proliferative diseases include a variety of diseases characterized by excessive and/or aberrant cell proliferation. Proliferative diseases include benign tumors and malignant tumors (cancer). Cancer, as used herein, encompasses malignant solid tumors (carcinomas, sarcomas) and hematologic malignancies. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. In some embodiments a proliferative disease is myeloproliferative disease, e.g., myelodysplastic syndrome, myelofibrosis, essential thrombocythemia, or polycythemia vera. In some embodiments, a proliferative disease is neurofibromatosis, tuberous sclerosis, or lymphangioleiomyomatosis. In some embodiments, a proliferative disorder is a disorder characterized by excessive fibrosis and/or excessive proliferation of fibroblasts, myofibroblasts, or other connective tissue cells, typically associated with excessive extracellular matrix components, e.g., collagen. In some embodiments, the disorder is restenosis, e.g., following angioplasty. In some embodiments, a disorder is associated with pathological angiogenesis.

In some embodiments, a disease is an autoimmune disease (e.g., rheumatoid arthritis). In some embodiments, a disease is a cardiovascular disease. In some embodiments, the disease is a metabolic disease. In some embodiments, a disease is a neurodegenerative disease. In some embodiments, a disease is a psychiatric disease.

In some embodiments, the invention provides a method of assessing the effect one or more condition(s) of interest on one or more proteins or protein-protein interaction(s). In some embodiments, the method comprises using a QPPI assay of the invention, e.g., a QLPPI assay, to compare one or more protein-protein interactions occurring in populations of cells that have been maintained under different conditions or sets of conditions. In some embodiments, cells are cultured in culture medium containing or not containing a compound of interest (or containing different concentrations of the compound) and/or cultured under selected conditions of temperature, pH, oxygen tension, radiation, etc. For example, cells may be subjected to heat shock, radiation, or another source of cell stress. One or more protein-protein interaction(s) is measured using a lysate prepared from cells maintained under a first condition or set of conditions and compared with the level of such interaction(s) as measured using a lysate prepared from cells maintained under a second condition or set of conditions. The cells cultured under the different conditions may be cultured in parallel (e.g., in different wells of a multiwell plate, or in different plates or vessels that are processed in a substantially uniform manner (except with regard to the particular difference in conditions whose effect is to be assessed) and over a substantially similar time period, or they may be cultured in different experiments. For example, once a protein-protein interaction between particular bait and prey proteins has been measured under a given set of conditions, the value obtained may be used as a reference value for comparison with measurements made under other condition. In some aspects, the high degree of reproducibility afforded by the inventive protein-protein interaction assays provides confidence that differences observed between measurements obtained from cells cultured under different selected conditions arise as a result of the different conditions rather than due to variability inherent to the assay. In some aspects, the high degree of reproducibility afforded by the inventive protein-protein interaction assays facilitates comparison between experiments.

In some embodiments, the invention provides protein-protein interaction assays, e.g., QPPI assays, e.g., QLPPI assays, as described above, wherein a protein of interest is a chaperone. For example, in some embodiments, a chaperone is used as a prey protein, and a co-chaperone or client is used as a bait protein. In some embodiments, a QPPI assay, e.g., a QLPPI assay, is used to identify and/or characterize an interaction between a chaperone and a client protein, or between a chaperone and a co-chaperone. In some embodiments, a QPPI assay, e.g., a QLPPI assay, is used to identify and/or characterize interactions between a chaperone and a plurality of co-chaperones and/or client proteins. In some embodiments, a QPPI assay, e.g., a QLPPI assay, is used to identify one or more protein clients of a chaperone, wherein the protein(s) were not previously known to be clients of said chaperone. In some embodiments, a chaperone or client is a protein listed in any of FIGS. 11-16.

In some embodiments, a chaperone is a heat shock protein (HSP). HSPs are a class of proteins whose expression increases when cells are exposed to elevated temperatures or various other types of stress although many of them are constitutively expressed. HSPs occur in virtually all living organisms, from bacteria to humans, and play important roles in a wide variety of biological processes. HSPs have historically been named according to their molecular weight. For example, HSP40, HSP60, HSP70 and HSP90 refer to families of heat shock proteins typically on the order of 40, 60, 70 and 90 kilodaltons in size, respectively. In some embodiments of the invention, a chaperone, e.g., an HSP, is an HSP40 (also called DNAJ), HSP70, or HSP90 family member.

The HSP40 (DNAJ) family is the largest HSP family in humans and has been divided into 3 subfamilies (A, B, and C) based on homology to the DnaJ protein from *E. coli*. Members of the HSP40 family can be identified by the presence of a conserved J-domain known to be responsible for HSPA recruitment and stimulation of the HSPA ATPase activity and are also called the J-protein family. Many members of the HSP40 family function to regulate the activity of HSP70s. For example, their roles include targeting HSP70 activity to clients at various locations in cells and/or binding client proteins directly, thereby delivering specific clients to HSP70. In some embodiments of the invention, a chaperone is an HSP40, e.g., an A, B, or C type HSP40.

The human genome encodes about 13 members of the HSP70 (HSPA) family (Kampinga, 2009). Among the best known members are the stress-inducible form Hsp70/Hsp72 (HSPA1A), the constitutively expressed Hsc70/Hsp73/Hsc73 (HSPA8), the endoplasmic reticulum form, Grp78/BiP (HSPA5), and Hsp75/mtHsp70/mortalin/TRAP-1 (HSPA9). Of these, the cytosolic inducible HSP70 is the most studied and can mediate, e.g., cytoprotective, antiapoptotic, and immune regulatory effects. In some embodiments of the invention, a chaperone is an HSP70, e.g., HSPA1A. Further information regarding HSP40s, HSP70s, and their interactions with each other and/or with client proteins is found in Kampinga H H, Craig E A. Nat Rev Mol Cell Biol., 11(8):579-92, 2010, and references therein.

The HSP90 family is among the most highly conserved HSP families and can be divided into five subfamilies as follows: cytoplasmic HSP90 (HSP90A family), endoplasmic reticulum (ER) HSP90 (HSP90B family); bacterial Hsp90 (HtpG family), mitochondrial HSP90 (TRAP family), chloroplast HSP90 (HSP90C family) (see Taipale, M, et al., Nat. Rev. Mol. Cell. Biol. 11(7):515-28, 2010, for review). It should be noted that the designation of HSP90 family members based on localization (e.g., cytoplasmic, ER, mitochondrial) is not absolute. For example, cytoplasmic HSP90 can be found extracellularly as well as in the nucleus and mitochondria.

The HSP90A family (cytoplasmic HSP90) is of particular interest in certain aspects of the invention. Evolutionarily recent gene duplication events have resulted in multiple genes encoding cytosolic HSP90 in many organisms. For example, most vertebrates, including humans, have two genes encoding HSP90A proteins with highly overlapping functions: HSP90AA1 (Gene ID for human gene: 3320; Gene ID for mouse ortholog: 15519) and HSP90AB1 (Gene ID for human gene: 3326; Gene ID for mouse gene: 15516). The proteins encoded by HSP90AA1 and HSP90AB1 are referred to as HSP90α and HSP90β, respectively. HSP90β is used as an exemplary HSP90A in various embodiments of the instant invention and in various parts of the description herein. It should be understood that the invention provides analogous embodiments in which HSP90α is used. For purposes of description herein, the term "HSP90" will generally be used to refer to any HSP90 protein; the term "HSP90A" will generally be used to refer to any HSP90A protein; the term "HSP90B" will generally be used to refer to any HSP90B protein, etc. In general, where a term that encompasses multiple HSPs is used herein, the invention provides embodiments pertaining to each member of the group encompassed by the term unless otherwise indicated. For example, where the term "HSP90A" is used, the invention provides embodiments in which the HSP90A is HSP90α and embodiments in which the HSP90A is HSP90β. It will be understood that where an aspect of the invention pertains to or makes use of an HSP-client interaction and/or HSP-co-chaperone interaction, an appropriate HSP-client and/or HSP-co-chaperone pair would be identified and/or selected.

HSP90A is an ATPase and contains three structural domains: a highly conserved N-terminal (NTD) domain of ~25 kDa, which contains a binding pocket for ATP; a middle domain (MD) of ~40 kDa, and a C-terminal domain (CTD) of ~12 kDa. A "charged linker" region connects the N-terminus with the middle domain and is sometimes considered to constitute a fourth domain. A conserved MEEVD pentapeptide located at the C-terminal end of HSP90A serves as a tetratricopeptide repeat (TPR) motif recognition site and is involved in the interaction of HSP90A with a variety of co-chaperones. HSP90A forms homodimers and undergoes a dynamic cycle termed the "chaperone cycle" involving ATP binding and hydrolysis, during which it undergoes conformational shifts that are important in its recognition and release of clients (Taipale, 2010).

Figure 16:
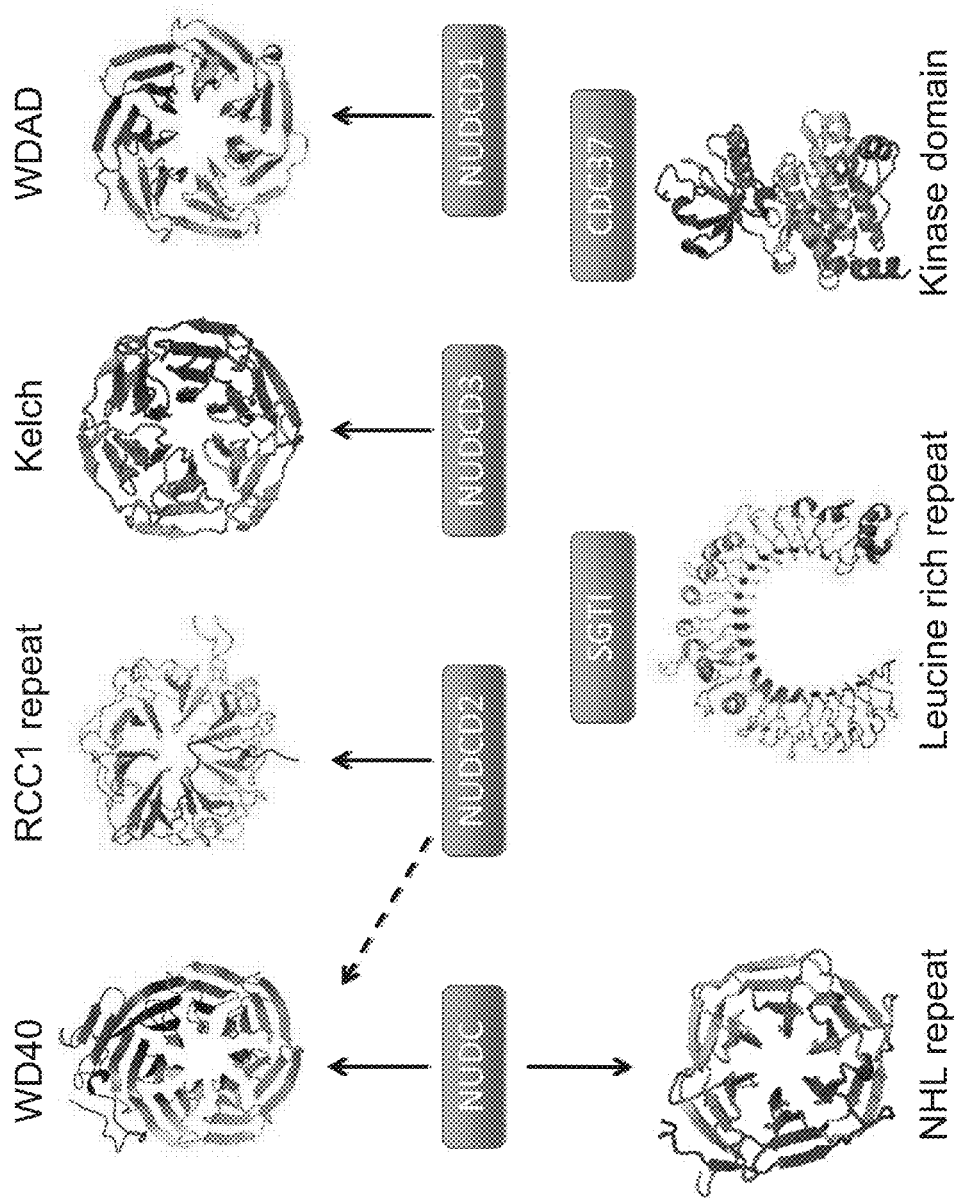
FIG. 16 is a schematic diagram summarizing data from various experiments showing that co-chaperones NUDC, NUDCD2, NUDCD3, NUDC1, SGTI, and CDC37 interact preferentially with client proteins containing the indicated domains (WD40, RCC1 repeat, Kelch, WDAD, NHL repeat, Leucine rich repeat, Kinase domain).

In addition to ATP binding and hydrolysis, HSP90A is regulated by interaction with various co-chaperones that can modulate HSP90A function by, e.g., coordinating interaction of HSP90A with other chaperone systems such as HSP70, modulating HSP90A's ATPase activity, recruiting particular classes of clients to HSP90A, and (in some cases) contributing to the chaperone cycle via their enzymatic activities. For example, co-chaperones containing a TPR domain facilitate cooperative interactions between HSP90A and certain HSP40 and HSP70 family members on various client proteins to achieve maturation. Examples of co-chaperones that recruit particular classes of clients to HSP90A include, e.g., CDC37 (recruits kinases); UNC45 (recruits myosin); FKBP family members (recruit nuclear receptors), SGTI (LRR proteins); TOM70 (recruits mitochondrial proteins). Exemplary co-chaperone-client specificities are indicated in FIG. 16. It will be understood that the specificity of co-chaperones for particular classes of client protein is not absolute. For example, CDC37 (Gene ID for human gene: 11140; Gene ID for mouse ortholog: 12539) is a co-chaperone that has been shown to have client proteins that are not kinases.

Figure 10:
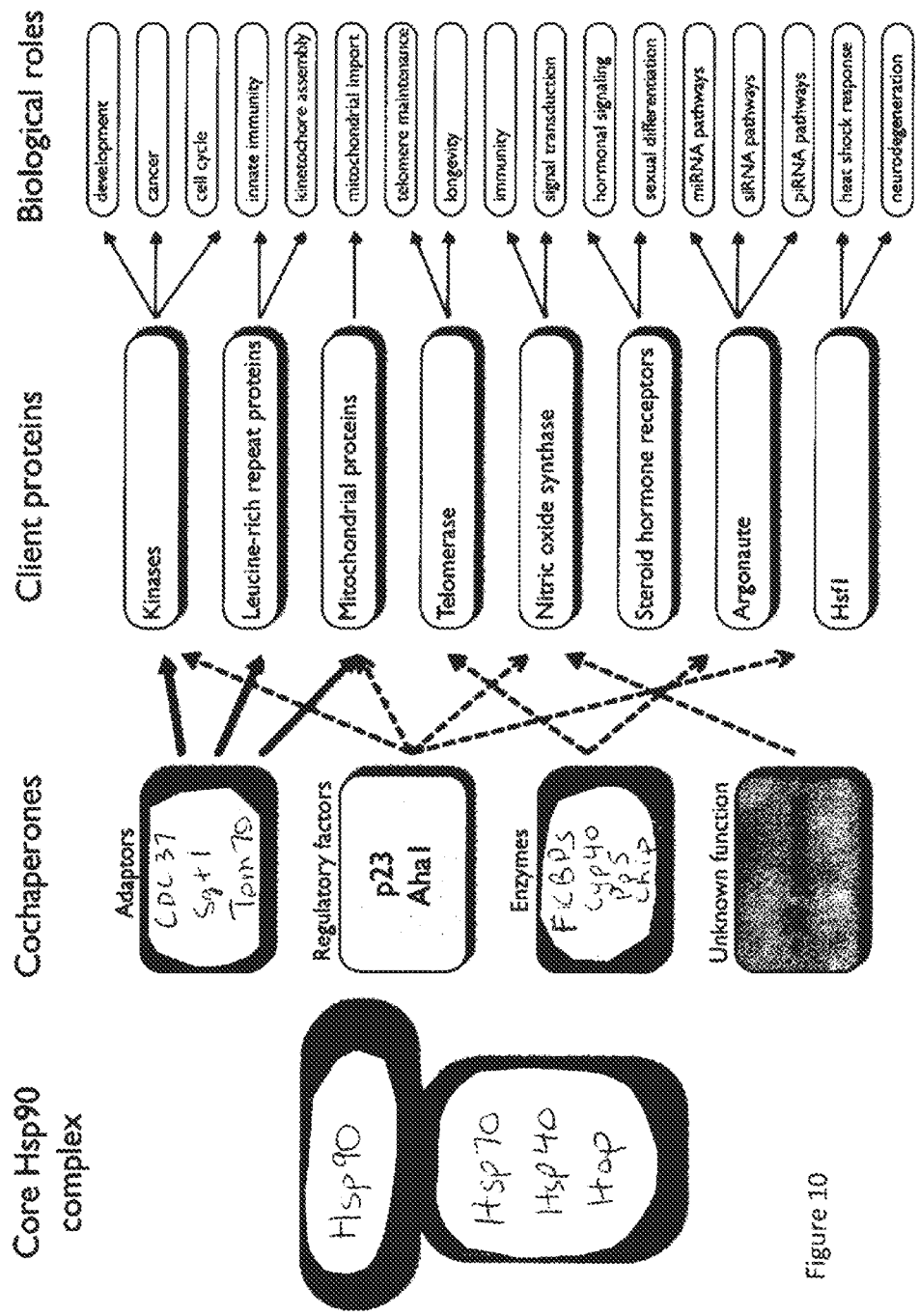
FIG. 10 shows a summary of various HSP90A co-chaperones, client proteins, and examples of some biological processes in which the client proteins are involved.

HSP90A chaperones a diverse set of client proteins, and its functions extend well beyond roles in stress tolerance. HSP90A and its clients are involved in a diverse set of biological processes, examples of which are indicated in FIG. 10. HSP90A client proteins include, for example, kinases, receptors, transcription factors, enzymes, mitochondrial proteins imported from the cytoplasm, calcineurin, heat shock factor 1 (HSF1), telomerase reverse transcriptase (TERT), endothelial nitric oxide synthase (eNOS), histones, channel subunits, viral proteins, myosin, argonaute, G proteins, and leucine rich repeat (LRR) proteins. It will be appreciated that some proteins are members of more than one of the foregoing categories. A non-limiting list of proteins that interact with HSP90A, including clients as well as co-chaperones, is available at www.picard.ch/downloads/downloads.htm. Receptors include, e.g., nuclear receptors and cell surface receptors (e.g., transmembrane receptors), etc. Examples include G protein coupled receptors (e.g., adrenergic, cannabinoid, purinergic receptors, neuropeptide receptors). Transcription factors (TFs) (sometimes called sequence-specific DNA-binding factors) bind to specific DNA sequences and (alone or in a complex with other proteins), regulate transcription, e.g., activating or repressing transcription. Exemplary TFs are listed, for example, in the TRANSFACO database, Gene Ontology (www.geneonlology.org/) or DBD (www.transcriptionfactor.org) (Wilson, et al, DBD—taxonomically broad transcription factor predictions: new content and functionality Nucleic Acids Research 2008 doi:10.1093/nar/gkm964). TFs can be classified based on the structure of their DNA binding domains (DBD). For example in certain embodiments a TF is a helix-loop-helix, helix-turn-helix, winged helix, leucine zipper, bZIP, zinc finger, homeodomain, or beta-scaffold factor with minor groove contacts protein. Transcription factors include, e.g., p53, STAT3, PAS family transcription factors (e.g., HIF family: HIF1A, HIF2A, HIF3A), aryl hydrocarbon receptor. LRR proteins include mammalian nucleotide-binding domain, leucine rich containing (NLR) proteins. Histones include H1, H2A, H2B, H3, H4; viral proteins include various proteins of hepatitis B, C, and E; picornavirus, reovirus, etc. Numerous G protein coupled receptors (GPCRs) are known in the art. See, e.g., Vroling B, GPCRDB: information system for G protein-coupled receptors. Nucleic Acids Res. 2011 January; 39(Database issue): D309-19. Epub 2010 Nov. 2. The GPCRDB can be found online at www.gpcr.org/7tm/.

HSP90A can be inhibited by a variety of small molecules such as ansamycin (e.g., geldanamycin and analogs thereof), radicicol, and molecules comprising purines, pyrazoles, isoxazoles and other scaffolds (Taldone, T., et al. Bioorg Med Chem., 17(6):2225-35, 2009; Trepel, J., et al., Nat Rev Cancer. 10(8):537-49, 2010). Most of these compounds bind the ATP binding site of HSP90 and inhibit the ATP-dependent chaperone activities of HSP90, resulting in reduced client activity, e.g., by prolonging interaction of the client with HSP70 and/or targeting improperly folded or aggregated client to the ubiquitin pathway for degradation. In some embodiments, an inventive QPPI assay is used to assess the effect of an HSP90 inhibitor on interaction between HSP90 and one or more clients or co-chaperones.

In some embodiments of interest, an HSP90A client is a kinase. Kinases are enzymes that transfer (catalyze the transfer of) a phosphate group from a high energy donor molecule (typically a nucleoside triphosphate such as ATP) to an acceptor or substrate molecule. Kinases play important roles in diverse cellular and developmental processes including cell cycle progression, metabolism, and angiogenesis, among others, and are key components of numerous signal transduction pathways. Inhibition of kinases as a therapeutic strategy is of considerable importance. For example, kinase inhibitors have been approved for use in treating a variety of different cancers and show promise in a number of non-oncologic indications. Kinases can be classified based on the nature of their typical substrates and include protein kinases (i.e., kinases that transfer phosphate to one or more protein(s)), lipid kinases (i.e., kinases that transfer a phosphate group to one or more lipid(s)), nucleotide kinases, etc. Protein kinases (PKs) are of particular interest in certain aspects of the invention. PKs are often referred to as serine/threonine kinases (S/TKs) or tyrosine kinases (TKs) based on their substrate preference. Serine/threonine kinases (EC 2.7.11.1) phosphorylate serine and/or threonine residues while TKs (EC 2.7.10.1 and EC 2.7.10.2) phosphorylate tyrosine residues. A number of "dual specificity" kinases (EC 2.7.12.1) that are capable of phosphorylating both serine/threonine and tyrosine residues are known. The human protein kinase family can be further divided based on sequence/structural similarity into the following groups: (1) AGC kinases—containing PKA, PKC and PKG; (2) CaM kinases—containing the calcium/calmodulin-dependent protein kinases; (3) CK1—containing the casein kinase 1 group; (4) CMGC—containing CDK, MAPK, GSK3 and CLK kinases; (5) STE—containing the homologs of yeast Sterile 7, Sterile 11, and Sterile 20 kinases; (6) TK—containing the tyrosine kinases; (7) TKL—containing the tyrosine-kinase like group of kinases. A further group referred to as "atypical protein kinases" contains proteins that lack sequence homology to the other groups but are known or predicted to have kinase activity, and in some instances are predicted to have a similar structural fold to typical kinases.

Figure 2:
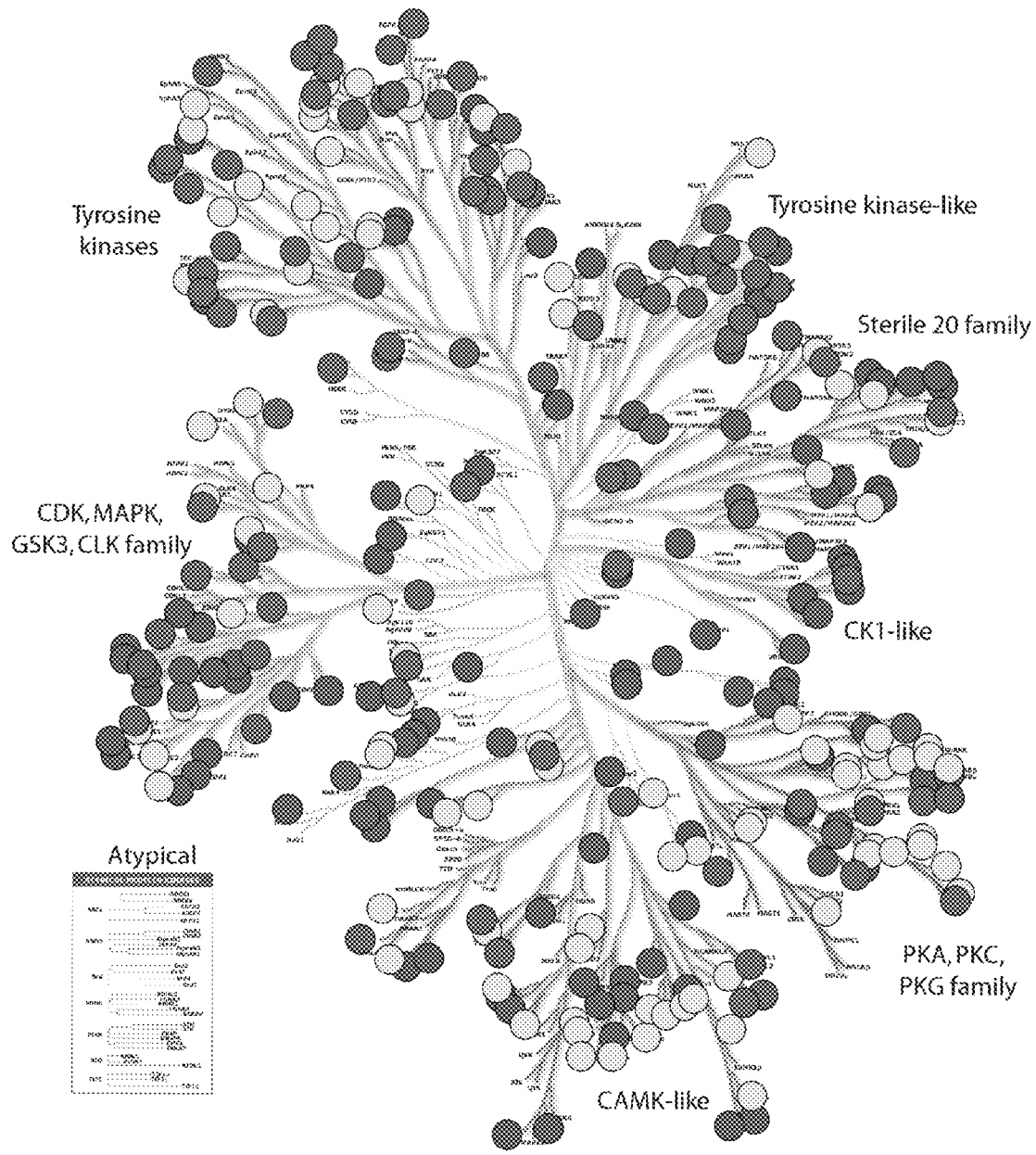
FIG. 2 is a phylogenetic tree (dendrogram) that depicts the relationships between members of the superfamily of human protein kinases (the "human kinome") and classifies each kinase as high (green), intermediate (yellow), or low/no (red) based on its level of interaction with Hsp90β. "Low/no" interaction refers to a level of interaction that could not reliably be distinguished from background under the conditions tested. The dendrogram structure is adapted from a poster published to accompany Manning et al. Science, 298, 1912-1934, 2002 (also available at kinase.com/human/kinome/), from which the names of the kinases in FIG. 2 are evident.

The present invention provides the recognition that HSP90A client proteins encompass a substantial proportion of the human kinome. As described in further detail in the Examples, a quantitative luminescence-based protein-protein interaction assay in which HSP90β was used as a prey protein and about 370 different human kinases were used as bait was performed. FIG. 2 shows a dendrogram indicating kinases that were shown to interact with HSP90β in the QLPPI assay. It was found that the majority of kinases physically interact with HSP90β. A list of the kinases found to interact with HSP90β is presented in Table 1. It is expected that additional kinases not included in the panel would also interact with HSP90β. It is also expected that at least some of kinases among those tested that did not appear to interact with HSP90A under the conditions used would interact under other conditions (e.g., elevated temperature or other cell stresses). In some aspects, an inventive QPPI assay is used to identify conditions under which a kinase of interest interacts with an HSP90 protein, e.g., an HSP90A protein.

A panel of kinase mutants and kinase fusion protein, including a number of kinases bearing mutations associated with cancer and/or kinase fusion proteins (e.g., arising from chromosomal translocations) associated with cancer, was tested for interaction with HSP90β. Table 1 lists kinase mutants and kinase fusion proteins that were found to interact with HSP90β. In some instances, kinase mutants or kinase fusion proteins were found to interact with HSP90β in instances where the corresponding wild type kinase did not interact under the conditions tested. Without wishing to be bound by any theory, this result may be due at least in part to decreased stability of the kinase arising from the mutation or fusion, tending to increase the amount of mutant kinase or kinase fusion protein in an at least partly unfolded state in which it interacts with HSP90β, and potentially reflect an increased reliance of the mutant kinase on HSP90β function for maintaining activity of the mutant kinase or kinase fusion protein.

In some aspects, an inventive assay is used with a mutant kinase or fusion protein comprising a kinase. In some embodiments, a mutant kinase or fusion protein is associated with a disease, e.g., cancer, or associated with resistance to an inhibitor. Numerous kinase mutations found in human cancer are known in the art. See, e.g., Appendix I-XVI in Matthews, D J and Gerritson, M., Targeting Protein Kinases for Cancer Therapy, Wiley, 2010. available online at ftp.wiley.com/public/sci_tech_med/protein_kinase. In some embodiments, a mutation alters the activity of the protein. A mutation may result in a protein with increased activity (an activating mutation), decreased activity, altered localization, altered regulation, etc. In some embodiments, a mutation is associated with a non-oncologic disease. In some embodiments, a disease in which a mutation is found is Pfeiffer syndrome, Loeys-Dietz syndrome, or primary pulmonary hypertension.

In some aspects, an inventive QPPI assay, e.g., a QLPPI assay, is used to measure interaction between a CDC37 protein and a kinase. In some aspects, an inventive QPPI assay is used to identify conditions under which a kinase of interest interacts with a CDC37 protein.

In some embodiments a client, e.g., an HSP90A client, is a nuclear receptor. Nuclear receptors are members of a large superfamily of evolutionarily related DNA-binding transcription factors that exhibit a characteristic modular structure consisting of five to six domains of homology (designated A to F, from the N-terminal to the C-terminal end). The activity of NRs is regulated at least in part by the binding of a variety of small molecule ligands to a pocket in the ligand-binding domain. The human genome encodes about 50 NRs. Members of the NR superfamily include glucocorticoid, mineralocorticoid, progesterone, androgen, and estrogen receptors, peroxisome proliferator-activated (PPAR) receptors, thyroid hormone receptors, retinoic acid receptors, retinoid X receptors, NR1H and NR1I receptors, and orphan nuclear receptors (i.e., receptors for which no ligand has been identified as of a particular date). In some embodiments a nuclear receptor (NR) is a nuclear receptor subfamily 0 member, nuclear receptor subfamily 1 member, nuclear receptor subfamily 2 member, nuclear receptor subfamily 3 member, nuclear receptor subfamily 4 member, nuclear receptor subfamily 5 member, or nuclear receptor subfamily 6 member. In some embodiments a nuclear receptor is NR1D1 (nuclear receptor subfamily 1, group D, member 1), NR1D2 (nuclear receptor subfamily 1, group D, member 2), NR1H2 (nuclear receptor subfamily 1, group H, member 2; synonym: liver X receptor beta), NR1H3 (nuclear receptor subfamily 1, group H, member 3; synonym: liver X receptor alpha), NR1H4 (nuclear receptor subfamily 1, group H, member 4), NR1I2 (nuclear receptor subfamily 1, group I, member 2; synonym: pregnane X receptor), NR1I3 (nuclear receptor subfamily 1, group I, member 3; synonym: constitutive androstane receptor), NR1I4 (nuclear receptor subfamily 1, group I, member 4), NR2C1 (nuclear receptor subfamily 2, group C, member 1), NR2C2 (nuclear receptor subfamily 2, group C, member 2), NR2E1 (nuclear receptor subfamily 2, group E, member 1), NR2E3 (nuclear receptor subfamily 2, group E, member 3), NR2F1 (nuclear receptor subfamily 2, group F, member 1), NR2F2 (nuclear receptor subfamily 2, group F, member 2), NR2F6 (nuclear receptor subfamily 2, group F, member 6), NR3C1 (nuclear receptor subfamily 3, group C, member 1; synonym: glucocorticoid receptor), NR3C2 (nuclear receptor subfamily 3, group C, member 2; synonym: aldosterone receptor, mineralocorticoid receptor), NR4A1 (nuclear receptor subfamily 4, group A, member 1), NR4A2 (nuclear receptor subfamily 4, group A, member 2), NR4A3 (nuclear receptor subfamily 4, group A, member 3), NR5A1 (nuclear receptor subfamily 5, group A, member 1), NR5A2 (nuclear receptor subfamily 5, group A, member 2), NR6A1 (nuclear receptor subfamily 6, group A, member 1), NROB1 (nuclear receptor subfamily 0, group B, member 1), NROB2 (nuclear receptor subfamily 0, group B, member 2), RARA (retinoic acid receptor, alpha), RARB (retinoic acid receptor, beta), RARG (retinoic acid receptor, gamma), RXRA (retinoid X receptor, alpha; synonym: nuclear receptor subfamily 2 group B member 1), RXRB (retinoid X receptor, beta; synonym: nuclear receptor subfamily 2 group B member 2), RXRG (retinoid X receptor, gamma; synonym: nuclear receptor subfamily 2 group B member 3), THRA (thyroid hormone receptor, alpha), THRB (thyroid hormone receptor, beta), AR (androgen receptor), ESR1 (estrogen receptor 1), ESR2 (estrogen receptor 2; synonym: ER beta), ESRRA (estrogen-related receptor alpha), ESRRB (estrogen-related receptor beta), ESRRG (estrogen-related receptor gamma), PGR (progesterone receptor), PPARA (peroxisome proliferator-activated receptor alpha), PPARD (peroxisome proliferator-activated receptor delta), PPARG (peroxisome proliferator-activated receptor gamma), VDR (vitamin D (1,25-dihydroxyvitamin D3) receptor). In some embodiments a protein comprises a naturally occurring truncated form of a nuclear receptor generated by proteolytic cleavage, such as truncated RXR alpha, or truncated estrogen receptor. In some embodiments a receptor, e.g., a NR, is an HSP70 client. For example, androgen receptor (AR) and glucocorticoid receptor (GR) are HSP70 clients. Extensive information regarding NRs may be found in Germain, P., et al., Pharmacological Reviews, 58:685-704, 2006, which provides a review of nuclear receptor nomenclature and structure, and other articles in the same issue of Pharmacological Reviews for reviews on NR subfamilies). In some embodiments, an HSP90A client is a steroid hormone receptor (e.g., an estrogen, progesterone, glucocorticoid, mineralocorticoid, or androgen receptor), PPAR alpha, or PXR. In some aspects, an inventive QPPI assay, e.g., a QLPPI assay, is used to measure interaction between an HSP, e.g., HSP90A or HSP70 and a NR. In some aspects, an inventive QPPI assay, e.g., a QLPPI assay, is used to measure interaction between a FKBP and a NR. In some embodiments a client is a ligand-dependent transcription factor (TF). A ligand-dependent TF is characterized in that binding of a ligand to the protein modulates activity of the protein. In some embodiments binding of a ligand to ligand-dependent TF causes a conformational change in the protein that results in, e.g., nuclear translocation of the protein, dissociation of one or more proteins from the TF, activation of the TF, or repressesion of the TF. In some embodiments a ligand-dependent transcription factor is an NR. In some embodiments a ligand-dependent TF is not considered to be a member of the NR superfamily. In some embodiments a ligand-dependent TF is the AHR (aryl hydrocarbon receptor).

NRs play important roles in a wide range of biological processes such as development, differentiation, reproduction, immune responses, metabolic regulation, and xenobiotic metabolism, among others, as well as in a variety of pathological conditions. NRs represent an important class of drug targets. Pharmacological modulation of NRs is of use in a variety of disorders including cancer, autoimmune, metabolic, and inflammatory/immune system disorders (e.g., arthritis, asthma, allergies) as well as post-transplant immunosuppression in order to reduce the likelihood of rejection. In addition to interacting with endogenous and/or exogenous small molecule ligand(s), NRs interact with a variety of endogenous proteins such as dimerization partners, coactivators, corepressors, ubiquitin ligases, kinases, phosphatases, which can modulate their activity. Measuring such interactions in a quantitative manner using an assay of the invention may allow, for example, a more detailed understanding of these interactions and how they may vary in different cell types and/or under different conditions. Such information may be of use, e.g., in identifying or characterizing compounds that selectively modulate NR activity. Analogous methods may be applied to other TF(s), e.g., ligand-dependent TFs.

In some embodiments a client is a xenobiotic receptor selected from AHR, CAR, PXR, PPARA, PPARD, and PPARD. Xenobiotic receptors "induce" or enhance the transcription of genes encoding biotransformation enzymes (e.g., cytochrome P450 enzymes) and/or xenobiotic transporters in mammalian organisms, in response to binding of various non-endogenous ligands ("xenobiotics") or endogenous ligands to the receptor. See, e.g., Curtis J. Omiecinski, C J, et al., Toxicol. Sci. (2011) 120 (suppl 1): S49-S75, and other articles in the same issue of Toxicol. Sci., which are incorporated herein by reference, for exemplary discussion of xenobiotic receptors and various ligands thereof. In some embodiments a method comprises determining whether a test agent is a candidate modulator of a xenobiotic receptor.

In some embodiments a ligand modulates activity of a NR or other ligand-dependent TF. In some embodiments a ligand stimulates activity of a NR or other ligand-dependent TF. Such a ligand may be referred to as an "agonist". In some embodiments a ligand does not affect activity of a NR or other ligand-dependent TF in the absence of an agonist. However, the ligand, which may be referred to as an "antagonist" is capable of inhibiting the effect of an agonist through, e.g., competitive binding to the same binding site in the protein as does the agonist or by binding to a different site in the protein. Certain NRs or other ligand-dependent TFs promote a low level of gene transcription in the absence of agonists (also referred to as basal or constitutive activity). Ligands that reduce this basal level of activity in nuclear receptors may be referred to as inverse agonists One of ordinary skill in the art would readily be able to obtain amino acid sequences of proteins of interest, e.g., chaperones, co-chaperones, clients, and other proteins that are of interest as bait and/or prey proteins, and nucleic acid sequences encoding them, from publicly available databases such as those available at the National Center for Biotechnology Information (www.ncbi.nih.gov). Exemplary databases include, e.g., GenBank, RefSeq, Gene, UniProt, SwissProt, and the like. One of ordinary skill in the art will appreciate that sequences, e.g., mRNA and polypeptide sequences, in the NCBI Reference Sequence (RefSeq) database may be used as standard sequences for a nucleic acid or protein of interest.

III. Chaperone Interaction Assays

In some aspects, the invention provides methods of identifying and/or characterizing modulators (e.g., inhibitors or activators) of protein activity. In some aspects, the invention provides compositions of use in the methods. In some aspects, methods are based at least in part on detecting an interaction between a chaperone and a client of the chaperone in the presence of a test agent. In some embodiments, a measurement of the level of interaction that occurs between a chaperone and a client of the chaperone in the presence of a test agent is used to determine whether the test agent is a candidate modulator of the client. The invention encompasses the recognition that binding of a modulator to a client protein can result in a decrease in the interaction of the client with a chaperone or co-chaperone with which the client normally interacts (i.e., with which the client interacts in the absence of the modulator). Without wishing to be bound by any theory, the decreased interaction may occur at least in part due to stabilization of the client by the modulator, resulting in a reduced amount of an at least partly unfolded form of the client that would otherwise interact with the chaperone. For example, without wishing to be bound by any theory, binding of a small molecule to a kinase may stabilize the kinase and reduce its tendency to assume a partially unfolded state in which it would be more likely to interact with HSP90β and/or co-chaperone(s) such as CDC37. The invention provides the recognition that detecting a decrease in interaction between a client and a chaperone or co-chaperone arising as a result of binding of an agent, e.g., a small molecule, to the client can be used to identify and/or characterize modulators of the client. The invention provides a variety of methods (assays) based at least in part on detecting a chaperone-client interaction, e.g. detecting an alteration in a chaperone-client interaction. For purposes of the present invention, an assay that comprises detecting and/or measuring a chaperone-client interaction and/or comprises detecting and/or measuring an alteration in a chaperone-client interaction that occurs under different conditions (e.g., in the presence or absence of a test agent) will be referred to as a chaperone-client interaction (CCI) assay.

Figure 3:
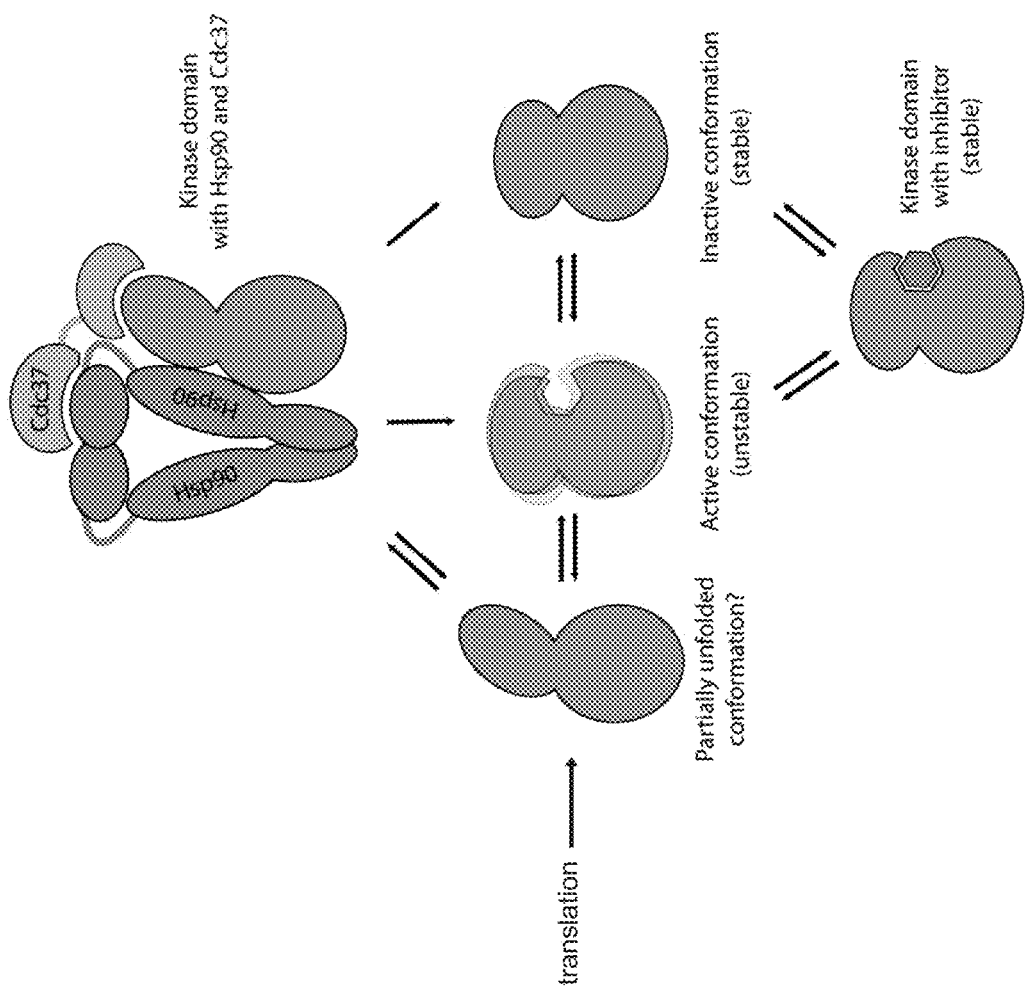
FIG. 3 is a schematic diagram of a model for the interaction that occurs between Hsp90/CDC37 and kinases and the stabilizing effect of an inhibitor on kinase conformation.
Figure 6:
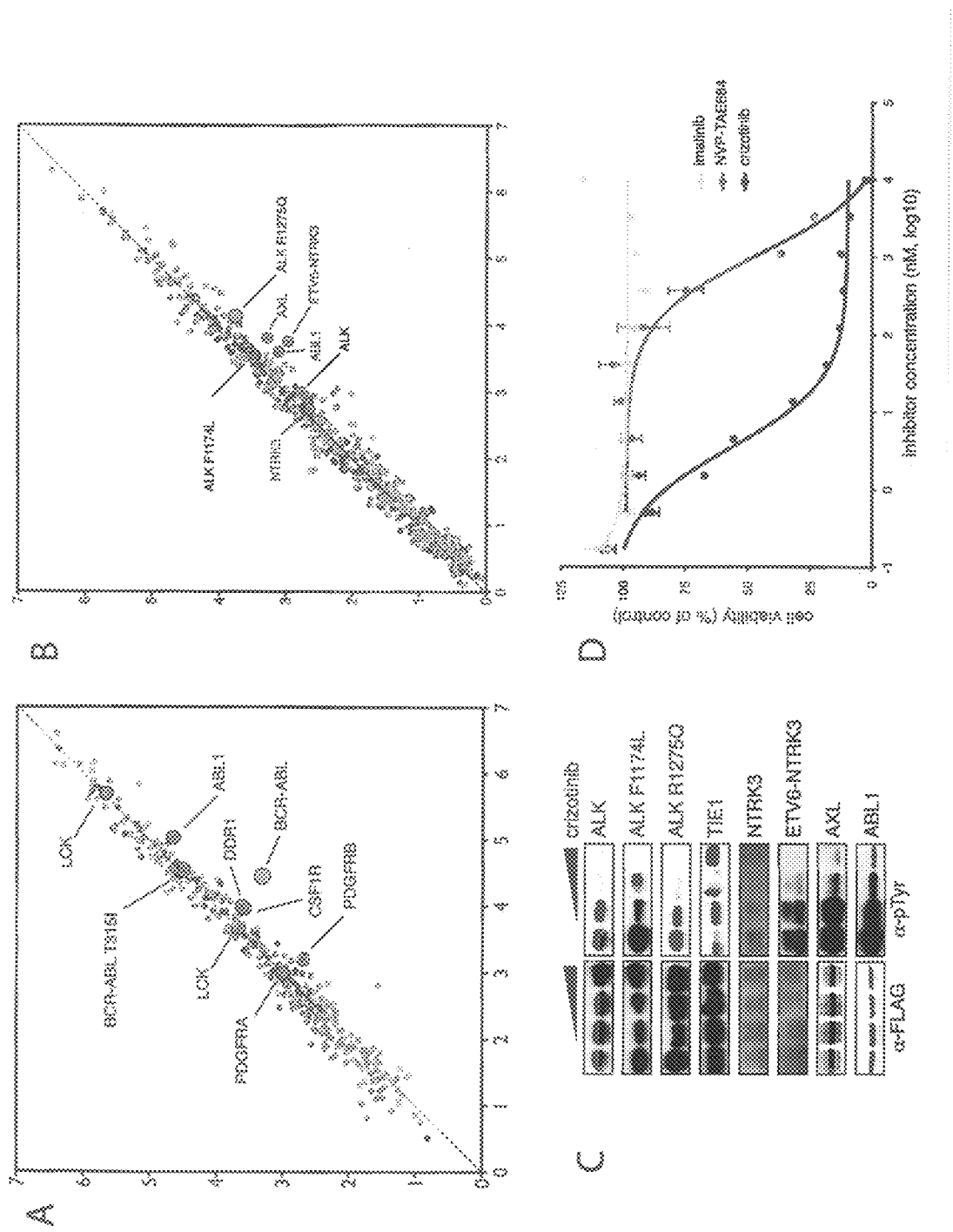
FIG. 6(A) is a plot of the interaction scores for members of a kinase panel in the absence (x-axis) or presence (y-axis) of imatinib.
FIG. 6(B) is a plot of the interaction scores for members of a kinase panel in the absence (x-axis) or presence (y-axis) of crizotinib.
FIG. 6(C) is a Western blot showing results of an experiment in which 293T cells were transfected with kinase constructs (tagged with 3×FLAG-V5) and 48 hours later were treated with increasing concentrations of crizotinib or left untreated for 1 h. Epitope-tagged proteins were immunoprecipitated with anti-FLAG beads and tyrosine phosphorylation was measured with anti-phosphotyrosine antibody. Anti-FLAG blot is a control for protein levels.
FIG. 6(D) shows that crizotinib inhibited the growth of ETV6-NTRK3 positive MO91 cells with IC50 of 5 nM.
FIG. 6(E) shows that crizotinib inhibited growth of MO01 xenografts in vivo.
FIG. 6(F) shows a quantitative assessment of the effect of crizotinib on the interaction between HSP90β and ALK or various indicated ALK mutants.
FIG. 6(G) shows a quantitative assessment of the effect of crizotinib on the interaction between HSP90β and ALK, wild type NTRK3, or ETV6-NTRK3 fusion protein.

As described further detail in the Examples, it was observed that the level of interaction between HSP90β and a wide variety of different kinase clients is decreased in the presence of kinase inhibitors that bind to the kinase. For example, a QLPPI assay of the invention was used to measure interaction between HSP90β and a panel of kinases in the presence or absence of imatinib, a kinase inhibitor that is known to inhibit BCR-ABL, ABL, PDGFR, DDR1, and CSF1R. As shown in FIG. 6(A), the interaction of these kinases with HSP90β was detectably decreased in the presence imatinib as compared with its absence. In contrast, interaction of a BCR-ABL mutant (BCR-ABL (T315I)) with HSP90β was not decreased by imatinib, consistent with the known inability of imatinib to that is known to be resistant to imatinib (i.e., a mutant whose activity is not substantially inhibited by imatinib) with HSP90β was not significantly affected by imatinib. It was also found that the presence of a small molecule inhibitor of a kinase decreases interaction of the kinase with CDC37 which, as discussed above, is an HSP90A co-chaperone that is at least partly specific for kinase clients of HSP90A. Without wishing to be bound by any theory, it is possible that the binding of a small molecule to a kinase stabilizes the kinase such that its tendency to assume an at least partly unfolded conformation in which it would tend to interact with HSP90β and/or CDC37 is decreased, as depicted schematically in FIG. 3.

In some aspects, the invention provides a method of identifying a candidate modulator of a protein of interest, the method comprising: (a) providing a composition comprising a chaperone, a test agent, and a protein of interest, wherein the protein of interest is a client of the chaperone; (b) assessing a protein-protein interaction between the protein of interest and the chaperone in the presence of the test agent, wherein if the interaction between the protein of interest and the chaperone is reduced in the presence of the test compound as compared with the interaction between the chaperone and the protein of interest in the absence of the test compound, the test compound is identified as a candidate modulator of the protein of interest. In some aspects, the invention provides a composition comprising: a chaperone, a test agent, and a protein of interest, wherein the protein of interest is a client of the chaperone. In many embodiments, an identified candidate modulator is an inhibitor of the protein of interest. For example, a compound may block a substrate binding site or a co-factor binding site or stabilize an inactive conformation of the protein or otherwise inhibit or block the protein from interacting with its target. However, the invention also encompasses identification of activators. For example, a compound may stabilize an active conformation of a protein without blocking its substrate binding site or otherwise interfering with activity. In some embodiments, a candidate modulator is further tested to assess its effect on activity of a protein of interest. For example, a direct assay of enzymatic activity (e.g., using purified protein of interest) can be used, or a bioassay can be performed. In some embodiments, a decrease in chaperone-client interaction score measured in the presence of a test agent as compared with that measured in the absence of the test agent indicates that a test agent modulates, e.g., inhibits, the client. In some embodiments, a reduction in interaction score is statistically significant. In some embodiments, an interaction score is reduced by at least 1%, e.g., between 1% and 100%, e.g., between 5% and 50%. In some embodiments, a fold change in interaction ($score_{compound}$-$score_{control}$) is equal to or less than −0.05, e.g., between −0.1 and −5, e.g., between −0.2 and −5, e.g., between −0.5 and −5, e.g., between −1 and −5. In some embodiments, a fold change in interaction ($score_{compound}$-$score_{control}$) equal to or less than −0.05, e.g., between −0.1 and −5, e.g., between −0.2 and −5, e.g., between −0.5 and −5, e.g., between −1 and −5, is considered to indicate that a test compound meaningfully inhibits interaction between the chaperone and the client, wherein control score is the interaction score in the absence of the test compound. In some embodiments, a fold change in interaction ($score_{compound}$-$score_{control}$) equal to or less than −0.05, e.g., between −0.1 and −5, e.g., between −0.2 and −5, e.g., between −0.5 and −5, e.g., between −1 and −5, is considered to indicate that a test compound meaningfully modulates, e.g., inhibits, the client, wherein control score is the interaction score in the absence of the test compound.

In some embodiments, interaction scores and/or changes in interaction scores are assessed for a compound using a panel of client proteins. In some embodiments, kinases are ranked based on the extent to which their interaction score is reduced by a compound of interest (e.g., a kinase inhibitor). In some embodiments, a kinase is considered a target of the inhibitor if it is among the 1%, 5%, 10%, or 20% of kinases whose HSP90A and/or CDC37 interaction score is most greatly reduced by the inhibitor, among a panel of at least 100 kinases. In some embodiments, a kinase is considered a target of the inhibitor if it is among the 5, 10, 20, or 50 kinases whose HSP90A and/or CDC37 interaction score is most greatly reduced by the inhibitor, among a panel of at least 100 kinases. In some embodiments, results are represented using a heatmap or dendrogram. In the heatmap, colors can correspond to the extent to which the interaction score is altered. In the dendrogram, clients can be represented as circles, ovals, etc., and different colors or sizes of the circles or ovals can represent the magnitude of the interaction score or alteration in the interaction score. In some embodiments, results are used to derive an overall metric or index representing the selectivity of the compound with regard to the client proteins.

In general, any chaperone and any client of said chaperone can be used in an inventive assay in various embodiments of the invention. In some embodiments, the chaperone comprises an HSP, e.g., an HSP90, e.g., an HSP90A. In some embodiments, the client comprises a transcription factor, enzyme, receptor, receptor-associated protein, scaffold protein, channel, or signal transduction protein. In some embodiments, the chaperone comprises an HSP90A, and a protein of interest comprises a receptor, transcription factor, mitochondrial protein imported from the cytoplasm, calcineurin, heat shock factor 1 (HSF1), telomerase reverse transcriptase (TERT), endothelial nitric oxide synthase (eNOS), viral protein, myosin, argonaute, leucine rich repeat (LRR) protein, or kinase. In some embodiments, the chaperone comprises an HSP90A, and a protein of interest comprises a repeat or domain selected from: WD40, RCC1 repeat, Kelch, WDAD, NHL repeat, Leucine rich repeat, Kinase domain. In some embodiments, step (a) of the method comprises (i) providing a cell that expresses the chaperone and the protein of interest; and (ii) contacting the cell with the test agent. In some embodiments, step (a) comprises (i) providing a cell that stably expresses the chaperone and transiently expresses the protein of interest; and (ii) contacting the cell with the test agent.

In many embodiments, cells that express a client of interest and a chaperone are contacted with a compound, e.g., by adding the compound to culture medium in which the cells are being cultured. Cells are maintained for a period of time, e.g., in the presence of the cell culture medium, during which time period compound can enter the cell and contact a client protein. Interaction between the client protein and a chaperone or co-chaperone is assessed. In some embodiments, a lysate is prepared from the cells, and a protein-protein interaction assay is performed. For example, a QPPI assay, e.g., a QLPPI assay, of the invention can be performed. Other protein-protein interaction assays can be used in certain of the inventive methods, as discussed below. In some aspects, inventive assays permit the interaction between test agent and client protein to occur in living cells, e.g., cells of the cell type and/or species that naturally express the client protein. Inventive assays can thus reflect the nature of the cellular environment in way(s) that would be difficult or impossible using a cell-free assay system. For example, binding (or alteration in binding) of the test agent to the client can occur in the presence of physiologically appropriate concentrations of molecules that may be relevant to the activity of the client (e.g., ATP) and/or the effect of extracellular or intracellular stimuli on test agent binding can be assessed. Effect of variations in cell type or cell state on the binding of a test agent to a client protein can be assessed. In some embodiments of the invention, if the level of interaction is decreased as compared with the level of interaction that would be expected in the absence of the test agent, then the test agent is identified as a candidate agent for binding to the client protein. In some embodiments of the invention, if the level of interaction is decreased as compared with that which would be expected in the absence of the compound, then the compound is identified as a candidate modulator of the client protein.

In some embodiments, a CCI assay is performed in a cell-free system, using at least partly purified bait and prey proteins. In some embodiments, the bait and/or prey are recombinantly produced. For example, test agent can be contacted with at least partly purified chaperone and client in a noncellular environment.

In general, any test agent can be used in an inventive CCI assay in various embodiments. Test agents of interest are often small molecules. Agents (compounds) can be obtained from natural sources or produced synthetically. Compounds can be at least partially pure or may be present in extracts or other types of mixtures whose components are at least in part unknown or uncharacterized. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multiwell plates (e.g., 384 well plates, 1596 well plates, etc.). They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature, i.e., not naturally occurring) or naturally occurring. In some embodiments, a library comprises at least some compounds that have been identified as "hits" or "leads" in a drug discovery program and/or derivatives thereof. A compound library can comprise natural products and/or compounds generated using non-directed or directed synthetic organic chemistry. In some embodiments, compounds, e.g., peptides, are expressed intracellularly. For example, cDNA libraries encoding random peptides, cyclic peptides, etc., can be introduced into cells and their effect on CCI assessed.

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see mli.nih.gov/mli/). In some embodiments, a compound that is an "approved human drug" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test compound may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or anti-hormonal drug, etc. In some embodiments, a compound is one that has undergone at least some preclinical or clinical development or has been determined or predicted to have "drug-like" properties. For example, the test compound may have completed a Phase I trial or at least a preclinical study in non-human animals and shown evidence of safety and sufficient tolerability to be usable for treatment of subjects, e.g., human subjects. In some embodiments, a panel of approved human drugs is tested. In some embodiments a test compound is a metabolite of a synthetic compound, e.g., a metabolite of an approved human drug. Numerous examples of approved drugs and other compounds, and numerous examples of diseases associated with various proteins of interest (and therapeutic agents useful for treating such diseases), are described in Brunton, L. (ed.), Goodman and Gilman's The Pharmacological Basis of Therapeutics, 12 ed., McGraw-Hill Professional; (2010); Katzung, B., et al., Basic and Clinical Pharmacology, McGraw-Hill/Appleton & Lange; 11th edition (2009); Fauci, et al. (eds.) Harrison's principles of internal medicine, 17th ed. New York: McGraw-Hill, 2008, or previous or subsequent editions of any of the foregoing, in book form or online.

In some embodiments, a test compound is substantially non-toxic to cells of a subject to which the compound may be administered and/or to cells with which the compound may be contacted (in culture or in the body of a subject, at the concentration to be used or, in some embodiments, at concentrations up to 10-fold, 100-fold, or 1,000-fold higher than the concentration to be used. For example, there may be no statistically significant effect on cell viability and/or proliferation, or the reduction in viability or proliferation can be no more than 1%, 5%, or 10% in various embodiments. Cytotoxicity and/or effect on cell proliferation can be assessed using any of a variety of assays. For example, a cellular metabolism assay such as AlamarBlue, MTT, MTS, XTT, and CellTitre Glo assays, a cell membrane integrity assay, a cellular ATP-based viability assay, a mitochondrial reductase activity assay, a BrdU, EdU, or H3-Thymidine incorporation assay could be used. In some embodiments, a test compound is not a compound that is found in a cell culture medium known or used in the art, e.g., culture medium suitable for culturing vertebrate, e.g., mammalian cells or, if the test compound is a compound that is found in a cell culture medium known or used in the art, the test compound is used at a different, e.g., higher, concentration when used in a method of the present invention.

In some embodiments, compounds are tested in a CCI assay at multiple concentrations (e.g., 2-20 different concentrations) and/or in multiple replicates (e.g., 2-20 replicates). In some embodiments, concentrations are between 10 nM and 100 µM, e.g., between 100 nM and 10 µM. Multiple replicates of some or all different concentrations can be performed. In some embodiments, results from performing an assay at multiple different concentrations are used to generate an IC50 value. In some embodiments, compounds are contacted with cells for various different periods of time prior to preparing a lysate. For example, compounds can be contacted with cells for between 30 minutes and 24 hours, e.g., about 1, 1.5, 2, 3, 4, 6, 8, 10, 12, 16, 20, or 24 hours, in various embodiments.

In some embodiments, the protein of interest comprises a kinase and the test agent is a known kinase inhibitor or a candidate kinase inhibitor. In such embodiments, the chaperone is often an HSP90A protein or CDC37 protein. For example, a kinase can be used as bait, and a chaperone can be used as prey, in a QPPI assay, e.g., a QLPPI assay, of the invention. In general, an inventive CCI assay can be used to assess the effect of any agent, e.g., any small molecule kinase inhibitor (or candidate small molecule kinase inhibitor), on interaction of HSP90β and/or CDC37 with a kinase, thereby assessing the effect of the agent on the interaction and/or on the kinase. In some aspects, an inventive CCI assay uses full-length kinases. (In contrast, a number of prior art assays used in testing kinase inhibitors make use of truncated versions, e.g., due to difficulty in purifying full length kinases). In some aspects, an inventive CCI assay is independent of kinase activity (e.g., no substrate is needed, inactive kinases can be tested). In some aspects, an inventive CCI assay permits assaying kinases having native post-translational modifications (e.g., phosphorylation, myristoylation, palmitoylation). In some aspects, an inventive CCI assay allows assaying kinases in their native conformational equilibrium. In some aspects, an inventive CCI assay is compatible with type I, II, and III kinase inhibitors. In some aspects, an inventive CCI assay is compatible with kinases harboring mutations, e.g., oncogenic mutations, drug resistance mutations, translocations. Drug resistance mutations are mutations that arise, e.g., in a subject being treated for cancer with a kinase inhibitor, wherein the mutation renders a tumor that was initially susceptible to therapy with the kinase inhibitor no longer sensitive to such therapy. In general, a tumor may be considered sensitive to therapy if administration of the kinase inhibitor results in regression of the tumor, e.g., an objective response to therapy. A tumor may be considered resistant if it recurs in the presence of therapy or continues to progress in the presence of therapy. Drug resistance mutations are known in the art that render tumors resistant to therapy with various kinase inhibitors. Kinases bearing such mutations can be used in a CCI assay of the invention e.g., to identify compounds that reduce the interaction of the kinase with HSP90A or CDC37, thereby identifying a potentially useful inhibitor of the mutant kinase and/or to predict or assess the resistance or sensitivity of one or more kinase mutants to a kinase inhibitor of interest. For example, in some embodiments, a CCI assay is used to profile a kinase inhibitor against a panel of kinase mutants, e.g., in order to predict resistance or sensitivity of the mutants to the inhibitor. In some embodiments a CCI assay is used in drug discovery efforts aimed at identifying compound(s) that will be effective against mutant kinase(s). In some embodiments the kinases comprise mutant versions of a particular kinase of interest (e.g., a kinase whose aberrant expression or overactivity contributes to cancer). In some embodiments a CCI assay is used to identify a kinase inhibitor that inhibits one or more mutant forms of a kinase, e.g., a kinase inhibitor that inhibits a spectrum of kinase mutants. For example, in some embodiments a CCI assay is used to identify a compound capable of inhibiting one or more mutants that are resistant to inhibition by a particular kinase inhibitor, e.g., mutants that contribute to relapse in a cancer patient treated with the kinase inhibitor. In some embodiments, at least 5, 10, 20, 50, 100, or more mutants of a particular kinase of interest are assessed. Of course the unmutated version of the kinase may also be assessed. In some embodiments a kinase inhibitor capable of inhibiting multiple mutant versions of a kinase of interest is identified using a CCI assay. For example, a CCI assay is used in a screen seeking to identify a kinase inhibitor capable of inhibiting at least 2, 5, 10, 20, 50 or more mutants of a particular kinase. In some embodiments at least some kinase mutants tested are known to arise in subjects treated with a kinase inhibitor. In some embodiments at least some kinase mutants tested are generated by in vitro mutagenesis.

In some embodiments of any assay herein, one or more combinations of compounds are tested or profiled. For example, two or more kinase inhibitors or candidate kinase inhibitors can be tested together in a well. The kinase inhibitors may have the same primary target or different primary targets. Any combination of compounds is encompassed in various embodiments. In some embodiments a profile of a combination of two or more compounds against a panel of kinases is obtained. In some embodiments an assay is used to identify a combination of compounds having a desired profile against a panel of kinases. In some embodiments a combination of two or more kinases that both have activity against one or more target kinases of interest, but that differ with regard to their activity against a range of other kinases, can be advantageously used to inhibit the kinase of interest while having lesser total effect on the other kinases, thereby achieving greater specificity.

In some embodiments of any assay herein, a combination of a kinase inhibitor and a compound ("second compound") that is not known or believed to be a kinase inhibitor is tested. The ability of the second compound to alter, e.g., potentiate or reduce, the effect of the kinase inhibitor on one or more kinases is assessed. In some embodiments the second compound is a compound that is used or contemplated for use to treat the same disease or subject for which the kinase inhibitor is of use. The assay may be used, e.g., to determine whether a second compound may interfere with or potentiate the activity of the kinase inhibitor and/or to identify potentiators of, e.g., a compound of interest, or compounds that interfere with or antagonize activity of the compound of interest. In some embodiments a potentiator may be useful as a component of a combination therapy approach (e.g., for use in a composition together with the compound of interest or administered separately). In some embodiments a compound that antagonizes or interferes with a compound of interest may be avoided in treating a subject with the compound of interest. In some embodiments a potentiator of a compound or interest, or a compound that antagonizes or interferes with a compound of interest, is itself of interest for drug development and/or for treating a disease. In some aspects, an assay described herein is of use to detect drug-drug interactions on a cellular level.

In some aspects, an inventive CCI assay permits assaying kinases and/or kinase inhibitors under conditions of endogenous ATP levels (~1-10 mM). In some aspects, an inventive CCI assay permits assaying kinases and/or kinase inhibitors in the presence or absence of serum. In some aspects, an inventive CCI assay is used to perform IC50 measurements. In some aspects, use of an inventive CCI assay may identify kinase inhibitors that bind to portions of the kinase target that were previously not recognized as being potential binding sites for inhibitors. Without wishing to be bound by any theory, an inventive CCI assay may provide a means of identifying allosteric (type III) inhibitors that bind to novel binding sites.

One of ordinary skill in the art will appreciate that many thousands of small molecule kinase inhibitors that show activity, e.g., in one or more kinase inhibition assays known in the art, have been discovered. Any such kinase inhibitor can be tested in an inventive CCI assay. A vast number of patents, patent applications, and scientific articles have been published that disclose compounds that have been shown to inhibit at least one kinase in a prior art assay. One of ordinary skill in the art would be able to locate the structures of numerous such compound(s) in publicly available patent databases, PubMed, PubChem, etc. In some aspects, any such compound may be tested using an inventive CCI assay. Exemplary kinase inhibitors and kinase targets thereof are discussed, e.g., in Zhang J, et al., Targeting cancer with small molecule kinase inhibitors. Nat Rev Cancer. 9(1):28-39, 2009; Jänne P A, et al., Factors underlying sensitivity of cancers to small-molecule kinase inhibitors. Nat Rev Drug Discov. 8(9):709-23, 2009; Li, R. and Stafford, J A, Kinase Inhibitor Drugs (Wiley Series in Drug Discovery and Development), Wiley, 2009; and/or Matthews, D J and Gerritson, M., supra.

In some embodiments, a kinase inhibitor is a compound known in the art as an inhibitor of at least one tyrosine kinase. In some embodiments, a kinase inhibitor is a compound known in the art as an inhibitor of at least one serine/threonine kinase. In some embodiments, a kinase inhibitor is a compound known in the art as a Type I inhibitor. In some embodiments, a kinase inhibitor is a compound known in the art as a Type II inhibitor. In some embodiments, a kinase inhibitor is a compound known in the art as a Type III inhibitor. In some embodiments, a kinase inhibitor is a compound known in the art as a covalent inhibitor.

In some embodiments, a kinase inhibitor is imatinib, gefitinib, erlotinib, nilotinib, dasatinib, sunitinib, sorafenib, pazopanib, lapatinib, axitinib, brivanib, motesanib, crizotinib, ponatinib, GNF-2, GNF-5, PLX4032, PLX4720, GDC-0879, PD-166326, PD-173955, PD-0332991, DV2-273, MLN8237, GSK1070916A, fostamatinib (R9355788), JNJ-26483327, GW-786034, MLN-518, MLN-8054, MK-2206, VX-680/MK-0457, PTK-787, ZD-6474, AZD1152HQPA, CHIR-258/TKI-258, AST-487, ABT-869, riscovitine, flavopiridol, or a structural analog of any of the foregoing.

It will be understood that an agent, e.g., a kinase inhibitor, may be provided as a salt of the active agent, e.g., a pharmaceutically acceptable salt.

As known in the art, kinase inhibitors may often referred to based on the name of their primary target (and/or one or more secondary target(s)). A primary target may be one that the kinase is known to inhibit with an IC50 of 500 nM or less, e.g., 100 nM or less, in an in vitro kinase assay, and/or may be the first kinase to be recognized as a target of the kinase inhibitor and/or may be an intended target of the kinase. A secondary target may be a subsequently identified target. In some embodiments, a kinase inhibitor is a Src inhibitor. In some embodiments, a kinase inhibitor is an ABL inhibitor. In some embodiments, a kinase inhibitor is a RAF inhibitor, e.g., a RAFB inhibitor. In some embodiments, a kinase inhibitor is a CDK inhibitor. In some embodiments, a kinase inhibitor is a JAK inhibitor. In some embodiments, a kinase inhibitor is a KIT inhibitor. In some embodiments, a kinase inhibitor is a MEK inhibitor. In some embodiments, a kinase inhibitor is a VEGFR inhibitor. In some embodiments, a kinase inhibitor is an EGFR inhibitor. In some embodiments, a kinase inhibitor is an ERBB2 inhibitor. In some embodiments, a kinase inhibitor is an ALK inhibitor. In some embodiments, a kinase inhibitor is a PDGFR inhibitor. In some embodiments, a kinase inhibitor is an Aurora kinase inhibitor. In some embodiments a kinase inhibitor is an mTOR inhibitor. In some embodiments a kinase inhibitor is an FGFR inhibitor.

In some embodiments, a test agent, e.g., a kinase inhibitor, is tested against a panel of kinases, e.g., protein kinases, in a CCI assay. The extent to which the kinase inhibitor decreases interaction between each kinase and the chaperone is measured. In some embodiments, the panel consists of at least 10, 50, 100, 150, or 200 kinases. The resulting data can provide a profile of kinase inhibitor specificity. In some embodiments, kinases are ranked (listed in order) based on the extent to which the compound inhibits their interaction with the chaperone. In some aspects, the information may be used to identify a new target for the kinase inhibitor.

In some embodiments, a kinase, e.g., a protein kinase, is tested against a panel of test agents in a CCI assay. The extent to which interaction between the kinase and the chaperone is decreased as a result of the test agent is measured. The resulting data can provide a profile of kinase sensitivity. In some embodiments, the test agents are ranked based on the extent to which they inhibit kinase interaction with the chaperone. In some aspects, the information may be used to identify a lead compound or scaffold for further optimization as a modulator, e.g., an inhibitor, of the kinase.

In some embodiments, one or more compounds (e.g., a panel of compounds) identified and/or synthesized in a kinase drug discovery effort is tested in an inventive CCI assay against either a particular kinase of interest, or a panel of kinases. In some aspects, use of an inventive CCI assay may identify new targets of known kinase inhibitors. Such information may be useful to, e.g., provide insight into mechanism(s) of therapeutic action attributable to such kinase inhibitor and/or to determine causes of undesired side effect(s). In some aspects, such information may be useful in selecting appropriate subjects to receive treatment with a kinase inhibitor. In some embodiments, identifying a new target of a kinase inhibitor would prompt identification of compounds that specifically inhibit that target. In some embodiments, a compound previously deemed insufficiently active against a particular kinase to warrant further development can be tested, and other target(s) (e.g., new targets) for such compound identified. In some embodiments, a compound that failed to show efficacy in a clinical trial can be tested. Such testing may reveal new targets for such compound(s) and potentially new clinical indications in which such compound(s) may be tested in further clinical trials. In some aspects, kinase inhibitors having a desired spectrum of activity (e.g., highly specific for a particular target or inhibiting multiple selected targets) may be identified.

In some aspects, identification of a new target for a kinase inhibitor can suggest a scaffold (e.g., the scaffold on which that kinase inhibitor is based) for further optimization against that target.

In some aspects, clinical response in patients can be explained by mutation-specific effects (e.g. as has been demonstrated for various EGFR inhibitors and BRAF inhibitors). An inventive assay may be used to determine the spectrum of mutant forms of a kinase amenable to inhibition by a particular kinase inhibitor of interest, which may help determine the basis for response or lack thereof. Tumors may be tested to determine whether they harbor a sensitive allele. Subjects having such tumors may be treated with the inhibitor if the tumor harbors a sensitive allele.

As noted above, kinase inhibitors are of use in the treatment of cancer, and assays described herein (CCI and/or QLPPI assays) are of use to identify, characterize, select, or profile kinase inhibitors for such use. In addition to cancer, a number of other diseases are caused at least in part by aberrantly increased activity of one or more kinases. (See, e.g., Lahira, P., et al., (2010) Nature Reviews Genetics 11, 60-74, see, e.g., Table 1). For example, gain-of-function mutations are associated with a number of inherited or sporadic disorders affecting, e.g., the skeletal, haematological, vascular, endocrine and/or metabolic system. In some embodiments, a kinase inhibitor is used to treat any such disease. In some embodiments a disease is caused by an autosomal dominant mutation. In some embodiments a CCI and/or QLPPI assay is used to identify, characterize, select, or profile a kinase inhibitor for use in treating one or more such diseases.

In some aspects, one or more known or candidate protein kinase activators are tested in a CCI assay. For example, in some embodiments a method of characterizing a compound comprises (a) providing a composition that comprises a compound, a chaperone, and a kinase client of the chaperone; (b) measuring the interaction between the chaperone and the kinase in the composition; and (c) comparing the level of interaction measured in step (b) with the level of interaction expected in the absence of the compound, wherein the compound is a kinase activator. In some embodiments a profile of the ability of the kinase to activate a panel of kinases is obtained. In some embodiments multiple kinase activators or candidate kinase activators are tested to identify one or more compounds that activate(s) a kinase of interest or does not activate a kinase of interest or has a profile of interest. In some aspects, use of an inventive CCI assay may identify new targets of known kinase activators or to identify new kinase activators. In some embodiments, a CCI assay is used to profile a kinase activator against a panel of kinase mutants, e.g., in order to predict the extent to which the mutants are activatable by the activator. In some embodiments the mutants are mutant versions of a particular kinase of interest. In some embodiments a CCI assay is used to identify a kinase activator that activates one or more mutant forms of a kinase, e.g., a kinase mutant that is associated with a kinase deficiency disorder. For example, it may be of interest to identify a compound capable of activating one or more mutants that have decreased function in a disease. A variety of kinase activators are known in the art. In some embodiments a kinase activator is DHP (5-[3-(4-fluorophenyl)-1-phenyl-1H-pyrazol-4-yl]-2,4-imidazolidinedione or 5-(1,3-diary)-1H-pyrazol-4-yl)hydantoin)) or an analog thereof (Yang, J., et al. Chem Biol. (2011) 18(2):177-86). DPH is a cell-permeable small molecule c-Abl activator that binds to the myristoyl binding site of c-Abl and is thus an allosteric modulator. In some embodiments a kinase activator is MLR-1023 (a LYN kinase activator). Other kinase activators are disclosed, e.g., in Simpson et al., Curr. Opin. Drug Discov. Dev., 12 (2009), pp. 585-596, and references therein, which are incorporated herein by reference.

Kinase activators are useful for a variety of purposes. In some embodiments a kinase activator is used as a tool to gain insight into the physiological and pathological roles of the kinase(s) that it activates and/or their signaling pathway(s). In some embodiments a kinase activator is used in a cell culture system. In some embodiments a kinase activator is used in a (non-human) animal model, e.g., an animal model of a disease in which kinase activation plays a role (e.g., cancer or any other of the various diseases associated with elevated kinase activity). For example, a kinase activator may be administered as an alternative to identifying or generating a non-human animal that has aberrantly increased kinase activity.

In some embodiments a kinase activator is used to treat a disease. A number of diseases are caused at least in part by a deficiency of kinase activity (see, e.g., Lahira, P., et al., (2010) Nature Reviews Genetics 11, 60-74, see, e.g., Table 1). A deficiency in kinase activity may result, e.g., from a loss-of-function mutation (e.g, which may result in total or partial loss of function) in a kinase gene or may result from presence of a defective kinase that interferes with function of a normal kinase (e.g., as a dominant negative). In general, a loss-of-function mutation can be a deletion, insertion, rearrangement, or any other type of genetic alteration that results in reduced amount and/or activity of a gene product. In some embodiments a kinase deficiency disorder shows an autosomal recessive inheritance patterns. Examples of kinase deficiency disorders include a number of (1) neurological diseases, which include various degenerative and encephalopathic disorders (e.g., lethal congenital contracture syndrome type 2 (LCCS2)), epilepsies, myasthenia and ataxia (e.g., spinocerebellar ataxia); (ii) immunological disorders such as example, Bruton X-linked agammaglobulinemia; (iii) endocrine/metabolic disorders such as hypogonadotrophic hypogonadism In some embodiments a kinase activator is used to treat a kinase deficiency disorder. For example, a kinase activator may be used to increase activity of a kinase encoded by a normal allele in situations where the other allele is defective and/or may be used to increase activity of a kinase encoded by a mutant allele (e.g., a loss-of-function allele), wherein the kinase has, e.g., reduced kinase activity or reduced stability or wherein a reduced amount of the kinase is produced (e.g., due to a mutation in a regulatory region). In some embodiments a kinase activator activates an insulin receptor (or downstream kinase in the insulin signaling pathway), ERBB3, PRKCG, FGFR2, FGFR3, LYN, or RET. Human RET loss-of-function mutations and/or Ret disruption in mice have been associated with Hirschsprung disease, renal agenesis, and central hypoventilation syndrome. In some embodiments a kinase activator potentiates insulin signaling and is of use, e.g., to treat diabetes (e.g., Type II), metabolic syndrome, or any disorder resulting at least in part from deficient insulin signaling. In some embodiments a kinase activator is used to treat a cancer that results at least in part from a loss-of-function mutation in a kinase that normally acts as a tumor suppressor.

Data suggests a role for c-Abl activation in inhibiting mammary tumorigenesis and breast cancer cell mobility and invasiveness. In some embodiments an activator of c-Abl is used to inhibit development or progression or recurrence of a tumor, e.g., a mammary tumor. c-Abl has been implicated as playing an important role in maintaining normal myelopoiesis. In some embodiments an activator of c-Abl is used to treat leukopenia, e.g., neutropenia. In general, leukopenia can result from a decrease in the production of white blood cells (WBCs) by the bone marrow and/or destruction of the cells elsewhere in the body, either of which can be due to a variety of causes. For example, certain medications (e.g., cancer chemotherapy; immunosuppressive drugs, and a variety of others), radiation therapy, infections, autoimmune diseases, hereditary disorders (e.g. congenital neutropenia, cyclic neutropenia) can result in leukopenia.

In some embodiments a kinase activator is used to at least in part counteract a kinase inhibitor. For example, certain kinase inhibitors, in addition to inhibiting a desired kinase target (e.g., a kinase whose inhibition is therapeutically useful) also inhibit one or more additional kinases, the inhibition of which may result in harmful or unpleasant side effects. Such side effects may in some instances be dose-limiting. In some embodiments, administration of a kinase activator that activates such "off-target" kinases while having substantially less or no activating effect on the desired target of the kinase inhibitor reduces one or more side effects of the kinase inhibitor. In some embodiments, a reduction in side effect(s) of the kinase inhibitor allows use of a higher, and potentially more efficacious, dose of the kinase inhibitor. In some embodiments at least one kinase inhibitor and at least one kinase activator are tested together in a CCI assay. In some embodiments a composition comprising at least one kinase inhibitor and at least one kinase activator is profiled with respect to a panel of kinases using a CCI assay. In some embodiment a combination of kinase inhibitor(s) and kinase activator(s) that together result in an improved kinase inhibition or kinase activation profile is identified. In some embodiments, an "improved profile" is one that more closely achieves one or more intended goal(s). In some embodiments an improved profile a more specific inhibition profile. In some embodiments an improved profile a more specific activation profile.

Any of a variety of different methods for detecting protein-protein interactions can be used in the inventive CCI methods to detect and/or measure an interaction between a chaperone and a client in the presence of an agent of interest. In many embodiments, an inventive method for detecting and/or quantitating protein-protein interactions described in Section II hereof is used. However, any of a number of other methods for detecting and/or measuring protein-protein interactions can be used in various embodiments. Examples of PPI assays include a variety of different assays sometimes termed "protein fragment complementation assays" (PAC), in which a reporter molecule (typically a protein) capable of generating a detectable signal is reconstituted as a result of interaction between proteins of interest, each of which comprises a fragment of the reporter molecule, often at the N- or C-terminus. Reconstitution of the reporter molecule results, e.g., in a protein that can be directly or indirectly detected. Fragments are selected that produce no or low signal by themselves and have low affinity for each other but have the capacity to reassemble to form a detectable reporter molecule when brought into proximity. The sequence of a fragment of a reporter molecule can be altered to, e.g., reduce spontaneous assembly of the fragments. Examples of PCAs include enzyme complementation assays, fluorescence complementation assays, luciferase complementation assays, and protease complementation assays. Exemplary reporter proteins of use in PCAs include enzymes such as dihydrofolate reductase and β-lactamase; fluorescent proteins such as green fluorescent protein (GFP) and variants thereof; and luciferases such as firefly luciferase, *Gaussia* luciferase, and *Renilla* luciferase. The split tobacco etch virus (TEV) protease assay is an exemplary protease complementation assay. In other embodiments, a resonance energy transfer assay (e.g., a FRET or BRET based assay) is used to detect and/or measure a protein-protein interaction between a chaperone and a client in the presence of a test agent.

While use of the inventive CCI assays for identifying and/or characterizing small molecule kinase inhibitors is exemplified in most detail herein, the invention encompasses use of CCI assays for identifying and/or characterizing modulators of any client protein of interest. In some embodiments, the client protein is a receptor. In some embodiments, the receptor is a nuclear receptor (NR). A significant focus in current efforts directed to the discovery of drugs that target NRs is identifying drugs with the potential for reduced side effects by improving selectivity, e.g., among different NRs and/or by selective modulation of the NR of interest. In some aspects, the invention provides methods wherein the effect of a small molecule on chaperone or co-chaperone interaction with an NR is assessed under different conditions and/or in different cell types, and compound(s) that selectively modulate NR activity are identified. In some embodiments, a chaperone-client interaction assay is used to identify and/or characterize compound(s) useful for modulating NR activity. For example, an inventive QPPI assay, e.g., a QLPPI assay, can be performed using an HSP, e.g., HSP90A or HSP70, or an FKBP as a prey proteins and members of a panel of NRs as bait proteins. Cells are contacted with test compounds. Compounds that selectively alter interaction between one or more NRs and a HSP, e.g., HSP90A or HSP70, or FKBP may be identified and/or compounds that alter interaction between one or more NRs of interest only under certain conditions or in certain cell types may be identified using a chaperone-client interaction assay.

In some embodiments an agent, e.g., a test agent, is a ligand for at least one ligand-dependent TF, e.g., a ligand-dependent nuclear receptor, e.g., a steroid hormone receptor. In some embodiments a steroid receptor ligand comprises a steroid. In some embodiments a steroid receptor ligand comprises a compound that is not a steroid. In some embodiments a steroid is a glucocorticoid (GC), estrogen, or androgen. Exemplary GCs include cortisone, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, fluticasone, fluticasone furoate, and fluticasone propionate. In some embodiments, a GR agonist is a selective glucocorticoid receptor agonist (SEGRA). In some embodiments, a "SEGRA" is a GR agonist that has reduced transactivation activity or reduced transrepression activity of genes whose activation is at least in part responsible for deleterious side effects associated with administration of certain GC, e.g., prednisone or dexamethasone. See, e.g., Schacke, H, et al., "Selective glucocorticoid receptor agonists (SEGRAs): novel ligands with an improved therapeutic index." Molecular and cellular endocrinology 275 (1-2): 109-17; Rehwinkel, H and Schacke H., GR ligands: can we improve the established drugs. Chem Med Chem. (8):803-5 (2006). Exemplary androgens include, e.g., testosterone, oxandrolone, fluoxymesterone, and nandrolone. Exemplary progestins include, e.g., progesterone, norethindrone, medroxyprogesterone. Exemplary naturally occurring estrogens include, e.g., estrone (E1), estradiol (E2), and estriol (E3), while an exemplary synthetic estrogen is diethylstilbestrol (DES). Various synthetic and natural substances have been identified that possess estrogenic activity. For example, plant products with estrogenic activity are sometimes called phytoestrogens, while those produced by fungi are sometimes called mycoestrogens.

In some embodiments an agent is a ligand that displays an agonist response in some tissues and an antagonistic response or substantially no response in other tissues that express the receptor. In some embodiments, such a compound may retain one or more desired beneficial therapeutic effects while minimizing or reducing one or more undesirable side effects. Compounds with such a mixed agonist/antagonist profile of action may be referred to as selective receptor modulators (SRMs). Examples include selective androgen receptor modulators (SARMs), selective estrogen receptor modulators (SERMs), and selective progesterone receptor modulators (SPRMs). Such compounds find use in treating a variety of different diseases. For example, selective estrogen receptor modulators (SERM's) include a class of hormonal therapy agents which act as antagonists of the estrogen receptor and are used, e.g., for the treatment and chemoprevention of breast cancer. Some members of this family, such as tamoxifen, are actually partial agonists, which can actually increase estrogen receptor signalling in some tissues, such as the endometrium. Raloxifene is another partial agonist SERM that is used, e.g., for chemoprevention of breast cancer, e.g., in high-risk individuals, as well as to prevent osteoporosis. Toremifene and fulvestrant are SERM's with little or no agonist activity, and are used for treatment of metastatic breast cancer. Antiandrogens are a class of drug which bind and inhibit the androgen receptor, blocking the growth- and survival-promoting effects of testosterone on certain prostate cancers. Flutamide and bicalutamide are antiandrogens which are frequently used in the treatment of prostate cancer.

In some aspects, a CCI assay permits assaying ligand-dependent TFs and/or ligands of ligand-dependent TFs, under conditions in a physiologically relevant environment, e.g., a cellular environment in which endogenous proteins that naturally interact with such ligand-dependent TFs are present.

In some embodiments, a test agent, e.g., a kinase inhibitor, is tested against a panel of kinases, e.g., protein kinases, in a CCI assay. The extent to which the kinase inhibitor decreases interaction between each kinase and the chaperone is measured. In some embodiments, the panel consists of at least 10, 50, 100, 150, or 200 kinases. The resulting data can provide a profile of kinase inhibitor specificity. In some embodiments, kinases are ranked (listed in order) based on the extent to which the compound inhibits their interaction with the chaperone. In some aspects, the information may be used to identify a new target for the kinase inhibitor.

In some embodiments, a NR is tested against a panel of test agents in a CCI assay. The extent to which interaction between the NR and the chaperone is decreased as a result of the test agent is measured. The resulting data can provide a profile of kinase sensitivity. In some embodiments, the test agents are ranked based on the extent to which they inhibit NR interaction with the chaperone. In some aspects, the information may be used to identify a lead compound or scaffold for further optimization as a modulator of the NR. In some embodiments, one or more compounds (e.g., a panel of compounds) identified and/or synthesized in a ligand drug discovery effort is tested in an inventive CCI assay against either a particular NR of interest, or a panel of NR. In some aspects, use of an inventive CCI assay may identify new targets of known NR modulators. Such information may be useful to, e.g., provide insight into mechanism(s) of therapeutic action attributable to such NR modulator and/or to determine causes of undesired side effect(s) and/or to identify additional therapeutic indications for such NR modulator. In some aspects, such information may be useful in selecting appropriate subjects to receive treatment with a NR modulator. In some embodiments, a compound previously deemed insufficiently active against a particular NR to warrant further development is tested. In some embodiments other target(s) (e.g., new targets) or appropriate cell types for use of such compound are identified. In some embodiments, a compound that failed to show efficacy in a clinical trial can be tested. Such testing may reveal new targets for such compound(s) and potentially new clinical indications in which such compound(s) may be tested in further clinical trials. In some aspects, NR modulators having a desired spectrum of activity (e.g., highly specific for a particular target or modulating multiple selected targets or having different effects in different cell types) may be identified.

In some embodiments, an inventive assay is used to identify compounds that have similar activity and/or specificity to that of a selected compound of interest and/or that differ in one or more ways with regard to activity and/or specificity as compared with a selected compound of interest. For example, a compound can be profiled against a panel of proteins (e.g., kinases, NRs). One or more additional compounds are profiled against substantially the same panel. The resulting profiles are compared to identify compound(s) that have similar activity and/or specificity as the selected compound. Compounds that exhibit a similar profile of activity and/or specificity to those of the selected compound of interest are candidate therapeutics for treating disease(s) that can be treated using the compound of interest. Identified compound(s) that have (i) increased activity towards one or more target(s) whose inhibition is expected to be or has been determined to be beneficial; (ii) reduced activity toward one or more targets whose inhibition has been determined to be or expected to be deleterious; and/or (iii) increased selectivity may be identified.

In some embodiments one or more assays described herein is used to test or profile any compound of interest, e.g., a compound under consideration or in development or use for treatment of a disease, for use as a component of food, supplement, cosmetic, personal care product, pesticide, herbicide, etc., or any compound to which mammals, e.g., humans, are or may potentially be exposed in the environment (e.g., as a pollutant, a chemical used in manufacturing, etc.) The assay may be used to detect potential effects of the compound on one or more proteins, e.g., one or more kinases, GPCRs, NRs, TFs, etc. In some embodiments an assay is used in preclinical screening, e.g., preclinical toxicology screening, wherein it may be desirable to identify at a relatively early stage of development, compounds that have potential for significant off-target effects, which may be undesired or may suggest additional potential uses. In some embodiments an assay is used to elucidate mechanism of action of a compound or mechanism of unwanted side effect of a compound. For example, compounds of interest may be identified in phenotypic or functional screens, where the mechanism of action of the compound and/or the target of the compound is unknown. In some embodiments an assay described herein is used to identify one or more potential targets of the compound. Identification of a target may, for example, facilitate development of more potent analogs.

In some aspects, the identification of a new target kinase of a kinase inhibitor is followed by testing of structural analogs of the kinase inhibitor and/or by design of additional compounds based on the same pharmacophore or scaffold, which new compounds are then tested in a CCI assay or in a different assay, as candidate inhibitors of the kinase. An additional compound may, for example, have one or more improved pharmacokinetic and/or pharmacodynamic properties as compared with a first compound may simply have a different structure. An "improved property" may, for example, render a compound more effective or more suitable for one or more purposes, e.g. for treating a disease. In some embodiments, for example, a compound may have higher affinity for the target of interest, lower affinity for a non-desired target, greater solubility (e.g., increased aqueous solubility), increased stability (e.g., in blood, plasma, and/or in the gastrointestinal tract), increased half-life in the body, increased bioavailability (e.g., increased oral bioavailability) and/or reduced side effect(s), etc. Optimization can be accomplished through empirical modification (e.g., synthesizing compounds with related structures and testing them in cell-free or cell-based assays or in non-human animals) and/or using computational approaches. Such modification can in some embodiments make use of established principles of medicinal chemistry to predictably alter one or more properties. In some embodiments, one or more compounds that are subjected to systematic structural alteration to create a second library of compounds (e.g., refined lead compounds) structurally related to the hit. The second library can then be screened using any of the methods described herein. Analogous methods may be employed in regard to other client proteins and/or other new targets identified as described herein.

In some embodiments, an inventive method is used to identify an agent that selectively modulates, e.g., selectively inhibits, one or more protein(s), as compared with one or more other protein(s) having a closely related sequence or structure. For example, in some embodiments, an inventive method may be used to identify an agent that selectively modulates, e.g., selectively inhibits, one or more protein(s) encoded by particular allele(s) of a gene, as compared with protein(s) encoded by one or more other allele(s) of that gene. Examples of alleles of numerous genes can be found in, e.g., the Single Nucleotide Polymorphism Database (dbSNP) (available at the NCBI website at www.ncbi.nlm-.nih.gov/projects/SNP/), which contains single nucleotide polymorphisms (SNPs) as well as other types of variations (see, e.g., Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). In some embodiments an allelic variant is associated with a disease or with protection from a disease (e.g., individuals who are heterozygous and/or homozygous for the allele have an increased or decreased likelihood of developing the disease, respectively, as compared with individuals not harboring that allele). In some embodiments an allelic variant is associated with an altered response to an agent, e.g., a therapeutic agent (e.g., individuals who are heterozygous and/or homozygous for the allele and have the disease have an increased or decreased likelihood that the therapeutic agent will be effective in treating the disease and/or have an have an increased or decreased likelihood that the therapeutic agent will cause a side effect, e.g., an unwanted side effect).

As known in the art, some proteins exist in various isoforms encoded by the same gene. Such isoforms may arise, e.g., as a result of alternative splicing, alternative promoter usage, and/or alternative initiation sites of translation. In some embodiments, an inventive method is used to identify an agent that selectively modulates, e.g., inhibits, one or more isoform(s) of a protein, as compared with one or more other isoform(s) of the protein. Certain isoform(s) may be expressed in a tissue-specific or developmental stage-specific manner. It may be of interest to selectively modulate, e.g., selectively inhibit, an isoform expressed in particular tissue(s) and/or particular developmental stage(s) while, e.g., having less effect or essentially no effect on activity of isoform(s) expressed in other tissue(s) or on isoform(s) that are co-expressed with a developmental stage-specific isoform. Certain isoform(s) may participate in one or more physiological process(es) or biochemical pathway(s), while other isoform(s) may be involved in other process. It may be of interest to selectively modulate, e.g., inhibit an isoform that participates in one or more physiological process(es) or biochemical pathway(s), while having less or essentially no effect on activity of isoform(s) that participate in one or more other physiological process(es) or biochemical pathway(s). Certain isoform(s) may be associated with a disease. For example, cancer cells often express particular isoform(s) that promote growth and/or survival or otherwise contribute to the disease. It may be of interest to selectively modulate, e.g., selectively inhibit, one or more isoform(s) associated with a disease while having less effect or essentially no effect on activity of isoform(s) that are not associated with the disease. Isoform-selective agents may be effective therapies for the disease while allowing the non-disease-associated isoform(s) to continue to fulfill their normal function, thus reducing unwanted side effects. In some embodiments, an inventive method is used to identify an agent that selectively modulates, e.g., selectively inhibits, one or more disease-associated isoform(s) of a protein, as compared with one or more other isoform(s) of the protein. In some embodiments, an allele, isoform, or mutation is associated with a disease.

In some embodiments a method comprises performing a CCI assay in cells of at least two different cell types using the same protein of interest and using the same agent as a test agent. In some embodiments a method comprises comparing results of the assays performed in at least two different cell types. In some embodiments a method comprises identifying or characterizing an agent that differentially affects a CCI interaction in different cell types. In some embodiments a method comprises identifying or characterizing a compound that acts as a ligand of a protein of interest in one or more cell types while having substantially less or no ability to bind to the protein of interest in one or more other cell types. For example, one cell type may be a cell type that naturally expresses the protein of interest, and in which modulating the protein of interest is of use for treating a disease. A second cell type may be a cell type that naturally expresses the protein of interest, and in which modulating the protein of interest is not useful for treating the disease, and may result in undesired side effects. In some embodiments a method comprises identifying or characterizing a compound that acts as an agonist or antagonist of a protein of interest (e.g., a receptor, e.g., a ligand-dependent TF) in one or more cell types while having substantially less or no activity (e.g., agonist or antagonist activity) towards the protein of interest in one or more other cell types. In some embodiments the method is of use to identify or characterize a selective receptor modulator.

In some embodiments, a compound identified as a candidate modulator, e.g., inhibitor, of a client of interest can be tested in further assays to confirm it as such. In general, the confirmatory assays to be used will depend on the particular client. For example, if a client is a kinase, an in vitro kinase assay can be performed in some embodiments. A compound can be contacted with cells, and the ability of the compound to inhibit autophosphorylation of a target kinase can be assessed. An antiphosphotyrosine antibody can be used to detect tyrosine phosphorylation, for example. In some embodiments, cells are dependent on a kinase for growth. A compound can be contacted with cells, and the ability of the compound to inhibit growth of the cells can be assessed. Different concentrations can be tested and a dose response observed. A compound can be administered to a non-human animal model of a disease, e.g., a disease with which the particular kinase is associated. For example, a wide variety of mouse tumor models are known. Such models include, e.g., xenograft tumor models, models based on injection of tumor cells, a genetically engineered non-human mammal, e.g., a mouse, that has a predisposition to develop tumors. The mammal may overexpress an oncogene (e.g., as a transgene) or underexpress a tumor suppressor gene (e.g., the animal may have a mutation or deletion in the tumor suppressor gene). In some embodiments, e.g., if a client comprises a nuclear receptor, an assay comprises a reporter assay or DNA binding assay. For example, the ability of a candidate modulator to increase or inhibit binding of a nuclear receptor or other TF to its DNA binding site may be assessed, and/or the ability of a candidate modulator to increase or decrease transcriptional activation or repression of a reporter gene comprising a regulatory region that comprises a binding site for the NR or other TF, operably linked to a sequence that encodes a reporter molecule. In some embodiments a compound, e.g., a candidate modulator of an NR or other TF, is contacted with cells that express the NR or other TF, and the ability of the compound to modulate expression of the reporter gene (e.g., as compared with expression of the reporter gene in the absence of the candidate modulator) is assessed. In some embodiments an assay comprises determining whether a candidate modulator is an activator or inhibitor of a protein of interest.

In some embodiments, an inventive assay, e.g., an inventive CCI assay, may be used together with one or more other assays and/or data obtained by performing a CCI assay of the invention may be combined, analyzed, or provided together with data obtained using one or more other assays. For example, an inventive CCI assay used to characterize, e.g., to profile, kinase(s) and/or kinase inhibitor(s) may be used together with one or more kinase or kinase inhibitor characterization or profiling assays and/or data obtained by performing a CCI assay of the invention may be combined, analyzed, or provided together with data obtained using one or more other assays for characterizing and/or profiling kinase(s) and/or kinase inhibitor(s). Briefly, such assays include a variety of activity-based assays (e.g., based on measuring kinase activity and/or ATP depletion), indirect assays, and a few in vivo assays. See, e.g., Ma, H., et al., 3(6) 607-621, 2008 and Smith, L A and Collins, I., J. Biol. Chem. 2:131-151, 2009, for reviews. Commercial platforms include the Ambit KINOMEscan profiling technology (Fabian, M. A., et al. Nature Biotechnol. 23, 329-336, 2005; Federov, O., et al. Proc. Natl. Acad. Sci. USA 104(51), 20523-20528, 2007; Karaman, M. W., et al., Nature Biotechnol. 26, 127-132, 2008); the ActivX KiNativ (Patricelli, M. P. et al., Biochemistry, 46(2), 350-358, 2007), KinaseProfiler (Millipore), Transcreener™ FP assay, DiscoveRx's HitHunter™ Assay, Invitrogen's Far-Red PolarScreen™ FP Assay, Millipore's KinEASE™ Assay, etc. In some aspects, a CCI assay of the invention provides information that complements information available from one or more such assays.

In some aspects, an inventive CCI assay may be performed as a service. In some aspects, the invention provides a method comprising (a) receiving a compound of interest or information including the identity of a compound of interest from a requestor or a representative of the requestor; (b) performing a CCI assay against a panel of potential target proteins (e.g., kinases, ligand-dependent TFs) using the compound; and (c) reporting at least some results of the assay to the requestor or representative of the requestor. In some embodiments, information received from the requestor or representative of the requestor includes information specifying one or more potential target protein(s). In some embodiments, multiple compounds of interest are used in the method. In some embodiments, results include a list or other representation of target proteins ranked based on the extent to which their interaction with a chaperone is modulated by the compound of interest. In some embodiments the multiple potential target proteins include multiple mutant versions of a protein of interest. In some embodiments the protein of interest is a kinase. In some embodiments the kinase is associated with a disease, e.g., cancer. For example, aberrant expression or aberrant activity (e.g., increased activity) is at least in part causative of cancer.

In some aspects, the invention provides a method comprising (a) receiving a protein of interest or information that includes the identity of a protein of interest from a requestor or a representative of the requestor; (b) performing a CCI assay using the protein of interest as a client protein, wherein the CCI assay is performed in the presence of members of a panel of compounds; and (c) reporting at least some results of the assay to the requestor or representative of the requestor. In some embodiments, information received from the requestor or representative of the requestor includes information specifying one or more compound(s). In some embodiments, the results include identity of one or more compound(s) identified as modulator(s) of the protein of interest. In some embodiments, results include a list or other representation of compounds ranked based on the extent to which they modulate interaction between the chaperone and the protein of interest.

In some embodiments, results include one or more interaction scores. In some embodiments, results include the extent to which one or more interaction scores is altered in the presence of a compound as compared with the interaction score in the absence of the compound. In some embodiments, interaction scores are used to produce a map, graph, tree, or other representation of the data. In some embodiments, one or more IC50 values are provided.

In some embodiments, one or more test compound(s) and one or more protein(s) of interest (or information specifying such test compound(s) and/or protein(s) of interest) are provided by the requestor or representative of the requestor. CCI assay(s) are performed, and results are reported.

In some embodiments, receiving and/or reporting information or results comprises transmitting information or results electronically, e.g., over the Internet. In some embodiments, information and/or results are transmitted telephonically and/or in hard copy format (e.g., on a computer-readable medium). Any one or more methods or combination of methods of submitting, transmitting, and/or reporting information can be used in various embodiments.

In some embodiments, an inventive CCI assay is used to generate a database containing information, e.g., profiles, of multiple compounds and/or multiple client proteins. For example, the database may comprise at least 10,000 interaction scores, e.g., at least 100,000 interaction scores, at least 1,000,000 interaction scores, or more. The database may be searchable based on, e.g., compound name, identifier, structure, indication; client or chaperone protein name, sequence, accession number, etc.; cell type, etc. The database may be accessible over the Internet, optionally requiring entry of a password for access.

In some embodiments results of a CCI assay, QLPPI assay, or screen are stored on a computer-readable medium, e.g., ROM, flash memory, CD, DVD, magnetic media (e.g., tape), optical media, memory stick, etc. In some embodiments a method comprises performing a CCI assay, QLPPI assay, or screen using a CCI assay or QLPPI assay and storing at least some of the results on a computer-readable medium. In some embodiments a computer program is used to access, analyze, or display results of a CCI assay, QLPPI assay, or screen. Such analysis may include, for example, ranking compounds, ranking kinases, calculating IC50 values, generating representations such as plots or graphs, etc.

In some embodiments results include a profile of interaction scores, e.g., inhibition scores, for a panel of mutant kinases in the presence of a kinase inhibitor or activator of interest. In some embodiments results include a profile of resistance/sensitivity of a panel of mutant kinases to a kinase inhibitor or activator of interest. In some embodiments a panel of mutant kinases includes multiple mutants of a kinase of interest, e.g., at least 5, 10, 20, 50, 100, or more mutants.

In some embodiments results include a profile of interaction scores for a panel of allelic variants of a protein of interest in the presence of a modulator or candidate modulator of interest. In some embodiments results include a profile of a panel of allelic variants with respect to a modulator or candidate modulator of interest. In some embodiments a panel of allelic variants includes at least 5, 10, 20, or more allelic variants. In some embodiments a method is of use to identify allelic variants that may be associated with a pharmacological activity, therapeutic efficacy, side effect, toxicity, etc. In some embodiments such information is of use, e.g., to identify appropriate subjects for treatment with a therapeutic agent (e.g., subjects who are likely to benefit from the agent) and/or to identify subjects who are at increased risk of experiencing an adverse effect from exposure to an agent, and/or to identify subjects who may require dose adjustment. In some embodiments a method is of use to identify agents that may have or lack a pharmacological activity, therapeutic efficacy, side effect, toxicity, etc., in subject expressing an allelic variant. In some embodiments such information is of use, e.g., to identify appropriate subjects for treatment with a therapeutic agent (e.g., subjects who are likely to benefit from the agent) and/or to identify subjects who are at increased risk of experiencing an adverse effect from exposure to an agent, and/or to identify subjects who may require dose adjustment.

IV. High Throughput Screens

In various embodiments, methods (assays) of the invention are amenable to high-throughput screening (HTS) implementations. In some embodiments, screening assays of the invention are high throughput or ultra high throughput (see, e.g., Fernandes, P. B., Curr Opin Chem Biol. 1998, 2:597; Sundberg, S A, Curr Opin Biotechnol. 2000, 11:47). High throughput screens often involve testing large numbers of compounds with high efficiency, e.g., in parallel. In the context of the instant invention, HTS implementations may comprise testing hundreds of proteins for potential interactions and/or testing hundreds of compounds for their potential effect on one or more interactions, e.g., testing thousands of potential interactions. For example, tens or hundreds of thousands of compounds and/or interactions can be screened in short periods of time, e.g, hours to days, in certain embodiments. In some embodiments, HTS refers to testing of between 1,000 and 100,000 compounds or potential interactions per day. In some embodiments, ultra high throughput refers to screening in excess of 100,000 compounds and/or potential interactions per day, e.g., up to 1 million or more compounds per day.

In some embodiments, screening assays of the invention may be carried out in a multi-well format, for example, a 96-well, 384-well format, 1,536-well format, or 3,456-well format and are suitable for automation. In some embodiments, each well of a microwell plate can be used to run a separate assay against a different test compound, or, if concentration or incubation time effects are to be observed, a plurality of wells can contain test samples of a single compound, with at least some wells optionally being left empty or used as controls or replicates. Typically, HTS implementations of the assays disclosed herein involve the use of automation. In some embodiments, an integrated robot system including one or more robots transports assay microwell plates between multiple assay stations for compound, cell and/or reagent addition, mixing, washing, and/or incubation, and/or for readout or detection. In some aspects, an HTS system of the invention may prepare, incubate, and analyze many plates simultaneously. Suitable data processing and control software may be employed.

In general, high throughput screening implementations approaches are well known in the art. Without limiting the invention in any way, certain general principles and techniques that may be applied in embodiments of a HTS of the present invention are described in Macarrón R & Hertzberg R P. Design and implementation of high-throughput screening assays. Methods Mol Biol., 565:1-32, 2009 and/or An W F & Tolliday N J., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser.

V. Identification of New Targets of Kinase Inhibitors

In some aspects, the invention provides newly identified kinase targets of a variety of kinase inhibitors, e.g., GNF-2, PLX4032, PLX4720, crizotinib, or GDC-0879. Table 2 lists kinases that were stabilized in vivo by inhibitor treatment, as assessed using a quantitative CCI assay of the invention (an HSP90β interaction assay was used). Kinases are ordered by the amount of decrease in HSP90β interaction upon inhibitor treatment (i.e., kinases at the top of the lists were the most significantly affected). Kinases for which at least the wild type form of the kinase had been previously identified by others as targets of the respective kinase inhibitors are listed in bold font. Kinases that (as far as the inventors are aware) had not been previously identified as targets of the respective kinase inhibitors are listed in regular (non-bold) font. Each such kinase listed in regular font may be referred to herein as a "newly identified target" of the respective kinase inhibitor under which it is listed. (It is noted that a number of the mutant kinases listed may also be newly identified targets.) The respective kinase inhibitor may be referred to as a "newly identified inhibitor" of the kinases listed beneath it in regular font.

In some aspects, the invention provides a method of inhibiting a kinase, the method comprising the step of: contacting the kinase with GNF-2, PLX4032, PLX4720, crizotinib, or GDC-0879, wherein the kinase is a newly identified target of GNF-2, PLX4032, PLX4720, crizotinib, or GDC-0879, respectively, listed in Table 2. In some aspects, the invention provides a method of inhibiting a kinase, the method comprising the step of: contacting the kinase with a structural analog of GNF-2, PLX4032, PLX4720, crizotinib, or GDC-0879, wherein the kinase is a newly identified target of GNF-2, PLX4032, PLX4720, crizotinib, or GDC-0879, respectively, listed in Table 2, and wherein the structural analog binds to said newly identified target, e.g., in a substantially similar manner as does GNF-2, PLX4032, PLX4720, crizotinib, or GDC-0879, respectively. Whether or not a particular structural analog of a compound binds to a target in a substantially similar manner as does the compound can be determined in a variety of ways. For example, in many 2- or 3-dimensional kinase structures are available (e.g., determined using X-ray crystallography, NMR, or other approaches known in the art or by computational methods based on sequence similarity to kinases for which a structure has been determined experimentally), optionally complexed with a compound. Molecular modeling can be used to assess whether a structural analog of a compound is likely to bind to a kinase in a substantially similar manner to the manner in which the compound binds. For example, such approaches can be used to determine whether the analog will fit into a binding pocket into which the compound fits and or whether the analog will likely form hydrogen bonds or other interactions with the same amino acids as those to which the compound forms hydrogen bonds or other interactions. Computer programs for performing modeling and, optionally, visualization of compound-protein interactions (e.g., docking) are widely available. Examples include, e.g., Dock (and variants thereof such as AutoDock), PyMol, and the like. Experimental approaches can be used to assess whether a structural analog of a compound that inhibits a kinase will also inhibit the kinase. For example, the analog can be tested using a kinase inhibition assay in which the compound itself has been previously determined to show inhibitory activity. In some embodiments, a structural analog will have been designed and/or synthesized based on the same hit or lead compound as GNF-2, PLX4032, PLX4720, crizotinib, or GDC-0879, respectively.

In some embodiments, the compound is crizotinib, and the newly identified target is NTRK3 (e.g., ETV6-NTRK3) or RIPK1.

In some embodiments the compound is PLX4020, and the newly identified target is RIPK1.

VI. Methods of Inhibiting Biological Processes and Methods of Treatment

In some aspects of the invention, identification and/or characterization of small molecules that interact with protein kinases provides approaches to modulate one or more biological processes in which protein kinases play a role. In some aspects, the invention provides methods of modulating a biological process in which a kinase plays a role by contacting cells that express the kinase with a small molecule newly identified herein as an inhibitor of the kinase. In some embodiments, the process occurs in cell culture. In some embodiments, the process occurs in a subject.

In some embodiments, the kinase is RIPK1 and the biological process is necroptosis. In some embodiments, necroptosis is inhibited using crizotinib or PLX4032 or a structural analog of crizotinib or PLX4032.

In some aspects of the invention, identification and/or characterization of small molecules that interact with protein kinases provides approaches to treat a variety of diseases in which protein kinases play a role. In some aspects, the invention provides methods of treating a disease using a small molecule identified herein as an inhibitor of a kinase that plays a role in development and/or progression of the disease. In some embodiments, the method comprises administering the small molecule to a subject in need of treatment for the disease.

In some aspects, the invention provides candidate compounds for treatment of disorders associated with aberrant expression of NTRK3, e.g., disorders in which a fusion protein comprising at least part of NTRK3 is expressed, e.g., an ETVR6-NTRK3 fusion protein. In some embodiments, the candidate compound is crizotinib or a structural analog thereof. In some embodiments, a pharmaceutical composition for treating a disorder characterized by aberrant expression, e.g., overexpression, of NTRK3 is provided, the pharmaceutical composition comprising crizotinib or a structural analog thereof is provided. In some embodiments, a pharmaceutical composition for treating a disorder characterized by an ETVR6-NTRK3 fusion protein is provided, the pharmaceutical composition comprising crizotinib or a structural analog thereof is provided.

In some aspects, the invention provides a method of treating a disorder associated with aberrant expression of NTRK3, the method comprising administering crizotinib or a structural analog thereof to a subject in need of treatment for the disorder. In some embodiments, the disorder is a cancer. In some embodiments, the disorder is secretory breast carcinoma, mesoblastic nephroma, congenital fibrosarcoma, or acute myeloid leukemia. In some embodiments aberrant expression of NTRK3 occurs as a result of a t(12;15) translocation.

In some embodiments, the invention provides a method of treating a disorder associated with aberrant expression of RIPK1, the method comprising administering crizotinib or PLX4032 or a structural analog of crizotinib or PLX4032 to a subject in need of treatment for the disorder. In some embodiments, the disorder is one in which excessive or deleterious necroptosis occurs. In some embodiments, the disorder involves necroptosis associated with ischemia, injury (e.g., ischemia-reperfusion injury), or neurodegeneration.

In some embodiments a method of treating a disorder comprises providing a subject in need of treatment for the disorder. In some embodiments a method of treating a disorder comprises determining that a subject is in need of treatment for the disorder. In some embodiments a method comprises determining that the subject or a sample obtained from the subject exhibits aberrant expression or activity of a protein, e.g., a kinase. In some embodiments aberrant expression is overexpression. In some embodiments a method comprises determining that the subject or a sample obtained from the subject exhibits a translocation, mutation, or polymorphism associated with aberrant expression or activity of a protein, e.g., a kinase. In some embodiments a kit comprising one or more reagents suitable for diagnosing a disorder is provided. In some embodiments the kit is provided together with a pharmaceutical composition suitable for treating the disorder. The kit may comprise, e.g., an antibody (or other binding agent), probe, primer, or other reagent suitable for detecting a protein or nucleic acid associated with the disorder. In some embodiments the kit is a "companion diagnostic". In some embodiments a method of selecting a subject for treatment with a compound comprises determining that the subject suffers from a disorder associated with aberrant expression or activity of a protein that is a target of the compound. For example, in some embodiments a method of selecting a subject for treatment with crizotinib or a structural analog thereof, comprises determining that the subject suffers from a disorder associated with aberrant expression or activity of NTRK3, e.g., that the subject has an ETVR6-NTRK3 fusion protein and/or a t(12;15) translocation. Analagous methods are provided for other compounds and targets thereof disclosed herein or identified as described herein.

Compounds disclosed herein and/or identified using a method and/or assay system described herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or by inhalation, e.g., as an aerosol. The particular mode selected will depend, of course, upon the particular compound selected, the particular condition being treated and the dosage required for therapeutic efficacy. An effective amount of a compound or composition can be an amount that results in alleviation of symptoms, reduces the rate or likelihood of progression, stabilizes disease, results in an objective response, increase survival, etc. The methods of this invention, generally speaking, may be practiced using any mode of administration that is medically or veterinarily acceptable, meaning any mode that produces acceptable levels of efficacy without causing clinically unacceptable (e.g., medically or veterinarily unacceptable) adverse effects. Suitable preparations, e.g., substantially pure preparations, of one or more compound(s) may be combined with one or more pharmaceutically acceptable carriers or excipients, etc., to produce an appropriate pharmaceutical composition suitable for administration to a subject. Such pharmaceutically acceptable compositions are an aspect of the invention. The term "pharmaceutically acceptable carrier or excipient" refers to a carrier (which term encompasses carriers, media, diluents, solvents, vehicles, etc.) or excipient which does not significantly interfere with the biological activity or effectiveness of the active ingredient(s) of a composition and which is not excessively toxic to the host at the concentrations at which it is used or administered. Other pharmaceutically acceptable ingredients can be present in the composition as well. Suitable substances and their use for the formulation of pharmaceutically active compounds are well-known in the art (see, for example, "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable substances and methods of preparing pharmaceutical compositions of various types). Furthermore, compounds and compositions of the invention may be used in combination with any compound or composition or therapeutic modality (e.g., radiation, surgery) used in the art for treatment of a particular disease or condition of interest. For example, kinase inhibitors may be used to treat cancer in combination with any chemotherapy agent or combination thereof known in the art as being useful for treatment of cancer and/or with radiation and/or surgery. Examples of cancer chemotherapeutics that can be useful in some embodiments, include alkylating and alkylating-like agents such as Nitrogen mustards (e.g., Chlorambucil, Chlormethine, Cyclophosphamide, Ifosfamide, and Melphalan), Nitrosoureas (e.g., Carmustine, Fotemustine, Lomustine, and Streptozocin), Platinum agents (i.e., alkylating-like agents) (e.g., Carboplatin, Cisplatin, Oxaliplatin, BBR3464, and Satraplatin), Busulfan, Dacarbazine, Procarbazine, Temozolomide, ThioTEPA, Treosulfan, and Uramustine; Antimetabolites such as Folic acids (e.g., Aminopterin, Methotrexate, Pemetrexed, and Raltitrexed); Purines such as Cladribine, Clofarabine, Fludarabine, Mercaptopurine, Pentostatin, and Thioguanine; Pyrimidines such as Capecitabine, Cytarabine, Fluorouracil, Floxuridine, and Gemcitabine; Spindle poisons/mitotic inhibitors such as Taxanes (e.g., Docetaxel, Paclitaxel) and Vincas (e.g., Vinblastine, Vincristine, Vindesine, and Vinorelbine); Cytotoxic/antitumor antibiotics such anthracyclines (e.g., Daunorubicin, Doxorubicin, Epirubicin, Idarubicin, Mitoxantrone, Pixantrone, and Valrubicin), compounds naturally produced by various species of Streptomyces (e.g., Actinomycin, Bleomycin, Mitomycin, Plicamycin) and Hydroxyurea; Topoisomerase inhibitors such as Camptotheca (e.g., Camptothecin, Topotecan and Irinotecan) and Podophyllums (e.g., Etoposide, Teniposide); monoclonal antibodies such as anti-receptor tyrosine kinases (e.g., Cetuximab, Panitumumab, Trastuzumab), anti-CD20 (e.g., Rituximab and Tositumomab), and others for example Alemtuzumab, Gemtuzumab.

EXAMPLES

Materials

Plates and Reagents
Lumitrac 600 white high-binding 384-well microplates (Greiner Bio-One, 781074, order from VWR, 82051-268)
Costar 96-well flat bottom tissue culture plates (Fisher, 07-200-92)
BioLux™ Gaussia Luciferase Flex Assay Kit (New England Biolabs, E3308L) or Renilla luciferase kit (Promega)
Mouse anti-FLAG M2 (Sigma, F1804)
DDDDK tag antibody (goat), HRP-conjugated (Abcam, ab1238) or
V5-tag antibody (rabbit), HRP-conjugated (GenScript #A00877)
1-step Turbo-TMB, 250 ml (Pierce, 34022)
Lipofectamine 2000 (Invitrogen, 11668-019) or
Polyethylenimine (Sigma 408727)
OptiMEM serum reduced media (Invitrogen, 22600-134)
Kinase inhibitors were obtained from various commercial suppliers.
Solutions
Blocking Buffer
3% BSA
5% sucrose
0.5% Tween 20
1×PBS
Lysis & IP Buffer
50 mM Hepes-KOH pH 7.9
150 mM NaCl
2 mM EDTA pH 8.0
20 mM sodium molybdate (for Hsp90 interaction assays)
0.5% Triton X-100
5% glycerol
Complete protease inhibitor cocktail (Roche) or aprotinin, leupeptin, pepstatin (1 µg/ml each) and PMSF (0.11 mM). Add 1 mM sodium vanadate and 1 mM sodium fluoride if inhibition of phosphatases is desired. (The phosphatase inhibitors were included in the lysis & IP buffer used in Examples described here.)
ELISA Buffer
5% Tween 20
1% goat serum
1×PBS Construction of Bait and Prey Constructs Human HSP90β (HSP90AB1) was tagged with Renilla or Gaussia luciferase either at the N-terminus or in the C-terminal domain. The cDNAs encoding Renilla or Gaussia luciferase that were used to generate the constructs encoding the fusion proteins had been codon optimized for expression in human cells. The accession number for codon-optimized Gaussia luciferase is FJ010198 and for Renilla luciferase is AY738231. The sequence encoding the Gaussia luciferase signal sequence (first 17 amino acids: MGVKVLFALICIA-VAEA (SEQ ID NO: 1)) was removed.

In one construct, Renilla luciferase was inserted after codon Ala696, such that the preceding sequence DEDEVA (SEQ ID NO: 5) was duplicated after the Renilla luciferase insert as follows:
LGLGIDEDEVA(TS)ASKVYDD (SEQ ID NO: 6) . . . Renilla luciferase . . . VLKNEQ(TG)DEDEVAAEE (SEQ ID NO: 8).

Sequences (TS) and (TG) in parenthesis are from inserted SpeI and AgeI restriction sites, respectively. The starting and ending sequences of *Renilla* luciferase sequence are underlined. Human HSP90α (HSP90AA1) can be tagged in the identical position after Thr704 and duplicating the sequence DEDDPT (SEQ ID NO: 2). Alternatively, HSP90 isoforms were tagged at the N-terminus with luciferase separated by a flexible linker sequence SGGRSSGSGSTSGSG (SEQ ID NO: 3).

CDC37 was tagged in an analogous manner either at the N-terminus or C-terminus. In the latter case the flexible linker sequence was DIQHSGGRSSGSGSTSGSGKTG (SEQ ID NO: 4) followed by *Renilla* luciferase.

Other co-chaperones tested were tagged at the N- and/or C-terminus in a similar manner.

Cell Lines

Stable 293T cell lines expressing *Renilla* or *Gaussia* luciferase-tagged fusion proteins were constructed by lentiviral infection using Invitrogen's pLenti6 vector system, in which the blasticidin resistance gene had been replaced with a puromycin resistance gene. Infected cells were selected with puromycin and polyclonal cell lines established from puromycin-resistant cells.

Protein Kinase Constructs

All protein kinases from the human ORFeome (Lamesch et al., Genomics. 89(3):307-15, 2007.) and Broad Institute/CCSB kinome collection (Johannessen C M, Nature. 468 (7326):968-72, 2010) were cloned into pcDNA3.1-based vector that carried a C-terminal 3×FLAG and V5 tags using LR clonase. All inserts were verified with restriction digestion and those clones that did not produce expected digestion pattern were either confirmed as correct by sequencing or discarded.

Coating and Blocking of the Plates 384 well plates were coated and blocked using the following protocol:
1) Prepare 10 μg/ml anti-FLAG M2 solution in 1×PBS. This corresponds to 1:100 dilution from the original anti-FLAG bottle.
2) Add 20 μl/well antibody solution to 384-well plates. Use small cassette to minimize the loss of antibody due to void volume.
3) Cover plates with aluminum foil and incubate overnight on a shaking platform.
4) Aspirate all buffer and flick off any remaining liquid.
5) Add 95 μl blocking buffer per well with plate filler using the regular cassette
6) Incubate plates with blocking buffer for at least 1 hour at room temperature. Plates do not need to be covered at this point.
7) Aspirate all blocking buffer and flick off any remaining liquid
8) Use immediately, or alternatively cover plate with sealing tape or stacks of plates with Parafilm and store at 4° C. (plates can be stored for at least a month in the fridge)

Transfections 293T cell lines stably expressing a human chaperone protein (HSP90β, CDC37, or another co-chaperone) tagged with *Renilla* or *Gaussia* luciferase were established with lentiviral infection as described above. 200 ng of each kinase construct was transfected into cells using Lipofectamine 2000 (Invitrogen) according to the following protocol based on the manufacturer's guidelines:
1) Seed 293T cells into round-bottom 96-well plates such that they are ~95% confluent on the day of transfection. Antibiotic-free medium may be used but is not required and was not used in these Examples.
2) Add 200 ng DNA to each well of 96-well plate. Add 25 μl OptiMEM to each well with DNA.
3) Prepare master mix by adding 66 μl Lipofectamine to 2750 μl OptiMEM (this amount of master mix is sufficient for 110 wells), and incubate the mix for 5 minutes.
4) Add 25 μl master mix to each well with DNA+OptiMEM, swirl to mix, and incubate for 25 minutes. Note: Add transfection mix to wells carefully to avoid losing cells
5) Replace the medium the next day (optional, usually not performed in these Examples)
6) Two days after transfection, proceed to LUMIER assay
Note 1: A more economical way to transfect 293T cells is to use polyethylenimine (Sigma 408727) instead of Lipofectamine 2000. PEI was diluted to 1 mg/ml in water and adjusted to pH 7.4 with HCl. This solution was used as an alternative to Lipofectamine 2000 in some transfection assays. PEI worked well but was more toxic to 293T cells and required more DNA for efficient transfection. In a small-scale optimization experiment, the best transfection efficiency was with 400 ng DNA and 0.8 μl PEI (1 mg/ml).
Note 2: In experiments in which cells are transiently transfected both with prey and bait constructs, 100 ng each would be used.

Enhanced LUMIER assay
1) Wash cells twice with 1×PBS (100 μl/well)
2) Lyse cells with ice-cold lysis & IP buffer (80 μl/well).
3) Transfer 60 μl to anti-FLAG coated 384-well plates, keep the rest at 4° C.
4) Incubate plates for 3 hours at 4° C. on a rocking or shaking platform. Do not cover plates with a sealing film, since it appears to increase well-to-well contamination 5) Prepare luciferase reagent according to manufacturer's instructions just before washes. Reagents for one 384 plate (assuming *Gaussia* luciferase is used):
2 ml GLuc Flex Assay Buffer
6 ml 1×PBS
250 μl Glue Flex Stabilizer
20 μl Glue Flex Substrate
6) Wash plate six times with lysis & IP buffer (100 μl/well) using an automated plate washer
7) After the last wash, flick off any remaining liquid and add 20 μl luciferase assay buffer prepared earlier (small cassette)
8) Measure luminescence with the Envision plate reader. 100 msec measurement time works well.
9) Only for co-transfections: to control for prey input, measure luminescence of 10% input (6 μl cell lysate)
10) After reading luminescence, flick off the reagent
11) Add ELISA detection antibody (1:10,000 dilution of goat anti-DDDDK (SEQ ID NO: 7) tag or rabbit an tag) in ELISA buffer (30 μl).
12) incubate plates (no cover) for 1 h 30 min at room temperature on a rocking platform.
13) Wash the plate six times with 1×PBS/0.05% Tween. Flick off remaining liquid and remove the adhesive seal from the bottom of the plate
14) Add 30 μl 1-Step Turbo-TMB and let the reaction develop for 5 minutes.
15) Stop reaction with 30 μl 2M $H_2SO_4$
16) Transfer 50 μl solution from each well to a transparent 384-well plate
17) Read absorbance at 450 nm with a standard plate reader.

Inhibitor Treatment

Human kinase constructs described above were in 96-well plates. In typical chaperone-kinase interaction assays, for each 96-well plate containing kinase clones, four identical 96-well plates containing 293T cells were transfected (as described above) with cDNAs encoding the kinases to be tested. Two days after transfection, kinase inhibitor (typically 5 µM final concentration) was added to two plates, while the two control plates were treated with vehicle only (typically growth medium). Plates were incubated for 1 hour at 37 degrees in the tissue culture incubator. Cells were washed with 1×PBS and lysed with lysis buffer described above. All four 96-well plates were consolidated into one 384-well plate, such that for each kinase the control and drug-treated samples were located in adjacent wells. Results for the 4 wells corresponding to the same kinase clone were averaged.

To normalize between different plates, standard curves can be created with dilution series of 3×FLAG-tagged and *Renilla* or *Gaussia* luciferase constructs, and luminescence and ELISA readings between plates compared. It was observed that luminescence readings get unreliable in high concentrations of *Renilla* or *Gaussia*, possibly due to aggregation, so care should be taken to avoid artifacts due to this phenomenon.

Interaction Score

Interaction scores were calculated as base 2 logarithm of the ratio between *Renilla* or *Gaussia* luminescence (amount of prey protein, e.g., HSP90 or CDC37 or other co-chaperone) and ELISA $OD_{450}$ (amount of kinase bait). Fold change in interaction ($score_{drug}$-$score_{control}$) was calculated for each kinase, together with the p-value for the change. Kinases that showed a statistically significant ($p<0.05$) decrease in interaction with HSP90 or CDC37 upon kinase inhibitor treatment were classified as hits (targets) for the inhibitor.

In some experiments, each plate had eight wells with a two-fold dilution series of 3×FLAG-tagged *Gaussia* luciferase that was used for normalization and as a standard for ELISA signal. Briefly, linear standard curve was fitted to *Gaussia* luminescence vs ELISA OD450, and 3×FLAG-tagged protein abundance in each well was calculated from this curve. Interaction score was calculated as log 2 (observed luminescence*10000/expected luminescence). Non-specific binding of *Renilla*-tagged prey to the well could potentially cause background luminescence. To assess the potential effect of such non-specific binding, we performed the same interaction assay with a cell line that expressed *Renilla* luciferase only. There was no significant correlation between replicates, demonstrating that *Renilla* luciferase binding to the kinases was non-specific. Thus, we did not subtract *Renilla* luciferase binding from Hsp90-*Renilla* binding separately for each bait. Furthermore, the amount of *Renilla* luminescence in the well did not correlate with bait abundance (i.e. ELISA signal), showing that overexpression-induced artifacts were not a significant confounding factor in the analysis.

Background luminescence values in *Renilla* only control cell lines followed Gaussian distribution after log normalization. Thus, we used absolute luminescence as the first cutoff in determining whether or not a kinase bait interacted with HSP90β. To determine the cutoff point, we used a method similar to that reported in Newman et al., Nature 441: 840-846, 2006. Briefly, luminescence values (log 10) from each replicate were binned, and the bin containing the maximum number of baits ($F_{max}$) was identified. Subsequently, the luminescence values to the left of the bin (i.e. lower luminescence) were reflected about $F_{max}$ to produce a symmetric distribution. This distribution was fitted to a Gaussian curve. $F_{max}$ (i.e. mean of the fitted Gaussian curve) thus represents background luminescence. Protein was classified as a true interactor if luminescence was greater than µ+1σ in both replicates. False discovery rate for each replicate was 15.87%, but since background luminescence is random and normally distributed, the final FDR is the product of the two, i.e. 2.5%. Interaction score was calculated only for those baits that exceeded the threshold.

Example 1: Development of a Quantitative Assay for Protein-Protein Interactions

We were interested in investigating the determinants involved in binding of the chaperone HSP90 to its kinase clients. To facilitate our studies we wished to quantitatively measure interaction between HSP90 and multiple different kinases in a high-throughput format. To this end, we explored the use of the LUMIER (LUminescence-based Mammalian IntERactome mapping) assay (Barrios-Rodiles et al., Science, 307: 1621-5, 2005). In the original LUMIER assay described by Barrios-Rodiles et al., one protein (prey) is tagged with *Renilla* luciferase and the other protein (bait) with the FLAG epitope. After transfection of constructs encoding the prey and bait proteins to mammalian cells, lysates are used for immunoprecipitation (IP) with anti-FLAG-coated magnetic beads. Co-immunoprecipitation of prey and bait proteins is assayed by measuring *Renilla* luciferase activity after IP.

We substantially modified the LUMIER assay in order to make it more quantitative and robust. A schematic diagram of an implementation of our assay is shown in FIG. 1. Additional details are provided above. As shown in FIG. 1, luciferase-tagged prey construct is expressed in a stable cell line. We empirically found that stable expression of the prey protein greatly decreases well-to-well variability as compared with transient transfection. Another significant modification was the use of anti-FLAG coated microplates instead of magnetic beads, which both simplifies the procedure and avoids the requirement for special equipment for bead separation. In addition, we perform an anti-FLAG ELISA in order to quantitate the amount of FLAG-tagged protein in the well. Thus, we can measure the amount of prey protein (by measuring luciferase activity) and bait protein (using anti-FLAG ELISA) in the same well, which gives us a robust and quantitative interaction score for protein-protein interactions, allowing us to detect subtle differences in the level of protein-protein interactions. The assay is sufficiently robust and quantitative to permit detection and measurement of alterations in protein-protein interactions resulting from binding of small molecules to proteins (e.g., chaperones and their clients) that participate in protein-protein interactions.

Example 2: Profiling Interaction of HSP90β with Human Kinases

We generated stable 293T cell lines encoding human HSP90β tagged with either *Renilla* or *Gaussia* luciferase. Cells were transfected in individual wells of 96-well plates with members of a panel of constructs encoding ~370 wild type human kinases tagged with 3×FLAG and V5 tags. The enhanced LUMIER assay described above was used to measure the interaction of HSP90β with the ~370 human kinases. Analysis of the results revealed that the majority of kinases tested are HSP90β client proteins (FIG. 2) and identified numerous kinases not hitherto known to interact with HSP90β. We developed a metric that we termed an "interaction score" to quantitatively express the level of HSP90-kinase interaction and classified kinases as strong, intermediate/weak, or non-interacting based on the interaction scores (weak kinase clients scored between 0-3 and strong clients were >3).

Figure 4:
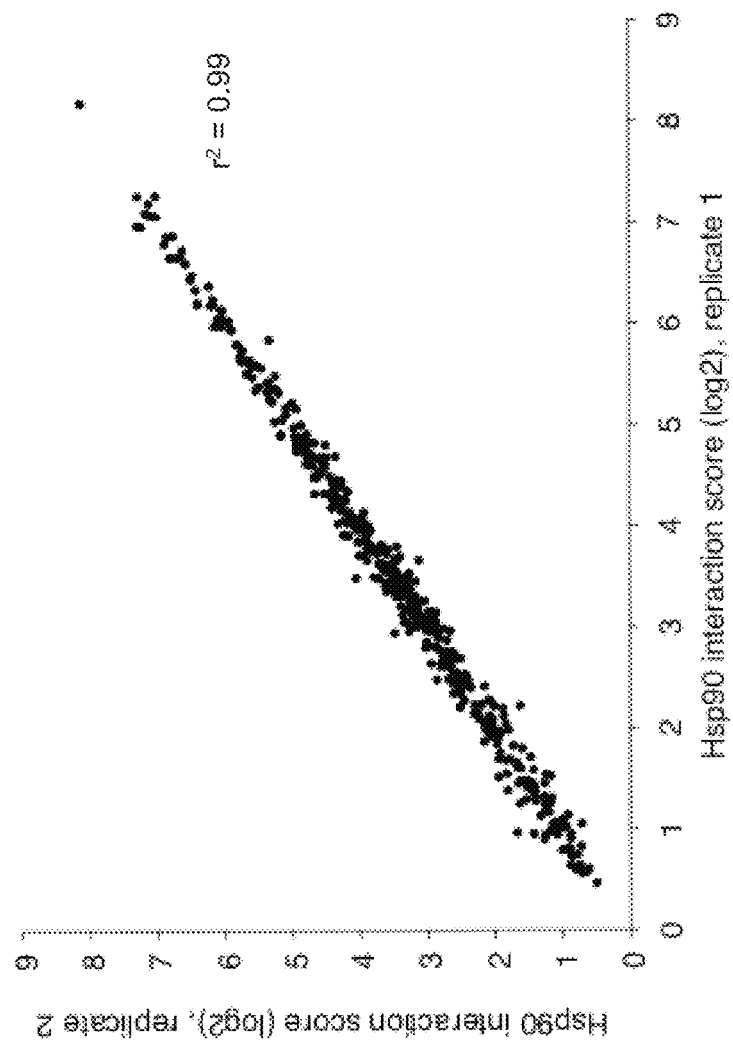
FIG. 4 is a plot in which Hsp90β interaction scores for members of a panel of human kinases as measured in two separate experiments are plotted against one another. The plot illustrates the extremely high degree of correlation between replicates.

FIG. 4 is a plot in which Hsp90β interaction scores for members of a panel of human kinases as measured in two separate experiments are plotted against one another. The plot illustrates the extremely high degree of correlation ($r^2=0.99$) between replicates. This was considerably greater than the correlation between replicates when luminescence only was measured ($r^2<0.90$).

In addition to wild type kinases, we tested numerous kinase mutants as well as kinase fusion proteins arising from chromosomal translocations (a number of which are associated with a variety of different human cancers) for interaction with Hsp90β. Many of the kinase mutants tested are oncogenic and, in some cases, a mutation renders the kinase resistant to inhibition by at least some compounds that would otherwise inhibit the kinase. We found that Hsp90β interacts with kinase mutants and kinase fusion proteins. In some instances interaction of Hsp90β with mutant kinases was observed even in cases in which Hsp90β did not detectably interact with the corresponding wild type kinase.

Table 1 presents list of the human kinases (wild type kinases, mutant kinases, kinase fusion proteins) that we showed interact significantly with HSP90β. Based on these results, we expect that additional kinases that remain to be tested also interact with HSP90β.

CDC37 is an HSP90β co-chaperone that exhibits specificity for kinase clients of HSP90β. We generated constructs encoding luciferase-tagged CDC37 and used CDC37 as prey protein in our assay to examine interaction of CDC37 with kinase clients of HSP90β. Results showed that CDC37-kinase interactions can readily be detected and quantified as in the case of HSP90β-kinase interactions.

Figure 5:
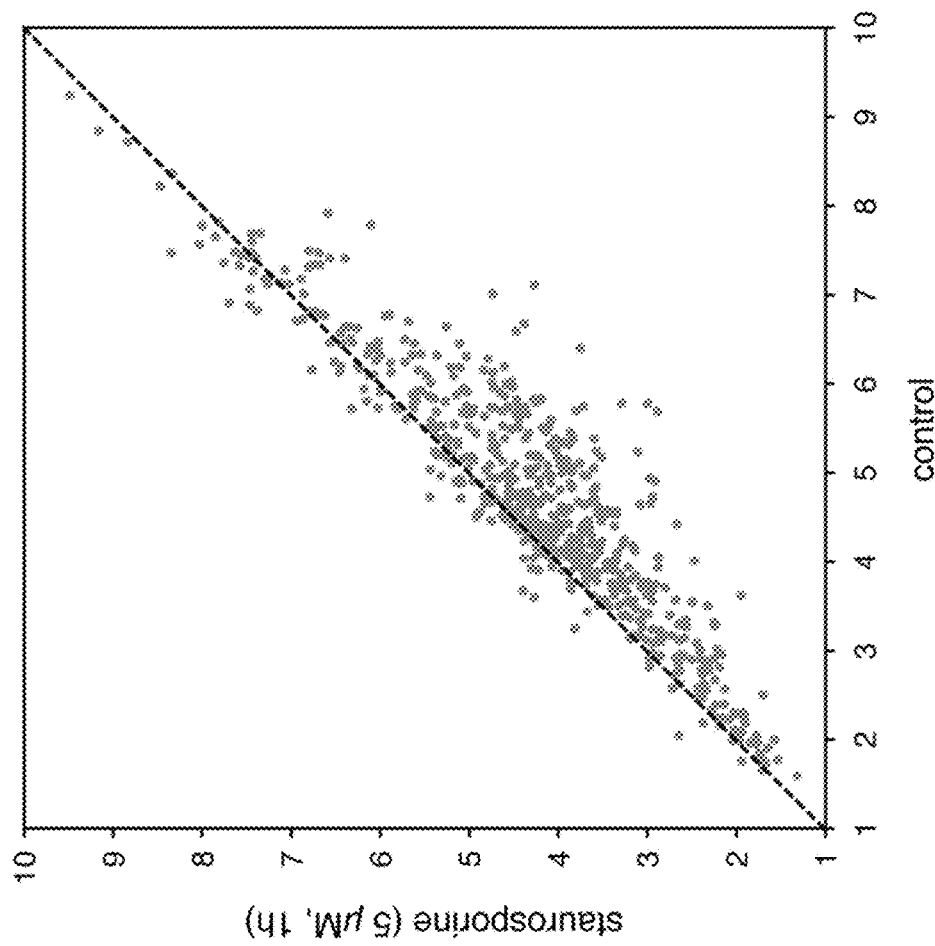
FIG. 5 is a plot of the interaction scores for members of a panel of human kinases in the absence (x-axis) or presence (y-axis) of staurosporine.

Example 3: Small Molecule Kinase Inhibitors Decrease Interaction Between Chaperones and Kinase Clients As discussed above, numerous small molecules have been developed that bind to various kinases and are known to inhibit their activity. We explored the effects of a variety of such inhibitors on the interaction between HSP90β and HSP90β client kinases that are known target(s) of the inhibitor by performing quantitative luminescence-based protein-protein interaction assays using luciferase-tagged HSP90β as a prey protein and different kinase clients as prey, in the presence or absence of small molecules known to inhibit the particular kinase being used as a prey protein. We observed that small molecule kinase inhibitors detectably decreased the interaction between HSP90β and HSP90β client kinases that are targets of such inhibitors. This effect is reproducible and has been confirmed using multiple different protein kinases and small molecules known to inhibit those kinases. For example, FIG. 5 is a plot of the interaction scores for members of a panel of human kinases in the absence (x-axis) or presence (y-axis) of staurosporine, an ATP-competitive kinase inhibitor that is well known to bind to many kinases with high affinity but little selectivity. The diagonal line represents the situation in which the presence of the compound does not affect the interaction. As can readily be seen, staurosporine reduces a substantial proportion of HSP90β/kinase interactions.

We recognized that detecting (e.g., measuring) the reduction in HSP90β-kinase interaction that results from the presence of small molecule kinase inhibitors that bind to the kinase could be used for a variety of purposes. For example assays that measure HSP90β-kinase interaction in the presence and absence of small molecule kinase inhibitor(s) can be used as a means to characterize such compound(s) and/or as a means to characterize kinases with respect to their sensitivity to small molecule kinase inhibitors.

We extended our results to include use of luciferase-tagged CDC37 as a prey protein for profiling kinases and small molecules. In general, CDC37 performed at least as well as HSP90β in these assays. Thus, assays based at least in part on detecting a CDC37-kinase interaction can be used, for example, to characterize small molecules with regard to their ability to bind to kinases and/or to characterize kinases with regard to their susceptibility to inhibition by small molecules.

Example 4: Profiling the Effect of Imatinib on HSP90β-Kinase Interactions Identifies Known Targets of Imatinib and Reveals New Imatinib Targets We used our quantitative luminescence-based protein-protein interaction assays to profile the effects of imatinib (Gleevec) on kinase/HSP90β interactions. As expected, the interaction of BCR-ABL, the primary previously known target of imatinib, with HSP90β is greatly reduced upon imatinib treatment (FIG. 6A). Furthermore, four other known Gleevec targets (ABL1, DDR1, PDGFRB, CSF1R) were recovered from the assay. However, interaction of the clinically highly relevant imatinib-resistant mutant of BCR-ABL (T315I) with HSP90β was not decreased by imatinib, consistent with the known inability of imatinib to inhibit this mutant kinase. These results further demonstrate the ability of the inventive assays to identify kinase targets of small molecules.

Profiling of imatinib also revealed a number of new targets of imatinib (indicated as dots that lie below the diagonal line), which remain to be individually verified in other assays.

Example 5: Effect of Various Kinase Inhibitors on HSP90β-Kinase Interactions Accurately Reflects Inhibitor Specificity We used QLPPI assays to analyze the effects of the HSP90 inhibitor 17-AAG and the following kinase inhibitors: (i) SU6656; (ii) an EGFR inhibitor; (iii) erlotinib; and (iv) the BCR-ABL inhibitor imatinib on the interaction of HSP90β with v-Src, BCR-ABL, imatinib-resistant BCR-ABL mutant BCR-ABL (T315I), erlotinib-sensitive EGFR mutant EGFR L858R, and erlotinib-resistant EGFR mutant EGFR L858R T790M. Erlotinib is an EGFR inhibitor used in the treatment of non-small cell lung cancer and pancreatic cancer.

Figure 7:
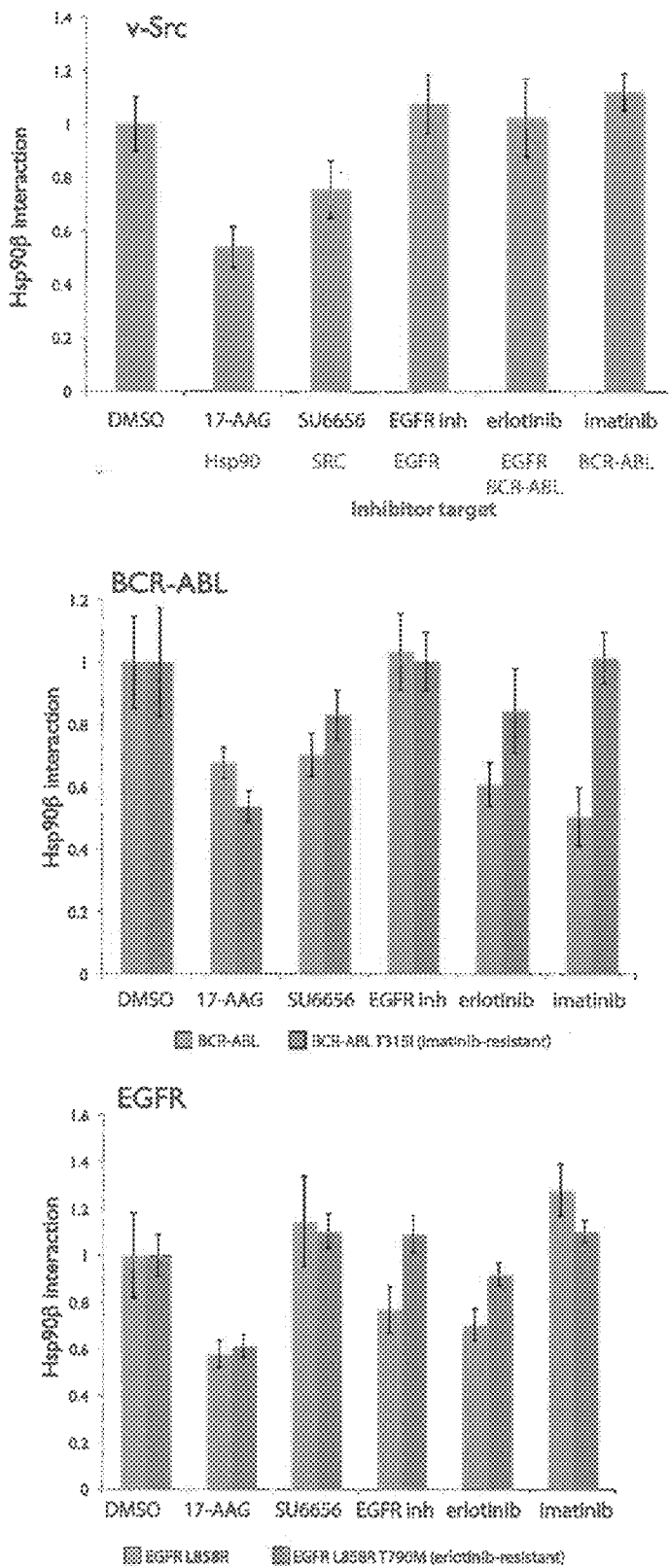
FIG. 7 contains plots showing the level of interaction between HSP90β and various kinases in the presence or absence of various inhibitors, as indicated. Upper panel: interaction between HSP90β and v-Src. Middle panel: interaction between Hsp90β and wild-type BCR-ABL (blue bars) or the imatinib-resistant BCR-ABL T315I mutant (red bars). Lower panel: interaction between HSP90β and EGFR L858R mutant (blue bars) or the erlotinib-resistant EGFR L858R T790M mutant (red bars). Known targets of the inhibitors are indicated below their names in the upper panel.

FIG. 7 contains plots showing the level of interaction between HSP90β and each kinase in the presence or absence of indicated inhibitors. Consistent with its activity as an HSP90 inhibitor, 17-AAG inhibits interaction of HSP90β with each of the tested kinases. Consistent with its original identification as an inhibitor or Src family kinases, SU6656 significantly inhibits interaction between Hsp90β and Src. SU6656 also inhibits interaction between Hsp90β and wild type or mutant BCR-ABL but does not significantly affect the interaction between Hsp90β and wild type or mutant EGFR. Erlotinib and imatinib significantly decrease interaction between HSP90β and wild type BCR-ABL. Erlotinib exhibits reduced ability to decrease interaction between Hsp90β and mutant BCR-ABL as compared with its ability to decrease interaction between Hsp90β and wild type BCR-ABL), while imatinib fails to decrease interaction between Hsp90β and mutant BCR-ABL. Erlotinib and the other EGFR inhibitor tested both decreased the interaction between HSP90β and the erlotinib-sensitive EGFR mutant but did not significantly affect the interaction of HSP90β with the erlotinib-resistant EGFR mutant.

We also quantitatively assessed the effect of kinase inhibitors dasatinib, imatinib, ponatinib, and GNF-2 on the interaction between BCR-ABL or the T351I BCR-ABL mutant and HSP90β over a range of inhibitor concentrations using a QLPPI assay. Dasatinib is a multi-BCR/ABL and Src family tyrosine kinase inhibitor (Das, J. et al. J. Med. Chem., 2006, 49 (23), pp 6819-6832, 2006). It is used to treat CML and is currently being evaluated in clinical trials for treatment of a variety of solid tumors. In addition to inhibiting BCR/ABL and Src family TKs, dasatinib has been shown to inhibit a variety of other TKs. Ponatinib was previously identified as a pan-BCR-ABL inhibitor that potently inhibits the T315I gatekeeper mutant, and has advanced into clinical development for the treatment of refractory or resistant CML (O'Hare, et al., Cancer Cell. 2009, 16(5): 401-112; Huang, T., et al., Bioorg Med Chem Lett. 2011, 21(12): 3743-8.). Ponatinib is active against a variety of other kinases, such as FLT3 (involved in leukemia) as well as being a pan-FGFR inhibitor, potentially useful to treat a variety of FGFR-driven cancers (Gozgit, J M, et al., Mol Cancer Ther. 2012; 11(3):690-9). GNF-2 has been characterized as a highly selective non-ATP competitive inhibitor of oncogenic BCR-ABL activity that binds to the myristoyl pocket located near the C-terminus of Abl kinase domain, and a number of structural analogs with this ability have been synthesized (Zhang, J, et al., Nature. 463(7280): 501-506, 2010; Deng, X., et al., J Med Chem. 14; 53(19):6934-46, 2010).

Figure 8:
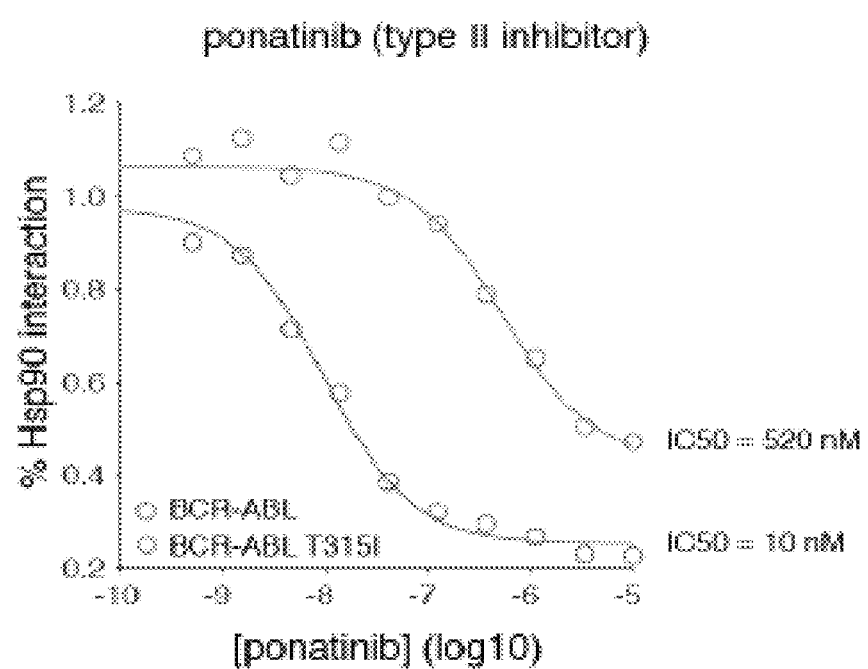
FIG. 8A shows quantitative assessment of the effect of kinase inhibitors dasatinib (a type I inhibitor; lower left panel), imatinib (a type II inhibitor; upper left panel), and GNF-2 (a type III inhibitor; upper right panel) on the interaction between BCR-ABL (orange) or the T351I BCR-ABL mutant (green) and HSP90β. IC50 values are indicated for those instances in which the inhibitor significantly inhibited the kinase. The lower right panel shows a ribbon diagram of BCR-ABL protein with imatinib and GNF-2 bound thereto.
FIG. 8(B) shows quantitative assessment of the effect of kinase inhibitor ponatinib (a type II inhibitor) on the interaction between BCR-ABL (blue) or the T351I BCR-ABL mutant (orange) and HSP90β.

Graphs showing the results are presented in FIG. 8. IC50 values are indicated for those instances in which the tested inhibitor significantly inhibited the kinase. The results correctly indicated that imatinib and dasatinib inhibit BRC-ABL but do not inhibit the resistant BCR-ABL T315I mutant, which is known to be resistant to multiple kinase inhibitors including imatinib and dasatinib. The assay with ponatinib correctly indicated that this compound inhibits BCR-ALB and the BCR-ABL T315I mutant (although the compound was less effective at inhibiting the T315I mutant. The results with ponatinib are consistent with the previously determined inhibitory activity of ponatinib. The assays with GNF-2 are consistent with another study that showed that GNF-2 still binds to the T315I mutant with a two-fold reduced affinity compared to wild-type (Zhang, 2010). These results demonstrate the ability of the inventive QLPPI and CCI assays to measure interaction of representative members of the three main categories of kinase inhibitor with representative kinase targets and to accurately distinguish between kinases that are sensitive and resistant to particular inhibitors.

Figure 9A:
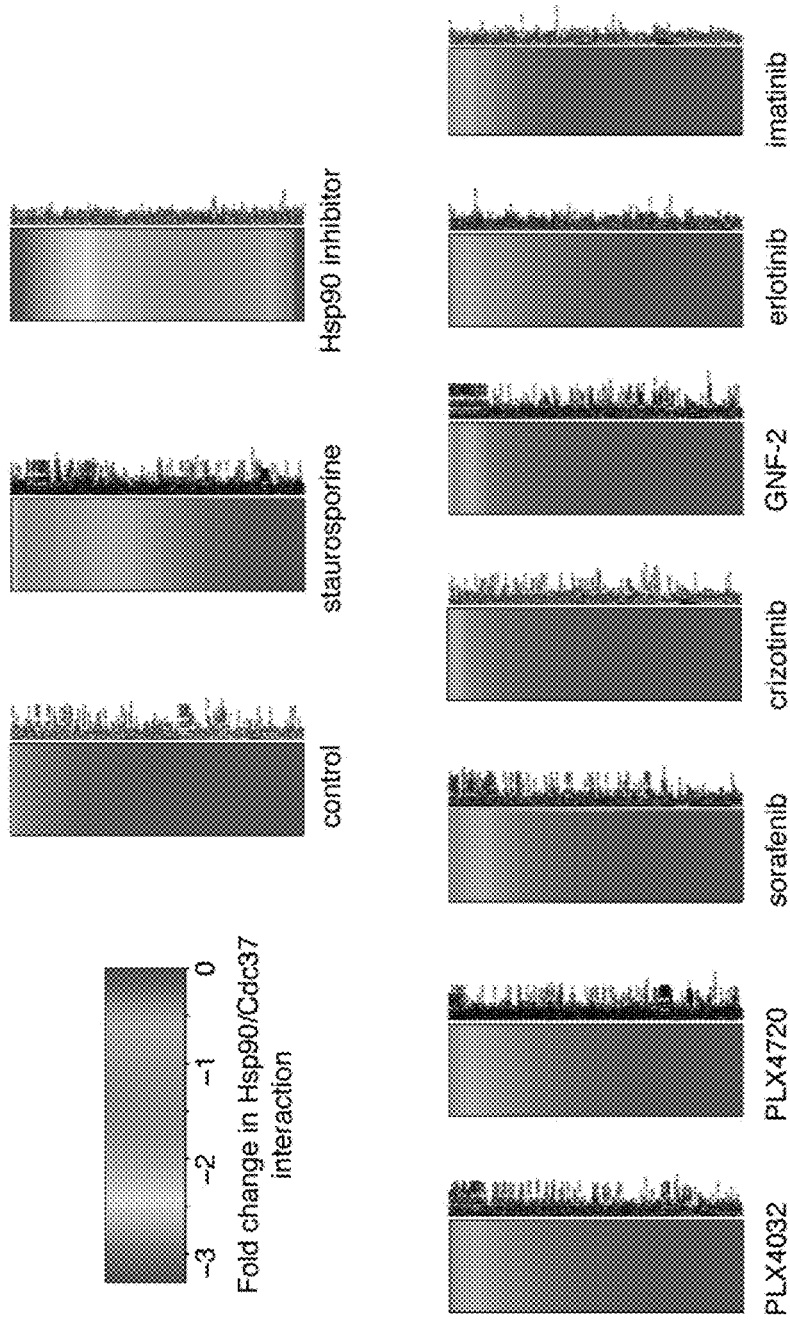
FIG. 9 shows heatmaps representing the fold change in interaction of HSP90β or CDC37 with individual members of a kinase panel in the presence of a variety of different kinase inhibitors, as compared with control level of interaction (control=vehicle only added to wells), as determined using a CII assay. (A) Heatmaps showing results of testing the following compounds with the kinase panel using either HSP90β or CDC37 as the prey protein, as indicated in parentheses: staurosporine (HSP90β); a small molecule HSP90A inhibitor; PLX4032 (HSP90β); PLX4720 (CDC37); sorafenib (CDC37); crizotinib (HSP90β); GNF-2 (CDC37); erlotinib (CDC37); imatinib (HSP90β). Control represents an assay in which compound was not added to either the "compound" or "no compound" wells. (B) Expanded view of the upper portion of heatmap for GNF-2. Results indicate that various imatinib-resistant mutants remain sensitive to GNF-2, consistent with GNF-2 binding to a different region of the kinase than does imatinib. BCR-ABL itself appears further down on the list of GNF-2 targets. (C) Expanded view of the upper portion of the heatmap for erlotinib EGFR appears further down the list of erlotinib targets; (D) Expanded view of the upper portion of the heatmap for sorafenib (Nexavar). (E) Expanded view of the upper portion of the heatmap for PLX4720. (F) Expanded view of the upper portion of the heatmap for crizotinib (left).
Figure 9B:
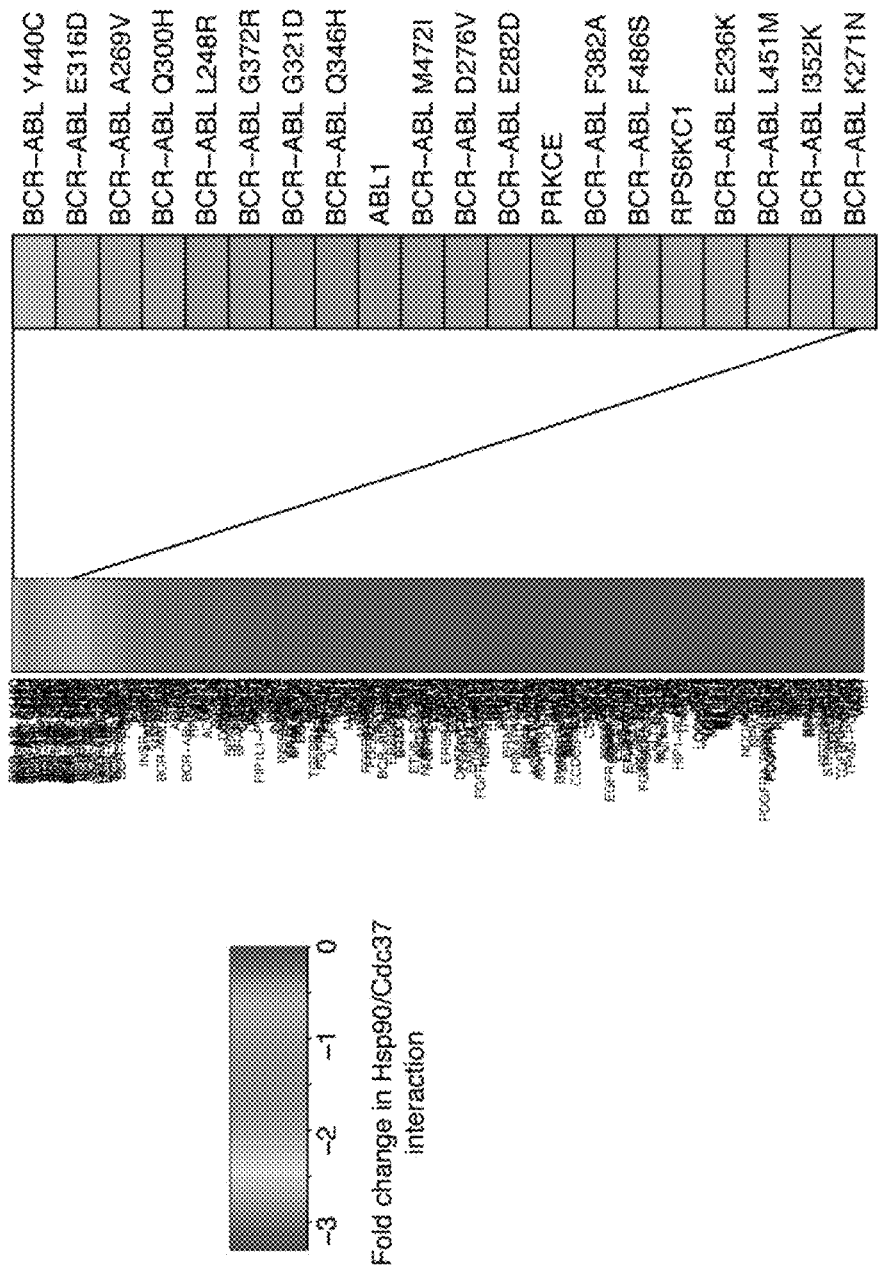
Figure 9C:
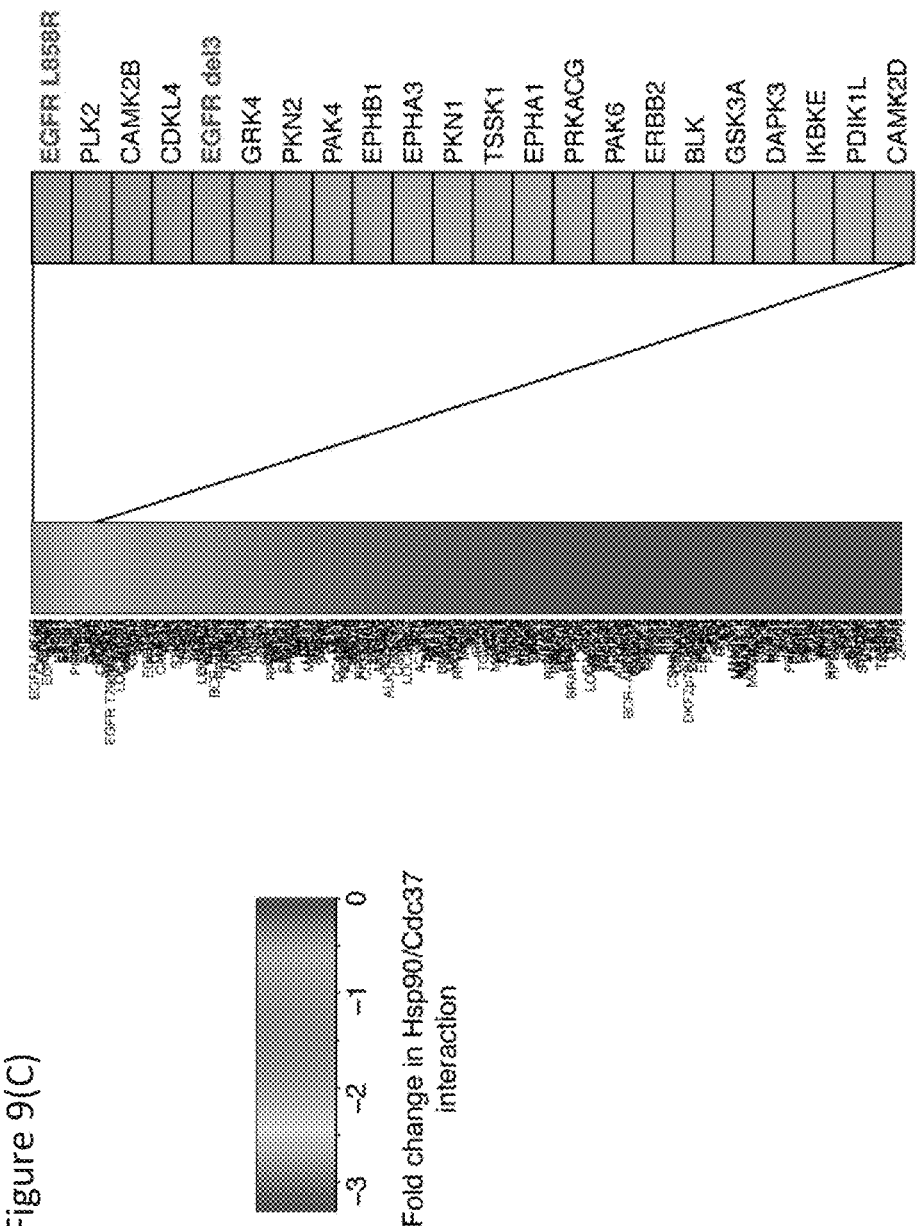
Figure 9D:
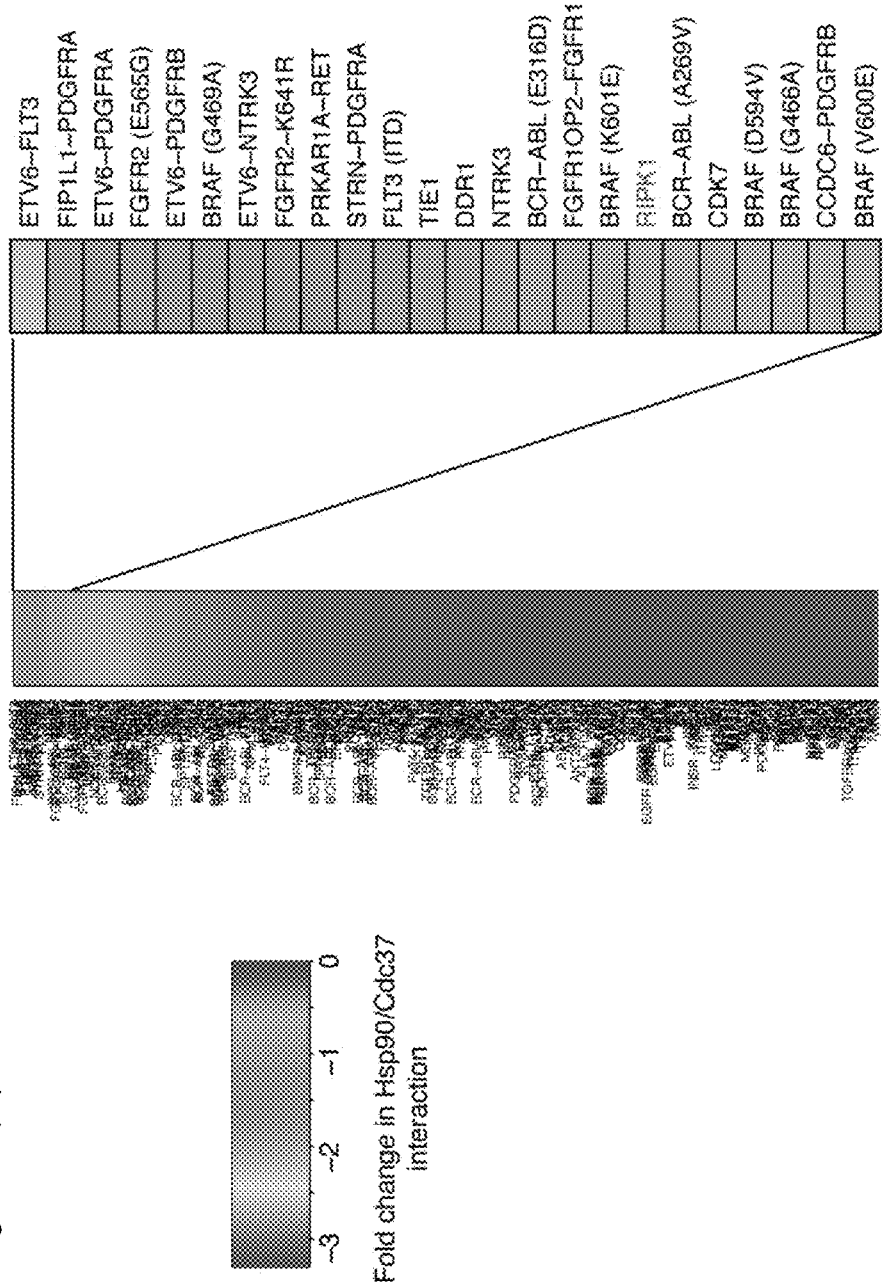
Figure 9E:
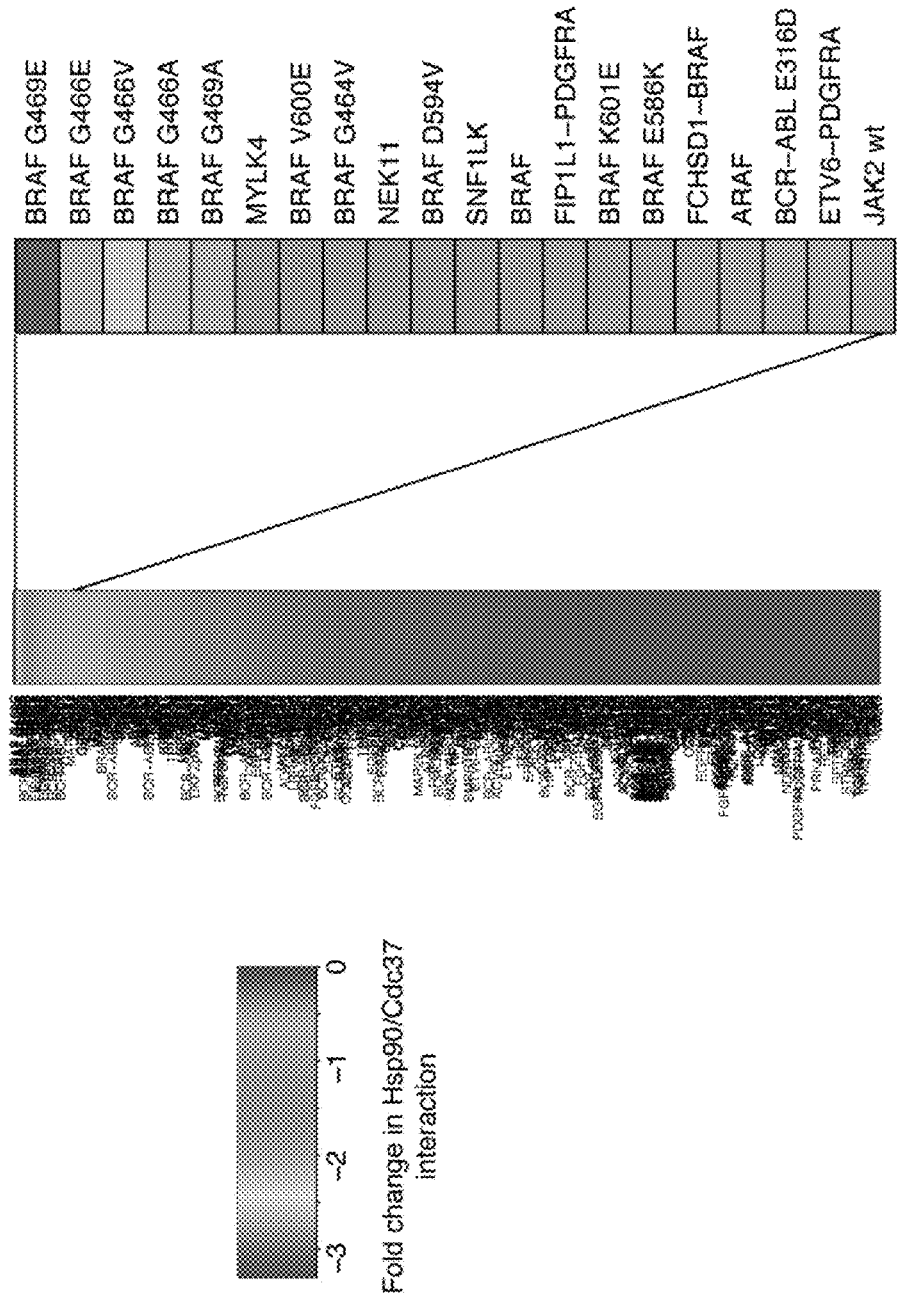
Figure 9F:
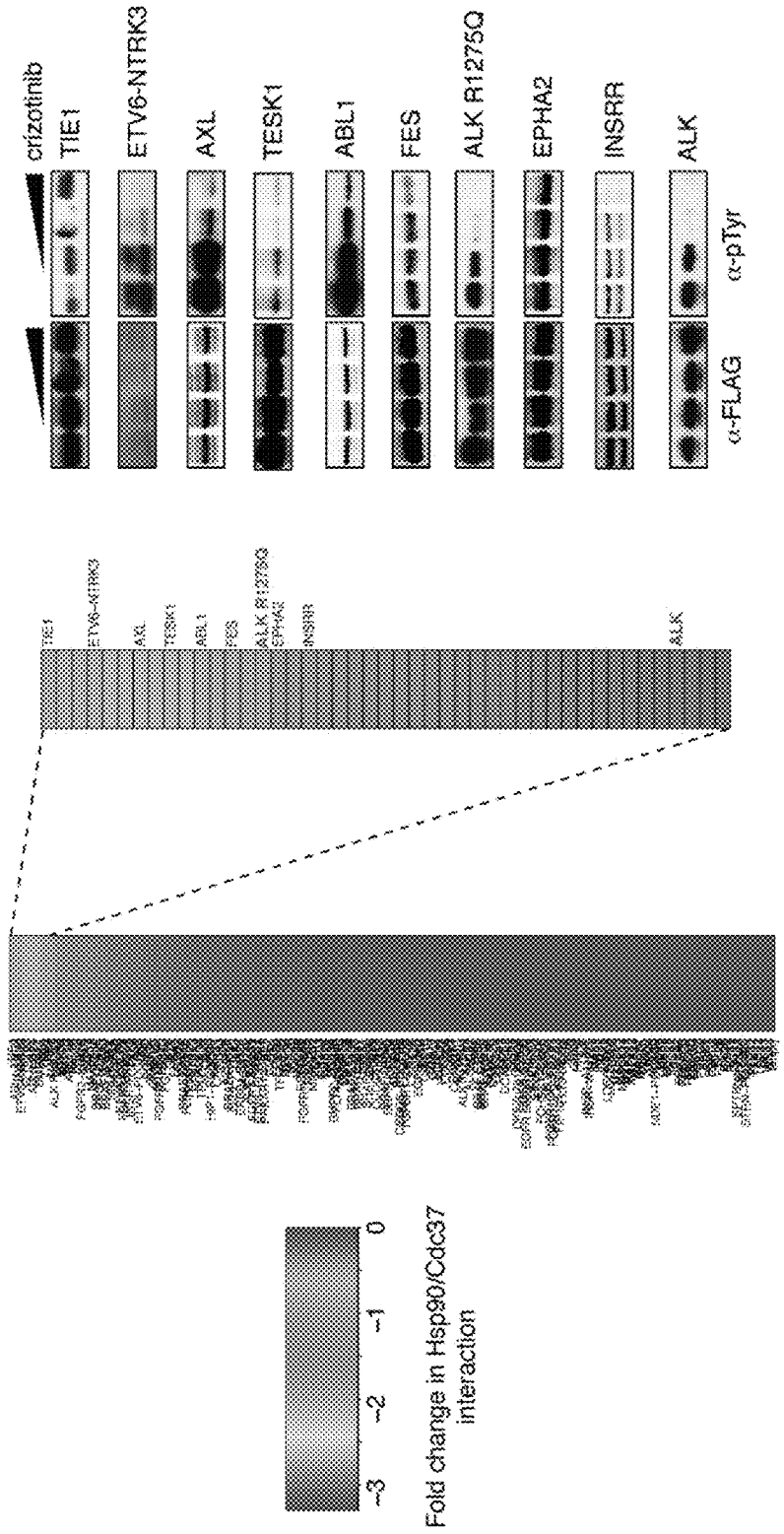

Example 6: Profiling the Effect of Various Kinase Inhibitors on HSP90β- or CDC37-Kinase Interactions Identifies Known Inhibitor Targets and Reveals New Targets QLPPI assays were used to quantitatively profile the effect of kinase inhibitors staurosporine, PLX4032, PLX4720, sorafenib, crizotinib, GNF-2, erlotinib, imatinib, and GDC-0879 on the interaction of HSP90β or CDC37 with members of our kinase panel. FIG. 9(A) shows heatmaps representing the fold change in interaction of HSP90β or CDC37 with individual kinases in the presence of each inhibitor, as compared with control (interaction measured with vehicle only added to wells), as determined in these assays. Control represents an assay in which compound was not added to either the "compound" or "no compound" wells. As noted above, staurosporine is known to inhibit numerous kinases. PLX4032 and PLX4720 have been characterized as selective inhibitors of the serine/threonine kinase BRAF, in particular BRAF having a V600E mutation, and PLX4032 has shown evidence of efficacy in clinical trials for treatment of melanoma characterized by the V600E mutation (Flaherty, K T, et al., N Engl J Med., 363(9):809-19, 2010; Tsai, J., et al., PNAS, 105(8): 3041-3046, 2008). Sorafenib is a multi-kinase inhibitor that targets several tyrosine kinases (VEGFR and PDGFR) and the serine/threonine kinase BRAF (Adnane, L., et al., Methods Enzymol., 407:597-612, 2006). Crizotinib (also known as PF-02341066) is an anaplastic lymphoma kinase (ALK) inhibitor under study in patients with advanced NSCLC carrying the echinoderm microtubule-associated protein-like 4 anaplastic lymphoma kinase (EML4-ALK) fusion gene. In addition to inhibiting ALK, crizotinib has been characterized as a MET inhibitor (Timofeevski S L, et al., Biochemistry. 48(23):5339-49, 2009). GDC-0879 has been characterized as a potent, selective B-RAF inhibitor (Wong, H., et al., Pharmacol Exp Ther. 329(1):360-7, 2009, and references therein).

The heatmaps in FIG. 9(A) provide an overall view of kinase inhibitor specificity. For example, it can readily be seen that staurosporine targets encompass a considerable fraction of the human kinome. In contrast, the other kinase inhibitors tested exhibit significantly less promiscuity but all of them also have multiple targets. Crizotinib exhibited most selectivity among the kinase inhibitors tested. Sorafenib is well known to be a multi-kinase inhibitor and, consistent with this designation, exhibited less selectivity than did the other kinase inhibitors tested, with the exception of staurosporine.

FIGS. 9(B)-9(E) show expanded views of the upper portions of the heatmaps for GNF-2, erlotinib, sorafenib, and PLX4720. Results indicate that various imatinib-resistant BCR-ABL mutants remain sensitive to GNF-2, consistent with GNF-2 binding to a different region of the kinase than does imatinib (Zhang, 2010). (BCR-ABL itself appears further down on the list of GNF-2 targets.) The heatmap for erlotinib shows that it inhibits numerous oncogenic EGFR mutants. (EGFR itself appears further down the list of erlotinib targets.)

Table 2 lists kinases whose interaction with HSP90β and/or CDC37 was significantly decreased by kinase inhibitors sorafenib, GNF-2, PLX4032, PLX4720, crizotinib, and/or GDC-0879 in our experiments performed to date. In Table 2, kinases that had been previously identified by others as targets of the respective kinase inhibitors are listed in bold font. Kinases that are newly identified as targets of the respective inhibitor(s) are indicated in regular font. For each inhibitor, multiple potential new targets were identified. A number of these targets are of significant relevance for investigation, diagnosis, and/or treatment of a variety of diseases.

Notably, numerous BCR-ABL mutants were identified as targets of crizotinib, including the BCR-ABL T315I mutant, which is resistant to the great majority of kinase inhibitors tested against it to date. Therefore, crizotinib and/or structural analogs thereof could be useful to inhibit BCR-ABL, including the BCR-ABL T315I mutant. Crizotinib and/or structural analogs thereof could be useful to treat diseases in which BCR-ABL plays a role, such as CML. Such compound(s) may be particularly useful to reduce development of drug resistance and/or to treat individuals with cancers that have become resistant to currently used BCR-ABL inhibitors such as imatinib that are ineffective against BCR-ABL T315I.

The initiation of programmed necrosis ("necroptosis") by death receptors (such as tumour necrosis factor receptor 1) requires the kinase activity of receptor-interacting protein 1 (RIP1; also known as RIPK1) and RIP3 (also known as RIPK3) (Vandenabeele, P., et al., Nat Rev Mol Cell Biol., 11(10):700-14, 2010). Necroptosis has been shown to participate in the pathogenesis of a variety of diseases, including ischaemic injury, neurodegeneration, and viral infection. Availability of small molecule inhibitors of RIPK1 would facilitate further investigation of the mechanisms of necroptosis and its role in normal and pathological processes. Inhibition of RIPK1 represents a promising strategy for the inhibition of deleterious cell death in conditions involving necroptosis such as ischemic injury and neurodegenerative diseases. As indicated in Table 2, PLX4032 and crizotinib both significantly inhibited chaperone-RIPK1 interaction, thus identifying these compounds as likely inhibitors of RIPK1. Therefore, PLX4032, crizotinib, and/or structural analogs of either of these compounds, could be useful as inhibitors of RIPK1 for research purposes and/or for therapeutic purposes such as treatment of diseases in which necroptosis plays a role.

Example 7: Characterization of Chaperone-Cochaperone Interactions

Figure 12:
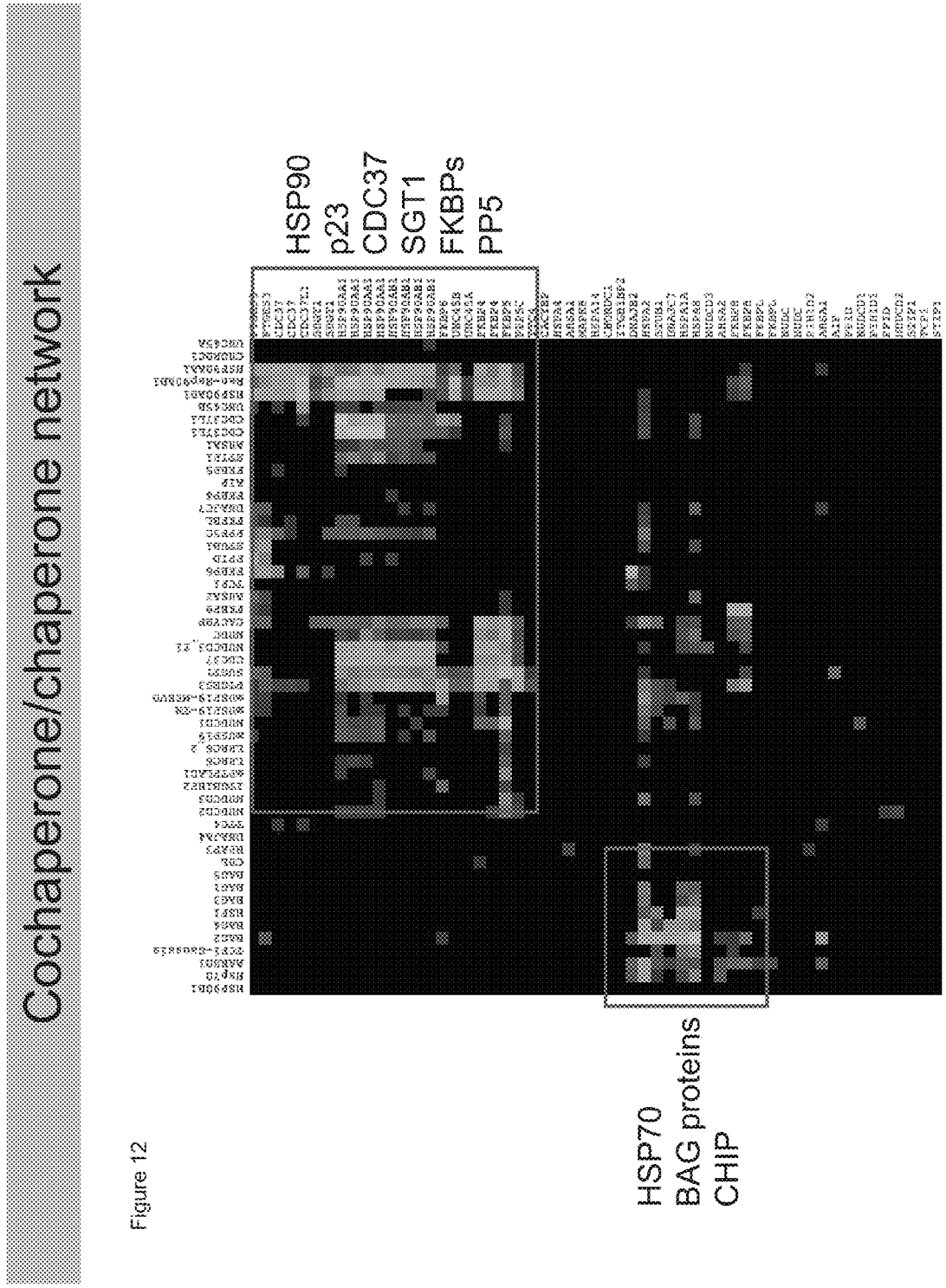
FIG. 12 is a heatmap that represents measurements of the strength of pairwise interactions between members of the panel of chaperones and co-chaperones listed in FIG. 11. Colors on this heatmap and the heatmaps in FIGS. 13-15 were assigned based on luminescence (fold enrichment over control, $\log_2$) with red representing higher enrichment as indicated.

QLPPI assays were used to investigate pairwise interactions between multiple different chaperones and co-chaperones. Chaperones were tagged with *Renilla* or *Gaussia* luciferase as described above, and co-chaperones were tagged with 3×FLAG-V5. Assays were performed using cell lines in which the luciferase-tagged proteins were stably expressed FIG. 11 lists chaperones and co-chaperones (columns labeled "TPR domains", "p23", and "Others") whose pairwise interaction was tested to develop a quantitative map reflecting a network of chaperone/co-chaperone interactions. FIG. 12 is a heatmap that quantitatively represents the strength of pairwise interactions between these chaperones and co-chaperones, as determined using QLPPI assays of the invention. In these experiments, measurements of the interaction were based on luminescence readings and did not include the FLAG ELISA measurement described above.

Example 8: Characterization of Chaperone-Client Interactions

QLPPI assays were used to investigate pairwise interactions between multiple different chaperones or co-chaperones with various client proteins. In these experiments, measurements of the interaction were based on luminescence readings and did not include the FLAG ELISA measurement described above.

Figure 13:
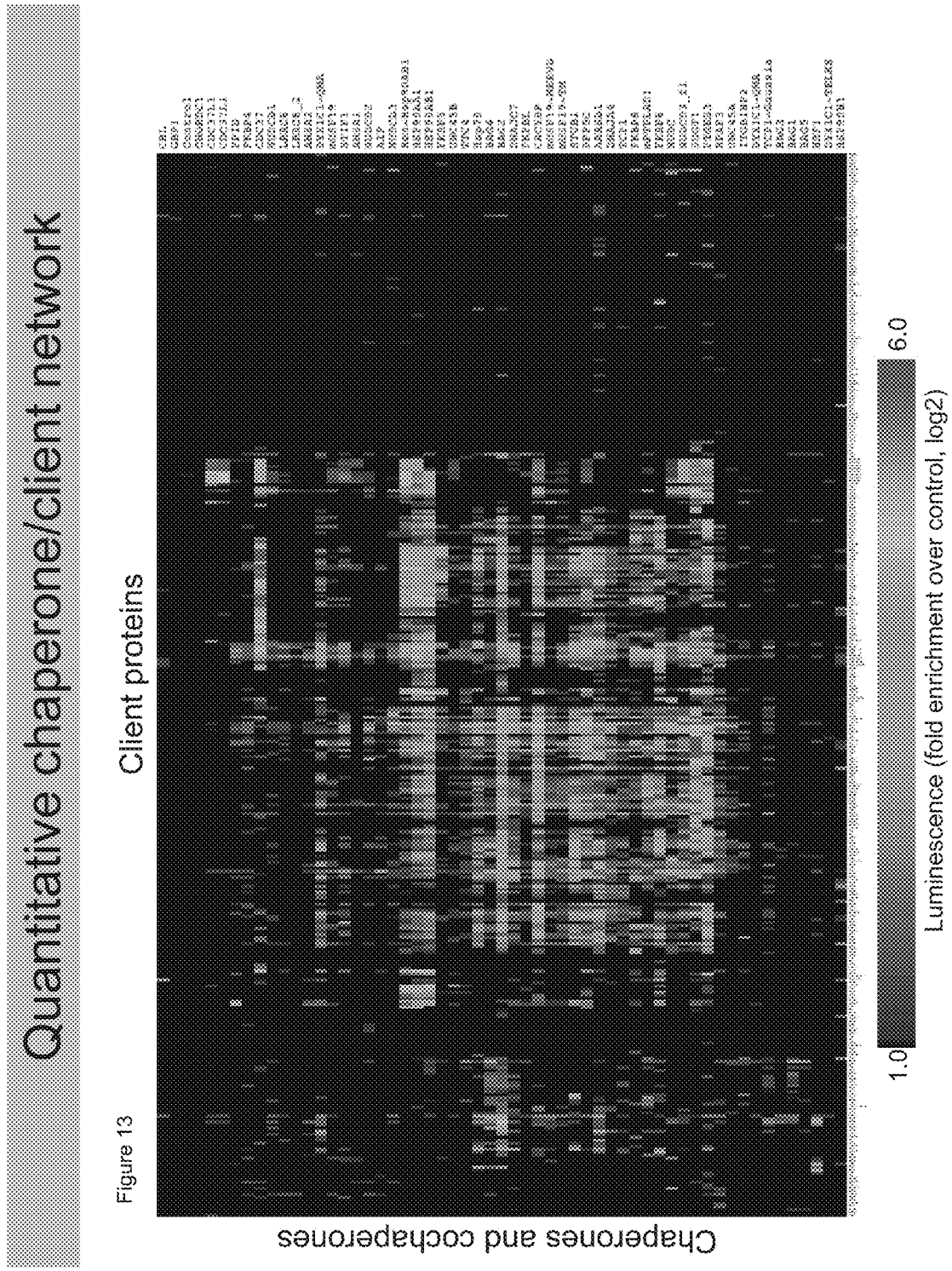
FIG. 13 is a heatmap that represents measurements of the strength of interactions between a panel of chaperones and co-chaperones with their clients. Colors were assigned based on luminescence (fold enrichment over control, $\log_2$) with red representing higher enrichment as indicated.

FIG. 13 is a heatmap that represents measurements of the chaperone-client interactions between members of a panel of chaperones and co-chaperones and a panel of diverse client proteins. These results confirm that the QLPPI assays described herein effectively identify chaperone-client interactions across a broad range of different chaperones and client proteins. Assays based on detecting alterations in chaperone-client interactions could be used to identify and/or characterize modulators of such client proteins.

Figure 14:
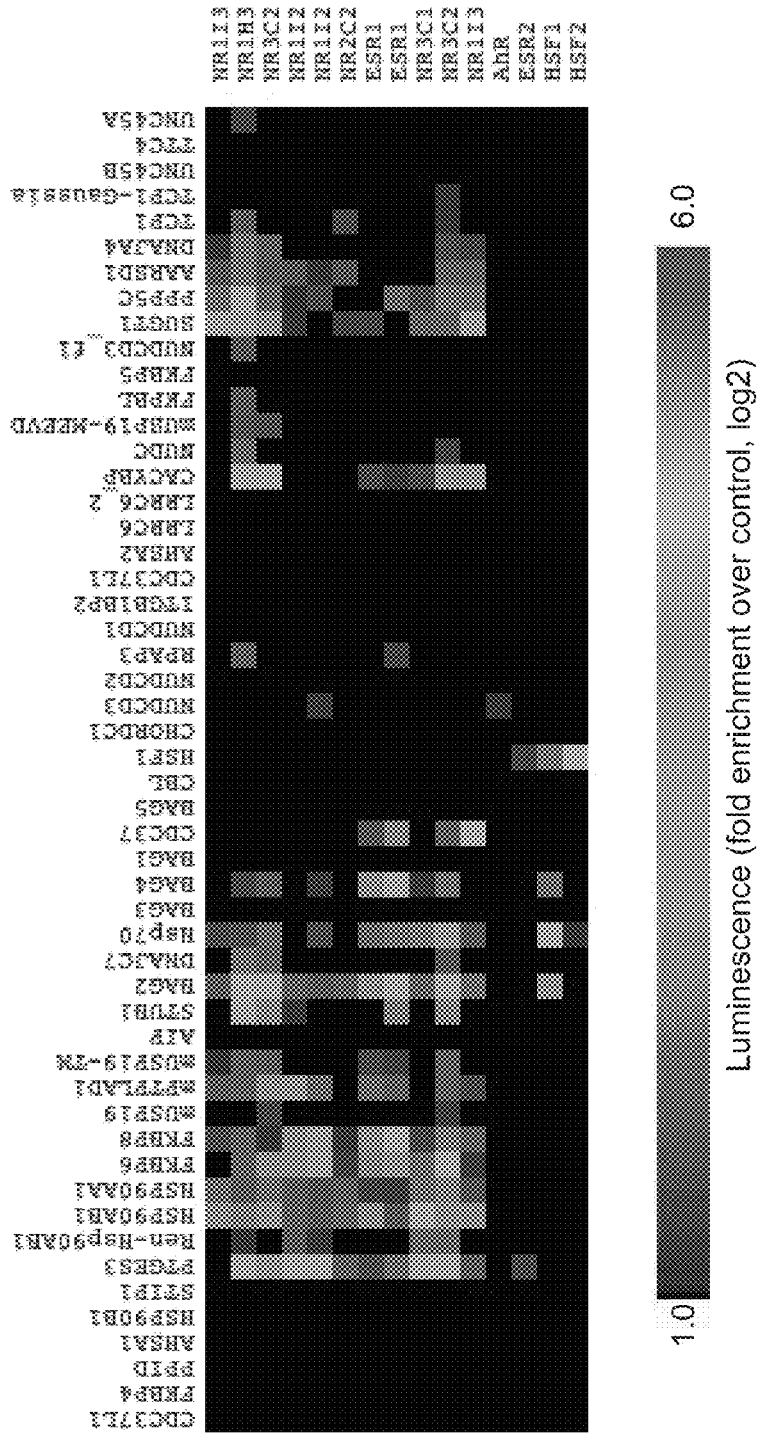
FIG. 14 is a heatmap that represents measurements of the strength of interactions between a panel of chaperones and a panel of nuclear hormone receptors or heat shock factor 1 (HSF1), as determined using a protein-protein interaction assay in which the chaperones were used as bait. HSF1 was included as both a prey and bait protein. HSF1 is known to form multimers, and the assay accurately detected HSF1's self-interaction.

FIG. 14 is a heatmap that represents measurements of interactions between a panel of chaperones and a panel of ligand-binding nuclear receptors (e.g., steroid hormone receptors such as glucocorticoid receptor, estrogen receptor, etc.) or HSF1, as determined using a protein-protein interaction assay of the invention in which the chaperones were used as bait. HSF1 was included as both a prey and bait protein. HSF1 is known to form oligomers (e.g., trimers), and the assay accurately detected HSF1 self-interaction as well as HSF1-HSF2 interaction, which is known to occur. These results suggest that small molecule modulators of HSF1 and/or HSF2 can be identified and/or characterized using a QLPPI assay of the invention. For example, small molecules that disrupt assembly of HSF1 oligomers would inhibit HSF1 self-interaction, and the reduced interaction would be detectable using a QLPPI assay.

Many ligand-binding nuclear receptors (LBNRs) have been previously shown to be HSP90 clients (Taipale, et al., 2010). Results shown in FIG. 13 confirm that an inventive QLPPI assay effectively detects interaction between HSP90 and numerous LBNRs. Small molecules that bind to a nuclear receptor would be expected to inhibit interaction between the receptor and HSP90, thus allowing identification and/or characterization of small molecule inhibitors of LBNRs in a similar manner as described for kinases. LBNRs have been implicated in a number of diseases, and a number of small molecule LBNR modulators are approved pharmaceutical agents. For example, corticosteroids are used as immunosuppressive, anti-inflammatory, and/or anti-proliferative agents in a wide variety of disorders. There is considerable interest in identifying LBNR modulators that selectively inhibit receptor activity in specific cell types and/or contexts. The results shown in FIG. 13 reveal interactions between various LBNRs and chaperones/co-chaperones. These results suggest that small molecule modulators of LBNRs can be identified and/or characterized by detecting alteration (e.g., reduction) in chaperone-LBNR interaction using a protein-protein interaction assay, e.g., a QLPPI assay of the invention.

Figure 15:
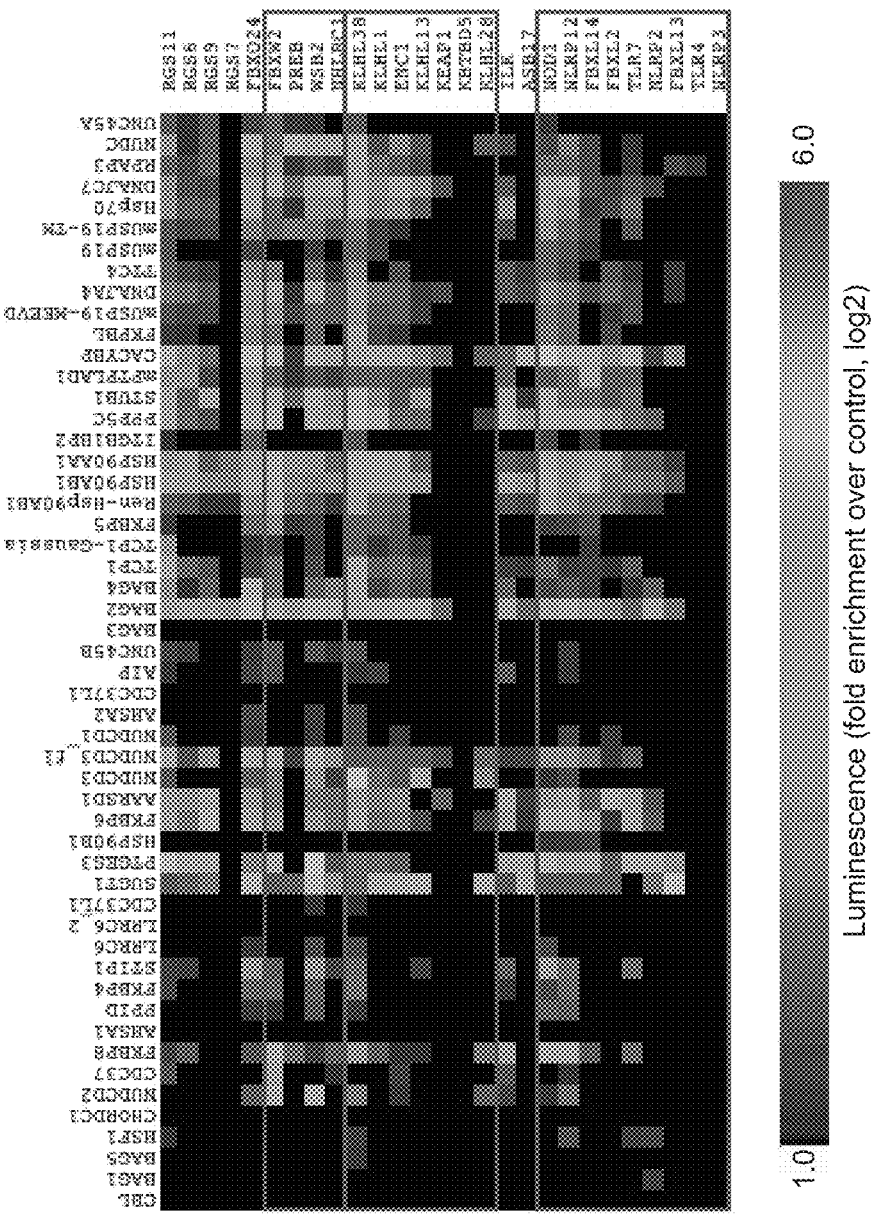
FIG. 15 is a heatmap that represents measurements of the strength of interactions between a panel of chaperones and a panel of proteins containing various repeat domains, as determined using a protein-protein interaction assay in which the chaperones were used as bait.

FIG. 15 is a heatmap that represents measurements of interactions between members of a panel of chaperones and members of a panel of client proteins containing various protein domains, as determined using a QLPPI assay of the invention in which luciferase-labeled chaperones were used as bait. These results reveal preferential interaction between particular co-chaperones and clients containing particular protein domains. FIG. 16 is a schematic diagram summarizing data from various experiments showing that co-chaperones NUDC, NUDCD2, NUDCD3, NUDC1, SGTI, and CDC37 interact preferentially with client proteins containing the indicated domains. For example, co-chaperone NUDC preferentially interacts with proteins containing WD40 domains. WD40 domains contain WD40 repeats, which are short structural motifs of approximately 40 amino acids, often terminating in a tryptophan-aspartic acid dipeptide. WD40 repeat proteins are a large family found in most or all eukaryotes and are implicated in a variety of functions ranging from signal transduction and transcription regulation to cell cycle control and apoptosis. WD-repeat proteins serve to coordinate multi-protein complex assemblies, wherein the repeating units serve as a scaffold.

These results suggest that small molecule modulators of client proteins that interact with any of a wide variety of chaperones/co-chaperones can be identified and/or characterized by detecting alteration (e.g., reduction) in chaperone-client interaction using a protein-protein interaction assay, e.g., a QLPPI assay of the invention.

Example 9: Profiling Crizotinib Using a QLPPI Assay

As mentioned above, we used the QLPPI assay to profile crizotinib (PF-02341066) with regard to a panel of kinases. So far, crizotinib had been characterized by others as a specific ALK/MET inhibitor. It has been shown to be 1000-fold selective over VEGFR2 and PDGFRB receptor tyrosine kinases, 250-fold selective over IRK and LCK tyrosine kinases, and 40-60-fold selective over TEK, NTRK1 and NTRK2 (Zou et al. Cancer Research, 67 (9): 4408-17, 2007). Recently, phase II clinical trials of crizotinib in non-small cell lung cancer were published and the results were striking (Kwak et al. New England Journal of Medicine, 363(18):1693-703, 2010; Butrynski et al. New England Journal of Medicine, 363(18):1734-9, 2010).

In the screen, we uncovered several novel targets of crizotinib (FIG. 6B) that were verified individually (FIG. 6C). A notable newly identified target of crizotinib was ETV6-NTRK3 translocation fusion protein, which is associated with secretory breast carcinoma, mesoblastic nephroma and congenital fibrosarcoma (Tognon, C., et al. (2002). Cancer Cell 2(5): 367-376, and references therein). Crizotinib inhibited the growth of ETV6-NTRK3 positive M091 cells (an acute myeloid leukemia (AML) cell line carrying a t(12;15) translocation) with IC50 of 5 nM (FIG. 6D). In contrast, the cells were completely resistant to BCR-ABL inhibitor imatinib. Furthermore, another ALK inhibitor, NVP-TAE684, was three orders of magnitude less potent in M091 cells (IC50: 1 µM) than crizotinib, suggesting that M091 growth inhibition does not occur through ALK. FIG. 6E shows results of an experiment in which crizotinib (100 mg/ml) was administered to mice harboring M091 tumor xenografts. The mice were treated orally using a gavage needle as per standard practice. Tumor volumes (mm^3) were calculated by measuring the length (long dimension in centimeters) and width (short dimension) of each mass with a caliper and then using the following standard formula to estimate volume: (length×width×width)×0.52×1000. Experimental groups for the experiment consisted of 8 mice per treatment (either crizotinib or vehicle). Cells were inoculated subcutaneously via 27 g needle in a 50/50 mix of PBS and Matrigel in the right inguinal region of each mouse. Daily treatment was begun about 3 weeks later when the average tumor volume across mice had reached ~350 mm^3. As shown in the graph presented in the upper half of FIG. 6(E), crizotinib dramatically inhibited M091 tumor xenograft growth. The panels in the lower half of FIG. 6(E) show from left to right: hematoxylin/eosin staining, immunohistochemical MIB1 staining, immunohistochemical phosphohistone H3 serine 10 (H3S10) staining, and immunohistochemical phosphotyrosine staining of representative samples from tumors in vehicle-treated (upper panels) or crizotinib-treated mice. MIB1 is a monoclonal antibody that recognizes the Ki67 antigen, a marker of cell proliferation. Phospho-histone H3 serine 10 is also a marker of cell proliferation. Phosphotyrosine levels are indicative of ETV6-NTRK3 activity. As can clearly be seen, the levels of MIB1, H3S10, and phosphotyrosine are much lower in tumor samples from crizotinib-treated mice than in tumor samples from mice treated with vehicle. These results indicate that crizotinib is useful to inhibit growth of cells that have aberrantly increased NTRK3 activity, e.g., cells that express an ETV6-NTRK3 fusion protein arising as a result of chromosomal translocation. These results also illustrate the ability of CCI assays to identify new, therapeutically relevant kinase inhibitor targets. A CCI assay was used to quantitatively assess of the effect of crizotinib on the interaction between HSP90 (3 and ALK, wild type NTRK3, or ETV6-NTRK3 fusion protein. Results are shown in FIG. 6(G) and indicate that crizotinib inhibited interaction with wild type NTRK3 and, more strongly, with the ETV6-NTRK3 fusion protein. The effect observed was more pronounced than the effect of crizotinib on its primary target, ALK.

Example 10: Predicting Kinase Mutant Sensitivity or Resistance

A CCI assay (using a QLPPI assay to measure interaction) was used to assess the effect of crizotinib on the interaction between HSP90β and ALK or various ALK mutants, thus profiling resistance/sensitivity of these kinases to inhibition by crizotinib. As shown in FIG. 6(F), crizotinib demonstrated ALKR1275Q was considerably more sensitive to crizotinib than ALK itself. Two other ALK mutants ALKF1174L and ALKT1151M) showed decreased sensitivity relative to ALK. These results are consistent with the finding that crizotinib inhibited proliferation of neuroblastoma cell lines expressing either R1275Q-mutated ALK or amplified wild-type ALK whereas, in contrast, cell lines harboring F1174L-mutated ALK were relatively resistant to crizotinib (Bresler, S C, et al., Sci Transl Med. 2011 3(108)): 108ra114).

Figure 17:
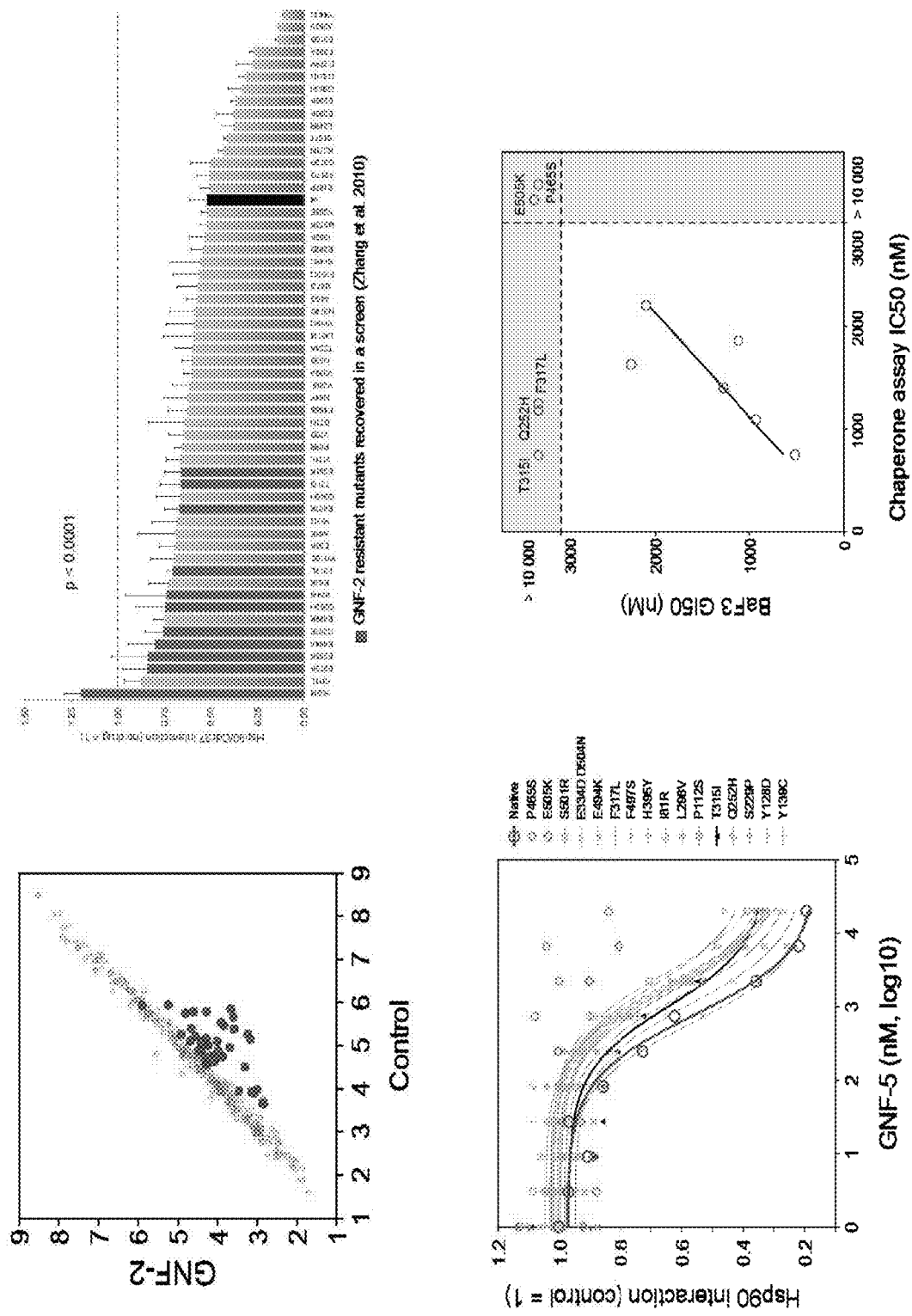
FIGS. 17(A) and 17(B) show profiling of interaction of HSP90β with native BCR-ABL and a panel of BCR-ABL mutants in the presence of GNF-2. The resistance/sensitivity of these kinases to imatinib, GNF-2, and/or GNF-5 had been assessed previously by others (Zhang, J, et al., Nature. 463(7280): 501-506, 2010). The CCI assay correctly identified mutant kinases that display resistance to GNF-2. These kinases display higher interaction scores than the sensitive kinases, indicative of the relative failure of GNF-2 to stabilize the resistant kinases.
Figure 17B:
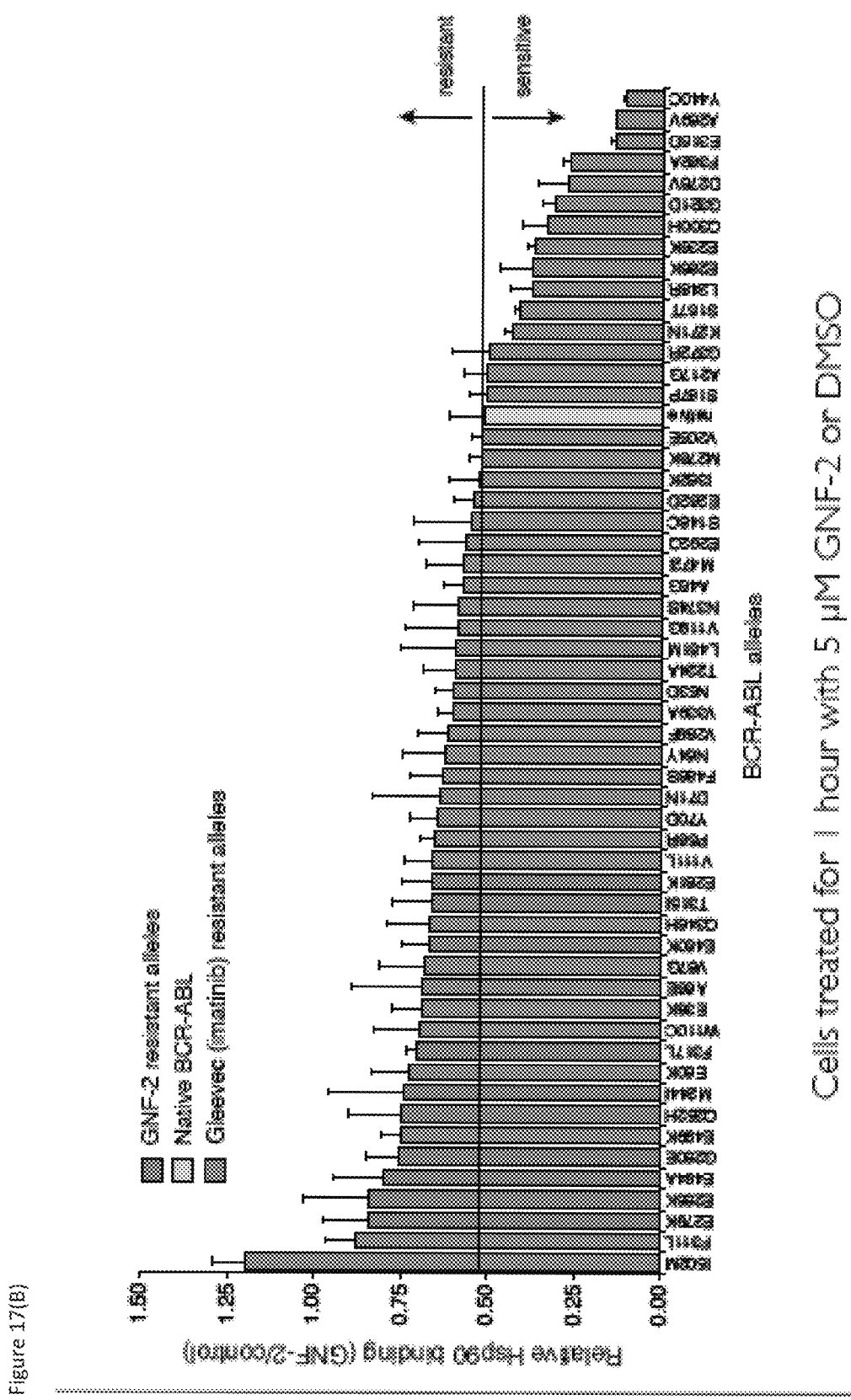

A CCI assay (using a QLPPI assay to measure interaction) was used to profile BCR-ABL and a panel of BCR-ABL mutants with regard to kinase inhibitor GNF-2 or GNF-5 (Zhang, et al., 2010). The effect of GNF-2 or GNF-5 on interaction of these kinases with HSP90β was assessed. The CCI assay revealed the level of resistance/sensitivity of the various kinases to GNF-2 or GNF-5 (FIGS. 17(A) and 17(B). The lower left panel of FIG. 17(A) shows correlation of the IC50 for GNF2 on interaction of various BCR-ABL alleles with HSP90β versus ability of the compound to inhibit growth of BaF3 cells expressing the corresponding kinase allele.

Example 11: Kinase Activator Alters HSP90β-Kinase Interactions

Figure 18:
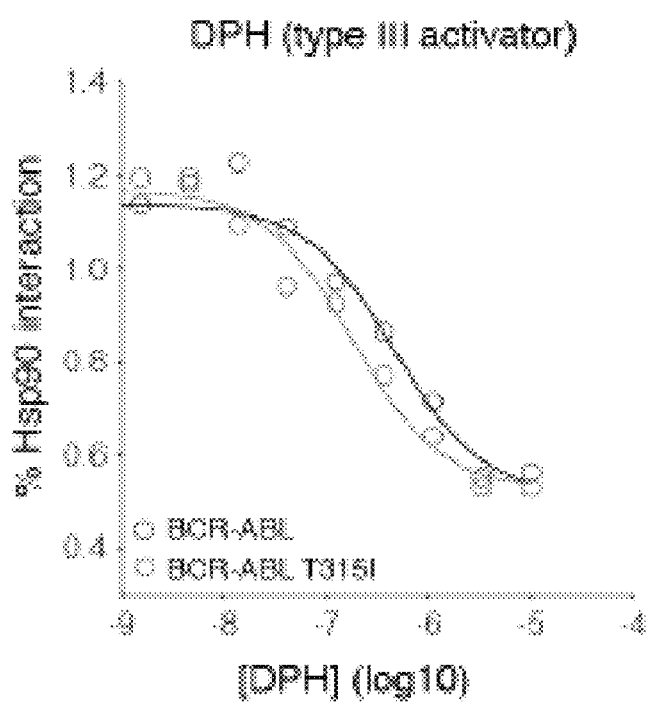
FIG. 18 shows quantitative assessment of the effect of kinase activator DPH (a type III activator) on the interaction between BCR-ABL (blue) or the T351I BCR-ABL mutant (orange) and HSP90β.
Figure 19:
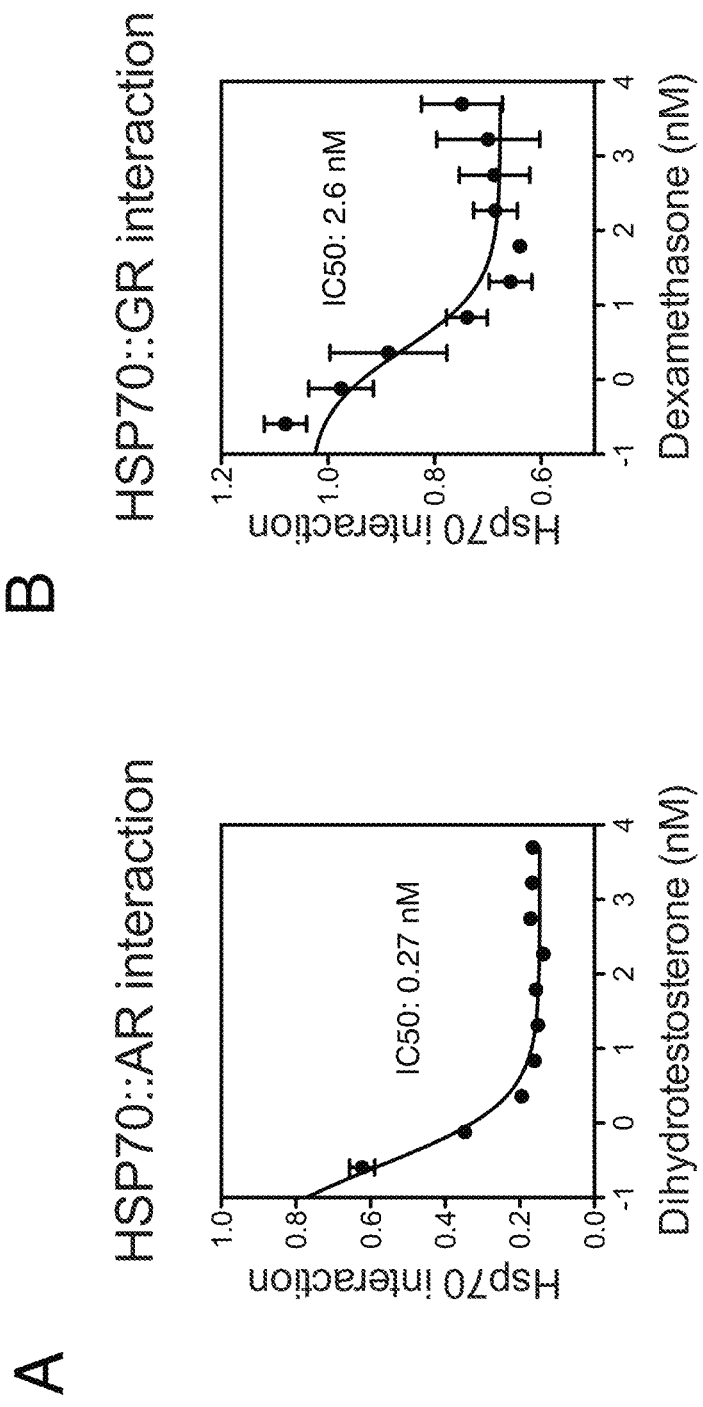
FIG. 19A shows a quantitative assessment of the effect of dihydrotestosterone on the interaction between HSP70 (HSPA8) and androgen receptor (AR).
FIG. 19B shows a quantitative assessment of the effect of dexamethasone on the interaction between HSP70 (HSPA8) and glucocorticoid receptor (GR).

We quantitatively assessed the effect of DPH on the interaction between chaperone HSP90β and BCR-ABL or the T351I BCR-ABL mutant over a range of inhibitor concentrations using a QLPPI assay. As shown in FIG. 18, DPH inhibited the interaction of both BCR-ABL and the T351I BCR-ABL mutant with HSP90β. These results confirm the ability of CCI assays (e.g., using a QLPPI assay to measure interaction) to, e.g., identify candidate kinase activators, determine whether a kinase of interest is activated by a kinase activator or interest, or to profile kinase activators.

Example 12: Chaperone-Client Interaction Assay Quantitatively Detects Nuclear Receptor:Ligand Interactions This Example demonstrates use of a chaperone-client interact assay to detect and quantify nuclear receptor:ligand interactions. Human androgen receptor (AR) and glucocorticoid receptor (GR) were tagged with 3× FLAG, and constructs encoding the proteins were transfected into a stable HEK-293T cell line expressing Renilla-HSPA8 fusion protein. The AR and GR cDNA clones correspond to GenBank accession numbers BC132975 and BC015610 respectively, and are members of the Mammalian Gene Collection (mgc.nci.nih.gov/). The cDNAs can be obtained, e.g., from distributors of the IMAGE consortium. Cells were treated with increasing doses of ligands (dihydrotestosterone or dexamethasone, respectively) for 1 h, after which cells were lysed and interaction between HSPA8 (HSP70) and AR (panel A) or HSPA8 and GR (panel B) measured with the enhanced LUMIER assay described above. IC50 values obtained were consistent with the compounds' cellular potencies (EC50s). These data show that chaperone-client interaction assays can be used to detect hormone::receptor interactions, such as testosterone binding to the androgen receptor (AR) and dexamethasone binding to the glucocorticoid receptor (GR). In this example, the sensor chaperone is HSP70, confirming that the assay provides quantitative results with this chaperone.

Those skilled in the art will recognize, or be able to ascertain using no more than routine experimentation, many equivalents to the specific embodiments of the invention described herein. The scope of the present invention is not intended to be limited to the Description or the details set forth therein. Articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). In particular, any claim that is dependent on another claim can be modified to include one or more elements or limitations found in any other claim that is dependent on the same base claim. Furthermore, where the claims recite a composition or product, the invention provides methods of making the composition or product, e.g., according to methods disclosed herein, and methods of using the composition or product, e.g., for purposes disclosed herein. Where the claims recite a method, the invention provides compositions or products of use in the methods, and methods of making such compositions or products, unless otherwise indicated or unless one of ordinary skill in the art would recognize that a contradiction or inconsistency would arise.

Where elements are presented as lists herein, e.g., in Markush group format, each subgroup of the elements is also disclosed, and any element(s) can be removed from the group. For purposes of conciseness only some of these embodiments have been specifically recited herein, but the invention includes all such embodiments. It should also be understood that, in general, where the invention, or aspects of the invention, is/are referred to as comprising particular elements, features, etc., certain embodiments of the invention or aspects of the invention consist, or consist essentially of, such elements, features, etc. Aspects and embodiments of the invention may be freely combined, with the resulting combinations being encompassed by the invention.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

In addition, any particular embodiment(s), aspect(s), element(s), feature(s), etc., of the present invention may be explicitly excluded from any one or more claims. For example, any agent, small molecule (e.g., any kinase inhibitor), bait protein, prey protein, protein of interest, chaperone, co-chaperone, detectable label, tag, or disease, may be explicitly excluded from any one or more claims.

TABLE 1

| HSP90 client kinases | Oncogenic mutant kinases that interact with HSP90 | Drug resistant alleles that interact with HSP90 | Kinase fusion proteins (translocations) that interact with HSP90 | Other disease-associated mutant kinases that interact with HSP90 |
|---|---|---|---|---|
| ABL1 | EGFR G719S | BCR-ABL T315I | CCDC6-PDGFRB | FGFR1-W666R |
| ACVR1B | EGFR del3 | BCR-ABL F317L | ETV6-FGFR3 | FGFR1-V607M |
| ACVR1C | EGFR insNPG | BCR-ABL F382A | ETV6-FLT3 | FGFR1-R622G |
| ACVR2B | EGFR L858R | BCR-ABL H396P | ETV6-NTRK3 | FLT4-H1035R |
| AKT2 | EGFR T790M | BCR-ABL Y440C | ETV6-PDGFRA | FLT4-L1044P |
| ALK | EGFR L858R T790M | BCR-ABL M244I | ETV6-PDGFRB | FLT4-P1114L |

TABLE 1-continued

| HSP90 client kinases | Oncogenic mutant kinases that interact with HSP90 | Drug resistant alleles that interact with HSP90 | Kinase fusion proteins (translocations) that interact with HSP90 | Other disease-associated mutant kinases that interact with HSP90 |
|---|---|---|---|---|
| ALPK1 | EGFR vIII | BCR-ABL T224A | E7V6-SYK | INSR-A1161T |
| ALS2CR7 | FLT3 D835Y | BCR-ABL A269V | FCHSD1-BRAF | INSR-R1201Q |
| AMHR2 | FLT3 ITD | BCR-ABL L248R | FGFR1OP-FGFR1 | INSR-W1227S |
| ARAF | RET M918T | BCR-ABL G250E | FGFR1OP2-FGFR1 | BMPR2-C483R |
| AURKB | ALK T1151M | BCR-ABL Q252H | HIP1-PDGFRB | BMPR2-R491Q |
| AURKC | ALK F1174L | BCR-ABL Y253H | ITK-SYK | TGFBR1-D400G |
| AXL | ALK R1275Q | BCR-ABL E285K | KTN1-RET | TGFBR1-R487P |
| BLK | BRAF G464V | BCR-ABL D276V | MSN-ALK | FGFR2-NS49H |
| BMPR1A | BRAF G466A | BCR-ABL M278K | NCOA4-RET | FGFR2-E56SG |
| BMX | BRAF G466E | BCR-ABL E279K | NDE1-PDGFRB | FGFR2-K641R |
| BRAF | BRAF G466V | BCR-ABL E281K | PRKAR1A-RET | FGFR2-A648T |
| BTK | BRAF G469A | BCR-ABL E282D | SPTBN1-FLT3 | |
| CAMK1G | BRAF G469E | BCR-ABL V289F | STRN-PDGFRA | |
| CAMK2A | BRAF E586K | BCR-ABL F311L | TFG-ALK | |
| CAMK2B | BRAF D594V | BCR-ABL E316D | TFG-NTRK1 | |
| CAHK2D | BRAF G596R | BCR-ABL T315I | TPM3-ALK | |
| CAMK2G | BRAF V600E | BCR-ABL Q346H | TPM3-PDGFRB | |
| CAMK4 | BRAF K601E | BCR-ABL I352K | TPM4-ALK | |
| CAMKK1 | BRAF A727V | BCR-ABL Q300H | CCDC6-RET | |
| CAMKK2 | PDGFRA-D842V | BCR-ABL V339A | FIP1L1-PDGFRA | |
| CAMKV | PDGFRA T674M D842V | BCR-ABL E292Q | NPM1-ALK | |
| CDC2L1 | | BCR-ABL N374S | TPR-MET | |
| CDK3 | | BCR-ABL G372R | | |
| CDK4 | | BCR-ABL H396R | | |
| CDK6 | | BCR-ABL M472I | | |
| CDK7 | | BCR-ABL E450K | | |
| CDK9 | | BCR-ABL F486S | | |
| CHEK1 | | BCR-ABL I502M | | |
| CLK2 | | BCR-ABL E494A | | |
| CLK3 | | BCR-ABL E499K | | |
| CSF1R | | BCR-ABL G321D | | |
| CSNK1A1 | | BCR-ABL L451M | | |
| DAPK3 | | BCR-ABL E236K | | |
| DCAMKL2 | | BCR-ABL E286K | | |
| DDR1 | | BCR-ABL K271N | | |
| DDR2 | | EGFR L858R T790M | | |
| DKFZp761P0423 | | EGFR T790M | | |
| DMPK | | PDGFRA-T674M | | |
| DYRK1B | | PDGFRA T674M D842V | | |
| DYRK2 | | | | |
| DYRK4 | | | | |
| EIF2AK1 | | | | |
| EPHA1 | | | | |
| EPHA2 | | | | |
| EPHA4 | | | | |
| EPHB1 | | | | |
| EPHB6 | | | | |
| ERBB2 | | | | |
| ERBB3 | | | | |
| ERBB4 | | | | |
| FASTK | | | | |
| FER | | | | |
| FES | | | | |
| FGFR1 | | | | |
| FGFR3 | | | | |
| FGR | | | | |
| FLT4 | | | | |
| FRK | | | | |
| FYN | | | | |
| GRK4 | | | | |
| GRK6 | | | | |
| GRK7 | | | | |
| GSK3A | | | | |
| HCK | | | | |
| HIPK4 | | | | |
| ICK | | | | |
| IGF1R | | | | |
| IKBKE | | | | |
| ILK | | | | |
| INSRR | | | | |
| IRAK2 | | | | |
| IRAK3 | | | | |
| ITK | | | | |
| JAK1 | | | | |
| KSR1 | | | | |
| KSR2 | | | | |

TABLE 1-continued

| HSP90 client kinases | Oncogenic mutant kinases that interact with HSP90 | Drug resistant alleles that interact with HSP90 | Kinase fusion proteins (translocations) that interact with HSP90 | Other disease-associated mutant kinases that interact with HSP90 |
|---|---|---|---|---|
| LCK | | | | |
| LIMK1 | | | | |
| LIMK2 | | | | |
| LOC91807 | | | | |
| LYN | | | | |
| MAP2K5 | | | | |
| MAP2K7 | | | | |
| MAP3K12 | | | | |
| MAP3K14 | | | | |
| MAP3K15 | | | | |
| MAP3K2 | | | | |
| MAP3K5 | | | | |
| MAP3K6 | | | | |
| MAP3K8 | | | | |
| MAP3K9 | | | | |
| MAP4K1 | | | | |
| MAP4K2 | | | | |
| MAP4K4 | | | | |
| MAPK15 | | | | |
| MAPK4 | | | | |
| MAPK7 | | | | |
| MAST2 | | | | |
| MATK | | | | |
| MERTK | | | | |
| MINK1 | | | | |
| MOS | | | | |
| MUSK | | | | |
| MYLK2 | | | | |
| MYLK4 | | | | |
| MYO3B | | | | |
| NEK11 | | | | |
| NEK8 | | | | |
| NEK9 | | | | |
| NPR2 | | | | |
| NTRK1 | | | | |
| NTRK2 | | | | |
| NTRK3 | | | | |
| NUAK2 | | | | |
| PAK6 | | | | |
| PASK | | | | |
| PCTK3 | | | | |
| PDGFRB | | | | |
| PDIK1L | | | | |
| PFTK1 | | | | |
| PIM2 | | | | |
| PIM3 | | | | |
| PINK1 | | | | |
| PKN1 | | | | |
| PKN2 | | | | |
| PRKAA1 | | | | |
| PRKAA2 | | | | |
| PRKACB | | | | |
| PRKCA | | | | |
| PRKCB1 | | | | |
| PRKCE | | | | |
| PRKCG | | | | |
| PRKCH | | | | |
| PRKCI | | | | |
| PRKCQ | | | | |
| PRKCZ | | | | |
| PRKD1 | | | | |
| PRKD2 | | | | |
| PRKG2 | | | | |
| PRKR | | | | |
| PRKX | | | | |
| PRKY | | | | |
| PSKH1 | | | | |
| PSKH2 | | | | |
| PTK2 | | | | |
| PTK2B | | | | |
| PTK6 | | | | |
| RAF1 | | | | |
| RET | | | | |
| RIPK1 | | | | |
| ROR2 | | | | |
| RPS6KA1 | | | | |

TABLE 1-continued

| HSP90 client kinases | Oncogenic mutant kinases that interact with HSP90 | Drug resistant alleles that interact with HSP90 | Kinase fusion proteins (translocations) that interact with HSP90 | Other disease-associated mutant kinases that interact with HSP90 |
|---|---|---|---|---|
| RPS6KA2 | | | | |
| RPS6KA3 | | | | |
| RPS6KA5 | | | | |
| RPS6KA6 | | | | |
| RPS6KB1 | | | | |
| RPS6KC1 | | | | |
| RPS6KL1 | | | | |
| SGK | | | | |
| SGK2 | | | | |
| SGK3 | | | | |
| SRPK1 | | | | |
| SRPK3 | | | | |
| STK11 | | | | |
| STK32B | | | | |
| STK32C | | | | |
| STK38 | | | | |
| STK38L | | | | |
| STYK1 | | | | |
| TAOK3 | | | | |
| TBK1 | | | | |
| TESK1 | | | | |
| TESK2 | | | | |
| TIE1 | | | | |
| TNK1 | | | | |
| TNK2 | | | | |
| TNNI3K | | | | |
| TP53RK | | | | |
| TSSK1 | | | | |
| TSSK2 | | | | |
| TSSK3 | | | | |
| TSSK6 | | | | |
| TYK2 | | | | |
| TYRO3 | | | | |
| WNK4 | | | | |
| YES1 | | | | |
| MTOR | | | | |
| ROS | | | | |

TABLE 2

| Sorafenib | GNF-2 | PLX4032 | PLX4720 | Crizotinib | GDC-0879 |
|---|---|---|---|---|---|
| ETV6-FLT3 | BCR-ABL Y440C | BRAF G469E | BRAF G469E | BCR-ABL A269V | BRAF G466V |
| FIP1L1-PD6FRA | BCR-ABL E316D | BRAF G466V | BRAF G466E | BCR-ABL F311L | BRAF G469A |
| ETV6-PDGFRA | BCR-ABL A269V | MYLK4 | BRAF G466V | BCR-ABL Q300H | BRAF |
| FGFR2 E565G | BCR-ABL Q300H | BRAF G466E | BRAF G466A | BCR-ABL E316D | BRAF K601E |
| ETV6-PDGFRB | BCR-ABL L248R | RIPK1 | BRAF G469A | BCR-ABL E292Q | BRAF V600E |
| BRAF G469A | BCR-ABL G372R | BCR-ABL E316D | BRAF | BCR-ABL N374S | BRAF D594V |
| ETV6-NTRK3 | BCR-ABL G321D | BRAF D594V | BRAF V600E | BCR-ABL M472I | BRAF G596R |
| FGFR2 K641R | BCR-ABL Q346H | BRAF G466A | BRAF V600E | BCR-ABL G372R | INSR-A1161T |
| PRKAR1A-RET | ABL1 | INSR-R1201Q | NEK11 | BCR-ABL I352K | BRAF G464V |
| FLT3 ITD | BCR-ABL M472I | FIP1L1-PDGFRA | SNF1LK | BCR-ABL V289F | FCHSD1-BRAF |
| TIE1 | BCR-ABL D276V | BCR-ABL Q300H | FIP1L1-PDGFRA | BCR-ABL T315I | AKT2 |
| DDR1 | BCR-ABL E282D | STK32B | BRAF K601E | BCR-ABL E450K | BCR-ABL T224A |
| NTRK3 | BCR-ABL F382A | BCR-ABL | BRAF E586K | BCR-ABL Q252H | |
| BCR-ABL E316D | BCR-ABL F486S | INSR | FCHSD1-BRAF | BCR-ABL E281K | |
| FGFR1OP2-FGFR1 | BCR-ABL E236K | BRAF G469A | ARAF | TIE1 | |
| BRAF K601E | BCR-ABL wt | PRKAR1A-RET | BCR-ABL E316D | BCR-ABL I502M | |
| BCR-ABL A269V | BCR-ABL L451M | NEK11 | ETV6-PDGFRA | BCR-ABL E494A | |
| CDK7 | BCR-ABL K271N | BCR-ABL L451M | STK25 | BCR-ABL Q346H | |
| BRAF D594V | BCR-ABL N374S | BCR-ABL N374S | BCR-ABL Y440C | BCR-ABL Y440C | |
| BRAF V600E | ABL1 G2A | BCR-ABL E282D | DDR1 | ABL1 T315I | |
| BRAF G466A | BCR-ABL E286K | FGR | BRAF A727V | INSR | |
| CCDC6-PDGFRB | BCR-ABL M278K | BRAF G596R | BCR-ABL K271N | ETV6-NTRK3 | |
| TPM3-PDGFRB | BCR-ABL E292Q | INSR-A1161T | RAF1 | BCR-ABL T224A | |
| FGFR1OP-FGFR1 | BCR-ABL V339A | LCK | NUAK2 | BCR-ABL F486S | |
| BRAF E58SK | BCR-ABL T224A | BRAF F382A | MAPKAPK2 | RIPK1 | |
| INSR-A1161T | BCR-ABL E450K | BCR-ABL V289F | MAPK1 | ALK R1275Q | |
| PDGFRB | BCR-ABL E281K | BCR-ABL E292Q | ACVR2B | BCR-ABL G250E | |
| FLT3 | BCR-ABL | BCR-ABL I352K | TNNI3K | ABL1 G2A | |
| BRAF 6464V | BCR-ABL T315I | BCR-ABL Y440C | FLT4 | TESK1 | |
| FLT4 | BCR-ABL Q252H | BCR-ABL K271N | MAP2K5 | IKBKE | |
| BCR-ABL Y440C | CAMKV | BCR-ABL E281K | TP53RK | BCR-ABL F382A | |

TABLE 2-continued

| Sorafenib | GNF-2 | PLX4032 | PLX4720 | Crizotinib | GDC-0879 |
|---|---|---|---|---|---|
| TNNI3K | BCR-ABL E494A | ABL1 G2A | FGFR3 | AURKC | |
| BRAF G466E | TP53RK | BCR-ABL E286K | BMPR1A | ABL1 | |
| FGFR1 | CAMK4 | BCR-ABL M278K | MERTK | FES | |
| BRAF | | BCR-ABL T224A | BCR-ABL E286K | AMHR2 | |
| F6FR2-N549H | | BCR-ABL E236K | ERBB3 | BCR-ABL F317L | |
| BCR-ABL L451M | | BRAF V600E | PKN1 | BCR-ABL D276V | |
| CCDC6-RET | | BCR-ABL M244I | RPS6KA3 | ALK | |
| FCHSD1-BRAF | | ARAF | TPM3-ALK | EPHA2 | |
| NTRK1 | | CDK6 | LCK | BCR-ABL L248R | |
| BCR-ABL I502M | | ABL1 | PRKAA1 | STK33 | |
| BCR-ABL E499K | | IKBKE | | SRPK3 | |
| INSR R1201Q | | TYRO3 | | FGFR2 K641R | |
| AURKB | | BCR-ABL M472I | | MAP3K2 | |
| CHEK1 | | BCR-ABL E450K | | BRAF G468E | |
| BCR-ABL | | BCR-ABL Q252H | | LCK | |
| TNK2 | | BCR-ABL F311L | | BRAF G465V | |
| BCR-ABL M278K | | BCR-ABL E494A | | NPM1-ALK | |
| RET | | CDC2L2 | | | |
| BCR-ABL G372R | | EGFR L858R | | | |
| FGFR1 V607M | | FCHSD1-BRAF | | | |
| PDIK1L | | PFTK1 | | | |
| BCR-ABL F486S | | BCR-ABL G372R | | | |
| NPM1-ALK | | PKN1 | | | |
| TPM3-ALK | | BCR-ABL G250E | | | |
| BCR-ABL E494A | | | | | |
| BCR-ABL M472I | | | | | |
| ALK | | | | | |

We claim:

1. A method for detecting a protein-protein interaction, the method comprising steps of:
   (a) providing a lysate prepared from cells that express a prey protein and a bait protein, wherein the prey protein is labeled with a detectable label and the bait protein is tagged with a heterologous epitope tag that allows separation of the bait protein and protein(s) interacting with the bait protein from other proteins in the lysate;
   (b) immobilizing the tag to one or more inner surface(s) of a well, thereby immobilizing the bait protein and protein(s) interacting with the bait protein;

(c) detecting immobilized prey protein by detecting the detectable label, thereby detecting a protein-protein interaction; and (d) detecting immobilized bait protein and measuring the protein-protein interaction based on the ratio of prey protein to bait protein detected.

2. The method of claim 1, wherein the cells stably express the prey protein, and are transiently transfected with an expression vector that causes them to express the bait protein.

3. The method of claim 1, wherein the bait protein comprises a receptor, nuclear receptor, transcription factor, mitochondrial protein imported from the cytoplasm, calcineurin, heat shock factor 1 (HSF1), telomerase reverse transcriptase (TERT), endothelial nitric oxide synthase (eNOS), viral protein, myosin, argonaute, leucine rich repeat (LRR) protein, or kinase.

4. The method of claim 1, wherein the bait protein comprises a WD40 domain, RCC1 repeat, Kelch domain, WDAD repeat, NHL repeat, or leucine-rich repeat.

5. The method of claim 1, wherein the prey protein comprises a chaperone, an HSP, an HSP90 or HSP90 co-chaperone, an HSP90 or CDC37 protein, or an NUDC domain.

6. The method of claim 1, wherein the prey protein comprises a chaperone and the bait protein comprises a kinase.

7. A method of assessing the effect of a test agent on a protein-protein interaction between a bait protein and a prey protein, the method comprising steps of:

(a) measuring a protein-protein interaction between a bait protein and a prey protein according to the method of claim 1, wherein the lysate has been prepared from cells that have been exposed to a test agent; and (b) comparing the result of step (a) with a result of measuring a protein-protein interaction between the bait protein and the prey protein in the absence of the test agent, wherein if the results differ, the test agent modulates the protein-protein interaction, while if the results do not differ, the test agent does not modulate the protein-protein interaction.

8. The method of claim 7, wherein the prey protein or the bait protein comprises a chaperone, receptor, nuclear receptor, transcription factor, mitochondrial protein imported from the cytoplasm, calcineurin, heat shock factor 1 (HSF1), telomerase reverse transcriptase (TERT), endothelial nitric oxide synthase (eNOS), viral protein, myosin, argonaute, leucine rich repeat (LRR) protein, or kinase.

9. The method of claim 7, wherein the prey protein and the bait protein are a chaperone-client pair, and wherein the method further comprises identifying the test agent as a candidate modulator of the client if the result of step (a) is less than the result obtained in the absence of the test agent, or wherein the client comprises a kinase, and wherein the method further comprises identifying the test agent as a candidate inhibitor of the kinase if the result of step (a) is less than the result obtained in the absence of the test agent.

10. The method of claim 7, wherein the prey protein and the bait protein are an enzyme-substrate pair.

11. The method of claim 7, wherein the prey protein and the bait protein are subunits of a protein complex.

12. A method of characterizing a test agent, the method comprising performing the method of claim 7 multiple times using the same prey protein, the same test agent, and different bait proteins, thereby obtaining a profile of the effect of the test agent on multiple bait proteins.

13. The method of claim 12, wherein the bait proteins comprise a set of proteins that are participate in protein-protein interactions with the prey protein in the absence of the test agent.

14. The method of claim 12, wherein the prey protein comprises (i) a chaperone protein, and at least some of the bait proteins are clients of the chaperone protein, (ii) an HSP90 protein or an HSP90 co-chaperone, and the bait proteins comprise HSP90 clients, (iii) an HSP90 protein or an HSP90 co-chaperone, and the bait proteins comprise kinases, or (iv) a mammalian HSP90 protein, and the bait proteins comprise mammalian kinases.

* * * * *